(12) United States Patent
Voronkov et al.

(10) Patent No.: US 11,518,738 B2
(45) Date of Patent: *Dec. 6, 2022

(54) COMPOUNDS AND METHODS OF USE

(71) Applicant: Signum Biosciences, Inc., Monmouth Junction, NJ (US)

(72) Inventors: Michael Voronkov, Monmouth Junction, NJ (US); Edwardo Perez, Monmouth Junction, NJ (US); Jason Healy, Monmouth Junction, NJ (US); Jose Fernandez, Monmouth Junction, NJ (US)

(73) Assignee: Signum Biosciences, Inc., Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/199,511

(22) Filed: Mar. 12, 2021

(65) Prior Publication Data

US 2021/0261499 A1 Aug. 26, 2021

Related U.S. Application Data

(63) Continuation of application No. 16/469,255, filed as application No. PCT/US2018/013650 on Jan. 12, 2018, now Pat. No. 10,975,023.

(60) Provisional application No. 62/446,358, filed on Jan. 13, 2017, provisional application No. 62/490,592, filed on Apr. 26, 2017.

(51) Int. Cl.
| | |
|---|---|
| *C07C 275/20* | (2006.01) |
| *A61P 29/00* | (2006.01) |
| *A61K 9/00* | (2006.01) |
| *C07C 233/47* | (2006.01) |
| *C07D 205/04* | (2006.01) |
| *C07D 207/16* | (2006.01) |
| *C07D 213/80* | (2006.01) |
| *C07D 221/00* | (2006.01) |
| *C07D 239/42* | (2006.01) |
| *C07D 241/28* | (2006.01) |

(52) U.S. Cl.
CPC .......... *C07C 275/20* (2013.01); *A61K 9/0014* (2013.01); *A61P 29/00* (2018.01); *C07C 233/47* (2013.01); *C07D 205/04* (2013.01); *C07D 207/16* (2013.01); *C07D 213/80* (2013.01); *C07D 221/00* (2013.01); *C07D 239/42* (2013.01); *C07D 241/28* (2013.01)

(58) Field of Classification Search
CPC ..... C07C 275/20; C07C 233/47; A61P 29/00; A61K 9/0014; C07D 205/04; C07D 207/16; C07D 213/80; C07D 221/00; C07D 239/42; C07D 241/28
USPC ..................................... 514/210.17
See application file for complete search history.

(56) References Cited

U.S. PATENT DOCUMENTS

| | | | |
|---|---|---|---|
| 5,482,710 A | 1/1996 | Slavtcheff et al. | |
| 10,975,023 B2* | 4/2021 | Voronkov | C07C 275/20 |
| 2009/0170917 A1 | 7/2009 | Lee et al. | |
| 2011/0053901 A1 | 3/2011 | Lee et al. | |
| 2016/0361283 A1 | 12/2016 | Stock et al. | |

FOREIGN PATENT DOCUMENTS

| | | |
|---|---|---|
| EP | 3075248 A1 | 10/2016 |
| WO | 2010/056778 A1 | 5/2010 |
| WO | 2010/090845 A1 | 8/2010 |

OTHER PUBLICATIONS

International Search Report, Apr. 4, 2018, in international application No. PCT/US2018/013650.
Written Opinion, Apr. 4, 2018, in international application No. PCT/US2018/013650.

* cited by examiner

*Primary Examiner* — Kristin A Vajda
(74) *Attorney, Agent, or Firm* — Kim IP Law Group LLC

(57) ABSTRACT

The present invention provides compounds useful in treating or preventing inflammation, acne, bacterial conditions and promoting the appearance of healthy skin and compositions including these compounds.

20 Claims, No Drawings

COMPOUNDS AND METHODS OF USE

REFERENCE TO RELATED APPLICATIONS

This application is a continuation of U.S. patent application Ser. No. 16/469,255, filed Jun. 13, 2019, which claims benefit to International Application No. PCT/US2018/013650 filed on Jan. 12, 2018, which claims the benefit of U.S. Application Ser. No. 62/446,358 filed on Jan. 13, 2017, and U.S. Application Ser. No. 62/490,592, filed Apr. 26, 2017, each of these applications being hereby incorporated herein by reference in their entirety as if it were part of the present disclosure.

BACKGROUND

There remains a need for novel treatment of inflammation, including, but not limited to, inflammation associated with skin diseases and disorders (e.g., rosacea, atopic dermatitis, seborrheic dermatitis, psoriasis). There also remains a need to kill, inactivate, decolonize and/or inhibit the growth of bacteria in a subject. There also remains a need for novel treatment of acne and for the general promotion of healthy looking skin.

SUMMARY

The present invention also provides compositions containing compounds described herein, methods of preparing such compounds and/or compositions, and methods of using such compounds and/or compositions.

In some embodiments, the present invention provides compositions for treating or preventing inflammation comprising at least one presently disclosed compound, a carrier and optionally an additional active ingredient.

In some embodiments, topical compositions for treating or preventing a skin disease or condition are provided, comprising at least one compound of the present invention, a carrier and optionally an additional active ingredient, formulated for topical administration. In certain embodiments, provided herein are topical compositions for promoting healthy skin in a subject comprising at least one presently disclosed compound, a carrier and, optionally, an additional active ingredient.

In some embodiments, the present invention provides uses of provided compounds and/or compositions in the treatment of inflammation, such as skin inflammation. In certain embodiments, the present invention provides uses of provided compounds and/or compositions in the treatment of diseases that may benefit from inhibition of infiltration and activation of inflammatory cells (e.g. neutrophils, lymphocytes, monocytes, mast cells), and/or inhibition of expression and activation of cell surface adhesion molecules (e.g. VCAM-1 and ICAM-1) in endothelial and inflammatory cells. In some embodiments, such includes treating or lessening the severity of inflammatory diseases or disorders selected from inflammation (acute or chronic), inflammation associated with spinal cord injury to promote nerve regeneration, inhibition of rejection of genetically engineered cells by the immune system during in vivo gene therapy, asthma, autoimmune diseases, and chronic obstructive pulmonary disease (COPD) (e.g., emphysema, chronic bronchitis and small airways disease, etc.), inflammatory responses of the immune system, skin diseases (e.g., reducing acute skin irritation for patients suffering from rosacea, atopic dermatitis, seborrheic dermatitis, psoriasis), irritable bowel syndrome (e.g., Crohn's disease and ulcerative colitis, etc.), neurodegenerative disorders (e.g., Parkinson's disease, Alzheimer's disease, Huntington's disease, Dementia pugilistica, Pick's disease, Guam parkinsonism dementia complex, Fronto-temporal dementia, Cortico-basal degeneration, Pallido-pontal-nigral degeneration, Progressive supranuclear palsy, Dementia with Lewy bodies (DLB), and multiple system atrophy (MSA)).

In some embodiments, the present invention provides methods for treating or preventing diseases in a subject that may benefit from the modulation of levels of inflammatory mediators such as cytokines comprising administering the presently disclosed compounds and/or compositions containing one or more of the presently disclosed compounds. In certain embodiments, the present invention provides methods for treating or preventing diseases in a subject that may benefit from the inhibition of infiltration and accumulation of helper-T lymphocytes comprising administering the presently disclosed compounds and/or compositions containing one or more of the presently disclosed compounds. In certain embodiments, the present invention provides methods for treating or preventing diseases in a subject that may benefit from the inhibition of ICMT comprising administering the presently disclosed compounds and/or compositions containing one or more of the presently disclosed compounds. In certain embodiments, the present invention provides methods for treating or preventing diseases in a subject that may benefit from inhibition of oxidative burst response from neutrophils comprising administering the presently disclosed compounds and/or compositions containing one or more of the presently disclosed compounds.

In some embodiments, provided herein are methods for treating or preventing skin conditions (e.g., acne or atopic dermatitis), said methods comprising the step of topically applying onto a surface of a subject, including a human, in need thereof, an effective amount of at least one presently disclosed compound of the present invention. In certain embodiments, provided herein are methods of promoting healthy skin, said methods comprising the step of topically applying onto a surface of a subject, including a human, in need thereof, an effective amount of at least one presently disclosed compound.

In certain embodiments, the present invention provides methods for treating or preventing inflammation in a subject, methods comprising the step of administering an effective amount of at least one presently disclosed compound.

The present invention, provides, inter alia, methods to kill, inactivate, decolonize and/or inhibit the growth of bacteria on a surface. In some embodiments, the present invention provides methods to treat, prevent or ameliorate the symptoms of epithelial-related conditions, caused or aggravated by bacteria in a subject in need thereof.

In some embodiments, the present invention provides methods to treat, prevent and/or ameliorate symptoms of inflammation associated with epithelial-related conditions caused or aggravated by bacteria said methods comprising the step of administering to a subject (e.g., topically applying onto a surface of a subject, including a human) in need thereof, an effective amount of at least one presently disclosed compound of the present invention. In some embodiments, epithelial-related conditions caused or aggravated by bacteria include skin conditions, or respiratory conditions, or nasal conditions, or ocular conditions, or oral conditions. In some embodiments, epithelial-related conditions caused or aggravated by bacteria include conditions of the external ear. In some embodiments, epithelial-related conditions caused or aggravated by bacteria include vaginal conditions. In some embodiments, epithelial-related conditions caused or aggravated by bacteria include genitourinary conditions, or rectal conditions.

DETAILED DESCRIPTION

Definitions

"Anti-bacterial agent": As used herein, the term "anti-bacterial agent" refers to an agent that inhibits the growth of a bacterium or kills a bacterium or results in bacterial decolonization of a surface. In some embodiments, the anti-bacterial agent can have bactericidal effect. In some embodiments, the anti-bacterial agent can have bacteristatic effect. In some embodiments, the anti-bacterial agent can have both bactericidal and bacteristatic effects. As used herein, the term "anti-bacterial agent" refers to both an antibacterial compound or pharmaceutically acceptable salts thereof.

"Acyl": As used herein, the term "acyl" refers to a radical formed from an organic acid by removal of a hydroxyl group.

"Additional active ingredient": As used herein, the phrase "additional active ingredient" refers to an agent, other than a presently disclosed compound that exerts a pharmacological, dermatological or any other beneficial activity. It is to be understood that "other beneficial activity" may be one that is only perceived as such by the subject using the inventive compositions. Typically, an additional active ingredient, as that term is used herein, refers to a pharmaceutically active agent that is administered in combination with a compound of the present invention.

"Aliphatic": The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, cycloalkynyl moieties. Thus, as used herein, the term "alkyl" includes straight, branched and cyclic alkyl groups (see below). An analogous convention applies to other generic terms such as "alkenyl", "alkynyl", and the like. Furthermore, as used herein, the terms "alkyl", "alkenyl", "alkynyl", and the like encompass both substituted and unsubstituted groups. In some embodiments, an aliphatic group contains 1-25 aliphatic carbon atoms. In some embodiments, an aliphatic group contains from 1 to 25, from 1 to 24, from 1 to 23, from 1 to 22, from 1 to 21, from 1 to 20, from 1 to 19, from 1 to 18, from 1 to 17, from 1 to 16, from 1 to 15, from 1 to 14, from 1 to 13, from 1 to 12, from 1 to 11, from 1 to 10, from 1 to 9, from 1 to 8, from 1 to 7, from 1 to 6, from 1 to 5, from 1 to 4, from 1 to 3, from 1 to 2, from 2 to 3, or 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, 20 to 21, 21 to 22, 22 to 23, 23 to 24, or 24 to 25 aliphatic carbon atoms. In certain embodiments, as used herein, "lower alkyl" is used to indicate those alkyl groups (cyclic, acyclic, substituted, unsubstituted, branched, or unbranched) having 1-6 carbon atoms. In some embodiments, wherein a portion of a term such as alkyl, alkenyl, alkynyl, cycloalkyl, cycloalkenyl, cycloalkynyl is used within a different generic term (e.g., dialkylamino, alkoxy, alkylthio, alkylamino), then it is understood that an analogous convention applies with respect to the number of carbon atoms present.

"Alkenyl": As used herein, the term "alkenyl" denotes a substituted or unsubstituted, monovalent group derived from a straight- or branched-chain hydrocarbon moiety containing at least one carbon-carbon double bond by removal of a single hydrogen atom. In some embodiments, the alkenyl group contains 1-25 aliphatic carbon atoms. In certain embodiments, an alkenyl group employed in the invention contains 10-25 carbon atoms. In certain embodiments, an alkenyl group employed in the invention contains 10-20 carbon atoms. In certain embodiments, an alkenyl group employed in the invention contains 10-15 carbon atoms. In certain embodiments, an alkenyl group employed contains 10 carbon atoms. In certain embodiments, an alkenyl group employed contains 15 carbon atoms. In certain embodiments, an alkenyl group employed contains 20 carbon atoms. Alkenyl groups include, for example, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, polyunsaturated alkenes including octadec-9, 12-dienyl, octadec-9,12,15-trienyl, eicos-5,8,11,14-tetraenyl, farnesyl, geranyl, and geranylgeranyl, C-20 phytyl, and the like.

"Alkenylene": The term "alkenylene" refers to a bivalent, substituted or unsubstituted, alkenyl group. A substituted alkenylene chain is a polymethylene group containing at least one double bond in which one or more hydrogen atoms are replaced with a substituent. Suitable substituents include those described herein for a substituted aliphatic group.

"Alkyl": As used herein, the term "alkyl" means substituted or unsubstituted, saturated, straight- or branched-chain hydrocarbon radicals derived from an aliphatic moiety by removal of a single hydrogen atom. In some embodiments, the alkyl group contains 1-25 aliphatic carbon atoms. In certain embodiments, an alkyl group employed in the invention contains 10-25 carbon atoms. In certain embodiments, an alkyl group employed in the invention contains 10-20 carbon atoms. In certain embodiments, an alkyl group employed in the invention contains 15-20 carbon atoms. In certain embodiments, an alkyl group employed contains 10 carbon atoms. In certain embodiments, an alkyl group employed contains 15 carbon atoms. In certain embodiments, an alkyl group employed contains 20 carbon atoms. In certain embodiments, an alkyl group employed in the invention contains 1-3 carbon atoms. In certain embodiments, an alkyl group employed contains 1-2 carbon atoms. In certain embodiments, an alkyl group contains 1 carbon atom. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, tridecyl, tetradecyl, pentadecyl, hexadecyl, heptadecyl, octadecyl, nonadecyl, eicosyl, heneicosyl, docosyl, tricosyl, teteracosyl, pentacosyl, and the like.

"Alkylamino": The term "alkylamino" refers to a substituted or unsubstituted group having the structure —NHR', wherein R' is aliphatic, as defined herein. In certain embodiments, the aliphatic group contains 1-20 aliphatic carbon atoms. In some embodiments, the aliphatic group contains 1-10 aliphatic carbon atoms. In some embodiments, the aliphatic group employed in the invention contains 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylanino groups include, but are not limited to, methylanino, ethylamino, n-propylamino, iso-propylamino, cyclopropylamino, n-butylamino, tert-butylamino, neopentylamino, n-pentylamino, hexylamino, cyclohexylamino, and the like.

"Alkylene": The term "alkylene" refers to a bivalent substituted or unsubstituted alkyl group. Unless otherwise specified, the alkylene group contains 1-25 aliphatic carbon atoms. An "alkylene chain" is a polymethylene group, i.e., —(CH$_2$)$_n$—, wherein n is a positive integer, preferably from 1 to 6, from 1 to 5, from 1 to 4, from 1 to 3, from 1 to 2, from 2 to 3, from 3 to 4, from 4 to 5, or from 5 to 6. A substituted alkylene chain is a polymethylene group in which one or more methylene hydrogen atoms are replaced with a substituent. Suitable substituents include those described herein for a substituted aliphatic group.

"Alkynyl": As used herein, the term "alkynyl" denotes a substituted or unsubstituted monovalent group derived from a straight- or branched-chain hydrocarbon moiety containing at least one carbon-carbon triple bond by removal of a single hydrogen atom. In certain embodiments, an alkynyl group employed in the invention contains 10-25 carbon atoms. In certain embodiments, an alkynyl group employed in the invention contains 10-20 carbon atoms. In certain embodiments, an alkynyl group employed contains 10 carbon atoms. In certain embodiments, an alkynyl group employed contains 15 carbon atoms. In certain embodiments, an alkynyl group employed contains 20 carbon atoms. In certain embodiments, an alkynyl group employed in the invention contains 2-3 carbon atoms. In certain embodiments, an alkynyl group employed contains 2 carbon atoms. In certain embodiments, an alkynyl group employed contains 3 carbon atoms. Representative alkynyl groups include, but are not limited to, ethynyl, 2-propynyl (propargyl), 1-propynyl, and the like.

"Alkoxy", or "Alkylthio": The term "alkoxy", or "alkylthio" as used herein refers to a substituted or unsubstituted alkyl group, as previously defined, attached to the parent molecule through an oxygen atom or through a sulfur atom. In certain embodiments, the "alk" or "alkyl" portion of an "alkoxy" or "alkylthio" group contains 1-10 aliphatic carbon atoms. In yet other embodiments, the "alk" or "alkyl" portion of an "alkoxy" or "alkylthio" group employed in the present invention contains 1-8 aliphatic carbon atoms. In still other embodiments, the "alk" or "alkyl" portion of an "alkoxy" or "alkylthio" group contains 1-6 aliphatic carbon atoms. In yet other embodiments, the "alk" or "alkyl" portion of an "alkoxy" or "alkylthio" group contains 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl groups include, but are not limited to, methylthio, ethylthio, propylthio, isopropylthio, n-butylthio, and the like.

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal. In some embodiments, the term animal is used to refer to veterinary animals (e.g., fowl, cows, pigs, horses, etc.).

"Aralkylene" refers to a divalent group of formula —R$^a$—Ar$^a$— where R$^a$ is an "alkylene" as defined herein, and Ar$^a$ is an "arylene" as defined herein (i.e., an alkylene is bonded to an arylene).

"Anti-dandruff agent": As used herein, the term "anti-dandruff agent" is an agent that reduces, eliminates or prevents a scurf from forming on skin, especially of the scalp, that comes off in small white or grayish scales. Exemplary anti-dandruff ingredients usable in context of the present invention include, without limitation, butoconazole, climbazole, coal tar, clotrimazole, dichlorophenyl imidazolodioxalan, imidazoles (e.g., fluconazole, ketoconazole, itraconazole, miconazole, miconazolenitrite, povidone-iodine, sulconazole, tioconazole), salicylic acid, selenium sulfide, shale oil and the like (e.g., sulfonated shale oil), sulfur, zinc pyrithione, and the like, and any possible stereo isomers thereof such as anthralin, piroctone olamine (Octopirox), selenium sulfide, and ciclopiroxolamine, and combinations thereof.

"Antihistamine agent": As used herein, the term "antihistamine agent" is an agent that counteracts histamine in the body and that is used for treating allergic reactions (such as hay fever) and cold symptoms. Non-limiting examples of antihistamines usable in context of the present invention include astenizole, brompheniranine, chlorpheniranine, clemastine, dexchlorpheniranine, diphenhydramine, loratadine, piperidines, piperazines, promethazine, terfenadine and tripolidine and combinations thereof.

"Anti-irritant": The term "anti-irritant", as used herein, is an agent that prevents or reduces soreness, roughness, or inflammation of a bodily part (e.g., skin). Presently known anti-irritants can be divided into water-soluble anti-irritants and water-insoluble anti-irritants. Representative examples of such compositions are described, for example, in U.S. Pat. No. 5,482,710, which is herein incorporated by reference. Suitable anti-irritants that can be used in the context of the present invention include, for example, steroidal and non-steroidal anti-inflammatory agents or other materials such as allantoin, aloe vera, alpha-bisabolol, caffeine, chamomile, cola nitida extract, green tea extract, glycyrrhizic acid, licorice extract, tea tree oil, or other xanthines, and combinations thereof.

"Anti-oxidant agent": As used herein, the term "anti-oxidant agent" is an agent that inhibits oxidation or reactions promoted by oxygen or peroxides. Non-limiting examples of anti-oxidants that are usable in the context of the present invention include amines (e.g., N,N-diethylhydroxylanine, amino-guanidine), arginine pilolate, ascorbic acid (vitamin C) and its salts, ascorbyl esters of fatty acids, ascorbic acid and the like (e.g., magnesium ascorbyl phosphate, sodium ascorbyl phosphate, ascorbyl sorbate), bioflavonoids, butylated hydroxy benzoic acids and their salts, curcumin, dihydroxy fumaric acid and its salts, gallic acid and its alkyl esters (e.g., propyl gallate, uric acid and its salts and alkyl esters), glycine pidolate, grape skin/seed extracts, 6-hydroxy-2,5,7,8-tetramethylchroman-2-carboxylic acid (commercially available under the tradename Trolox®), lipoic acid, lysine, melanin, methionine, nordihydroguaiaretic acid, proline, rosemary extracts, silymarin, sorbic acid and its salts, sulfhydryl compounds (e.g., glutathione), superoxide dismutase, tea extracts, tocopherol acetate, tocopherol (vitamin E), tocopherol sorbate, and other esters of tocopherol and combinations thereof. In certain non-limiting embodiments, the antioxidant can be selected from one or more of butylated hydroxyanisole, butylated hydroxytoluene, sodium metabisulfite and tert-butylhydroquinone.

"Antipruritic agents": As used herein, the term "antipruritic agent" as used herein, is an agent that reduces, eliminates or prevents itching. Suitable antipruritic agents include, without limitation, methdilazine and trimeprazine, and combinations thereof.

"Anti-skin atrophy actives": As used herein, the term "anti-skin atrophy active" is an agent that is effective in replenishing or rejuvenating the epidermal layer by promoting or maintaining the natural process of desquamation. Examples of antiwrinkle and antiskin atrophy actives which can be used in context of the present invention include alpha-hydroxy acids (e.g. glycolic acid, and lactic acid), lipoic acid, lysophosphatidic acid, phytic acid, retinoic acid, its prodrugs, isomers (e.g., cis and trans) and analogues thereof, salicylic acid and the like, sclerosing agents or sclerosants, skin peel agents (e.g., phenol and the like), sulfur-containing D and L amino acids and the like and related salts, (e.g., N-acetyl derivatives, such as N-acetyl L-cysteine), and thiols (e.g. ethane thiol).

"Anesthetic agents": The term "anesthetic agent" as used herein is an agent that results in a reduction or loss of sensation. Non-limiting examples of anesthetic drugs that are suitable for use in the context of the present invention include pharmaceutically acceptable salts of bupivacaine, chloroprocaine, cocaine, dibucaine, dyclonine, etidocaine, hexylcaine, ketamine, lidocaine, mepivacaine, phenol, pramoxine, procaine, and tetracaine.

"Aryl" and "Heteroaryl": In general, the terms "aryl" and "heteroaryl" refer to substituted or unsubstituted aromatic groups or moieties. In some embodiments, the terms "aryl" and "heteroaryl" may be used in the context of a different moiety name (e.g., "arylalkyl", "aralkylene", "aryloxy", "heteroaryloxy" or "heteroarylalkyl"). In some embodiments, an "aryl" and/or "heteroaryl" refer to stable mono- or polycyclic, heterocyclic, polycyclic, and polyheterocyclic unsaturated moieties wherein at least one ring in the system is aromatic. In some embodiments, an "aryl" and/or "heteroaryl" ring system contains three to seven ring members. In some embodiments, an "aryl" and/or "heteroaryl" contain 3-14 carbon atoms. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. It will be appreciated that aryl and heteroaryl groups can be unsubstituted or substituted, wherein substitution includes replacement of one, two, three, or more of the hydrogen atoms thereon independently with any one or more of the moieties (e.g., "substituents") provided herein.

"Arylene" and "Heteroarylene": The term "arylene" refers to an unsubstituted or substituted divalent group that is carbocyclic and aromatic. In some embodiments, rings in an arylene group are fused to one another. In some embodiments rings in an arylene group are not fused, but are nonetheless connected. In some embodiments, an arylene group includes some fused rings and some connected rings. In some embodiments, an arylene group includes aromatic rings. In some embodiments, an arylene group includes non-aromatic rings. In some embodiments, an arylene group includes some aromatic rings and some non-aromatic rings. In some embodiments, the arylene group has up to 5 rings, up to 4 rings, up to 3 rings, up to 2 rings, or one aromatic ring. For example, the arylene group can be phenylene. Exemplary arylene groups include any of the "aryl" moieties listed herein with the understanding that divalency is required to arrive at a corresponding "arylene" group from an "aryl" group. Exemplary substituents of "arylene" groups include replacement of one, two, three, or more of the hydrogen atoms thereon independently with any one or more of the moieties applicable for "aryl" and "heteroaryl," as defined herein. It will be appreciated by one skilled in the art that a carbon ring atom of an "arylene" can be replaced by one, two or three heteroatoms independently selected from S, O, and N while the remaining ring atoms are carbon, the divalent group being joined to the rest of the molecule via any two ring atoms, to form a "heteroarylene". Exemplary "heteroarylene" groups include any of the "heteroaryl" moieties listed herein with the understanding that divalency is required to arrive at a corresponding "heteroarylene" group from a "heteroaryl" group.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Astringent": As used herein, the term "astringent" is an agent that draws together or constricts body tissues and is effective in stopping the flow of blood or other secretions. In some embodiments, an astringent coagulate blood, and therefore can be used to arrest hemorrhage. In some embodiments, an astringent promotes healing, toughens skin and/or to decreases sweating. In some embodiments astringents are protein precipitants. Typically, astringents have low cell penetrability such that their action is limited to the cell surface and/or interstitial spaces. In some embodiments, astringent action is accompanied by contraction and wrinkling of tissues to which astringents are applied. In some embodiments, application of astringents is accompanied by blanching of recipient tissue. In some embodiments, astringents include one or more agents such as aluminum, bismuth, iron, manganese, zinc. Alternatively, and/or additionally, such agents can be provided in any of a variety of forms including, for example, pharmaceutically acceptable salt forms.

"Carrier": The term "carrier" is used in accordance with its art-understood meaning, to refer to a material that is included in a pharmaceutical composition but does not abrogate the biological activity of pharmaceutically active agent(s) that are also included within the composition. Pharmaceutical carriers are typically of sufficiently high purity and sufficiently low toxicity to render it suitable for administration to the subject being treated. In some embodiments, carriers are inert. In some embodiments, carriers are affirmatively beneficial (e.g., providing pharmaceutical and/or cosmetic benefits). In some embodiments, AFC acts as an acceptable carrier. In some embodiments, the term "carrier" when used in the pharmaceutical context (e.g., pharmaceutically acceptable carrier) means that an agent is present in a composition but does not abrogate the biological activity of another agent(s) present in a composition. In some embodiments, the term "carrier" when used in a cosmetic context (e.g., cosmetically acceptable carrier) means that an agent is present in a composition but does not but does not abrogate the biological activity and/or aesthetic effect of another agent(s) present in a composition. In some embodiments, a cosmetically acceptable carrier is used to topically administer cosmetics with which presently disclosed compounds of the present invention will remain stable and bioavailable. It will be understood that "cosmetically acceptable carriers" and "carriers" as defined herein are similar, if not often identical, in nature. In some embodiments, the term "carrier" when used in a cosmeceutical context (e.g., cosmeceutical carrier) means that an agent is present in a composition but does not abrogate the biological activity and aesthetic effect of another agent(s) present in a composition. Pharmaceutical carriers further, in certain embodiments, maintain the stability and bioavailability of an active agent (i.e. a presently disclosed compound of the present invention). Pharmaceutical carriers can be liquid or solid and are selected with the planned manner of administration in mind, to provide for the desired bulk, consistency, etc., when combined with an active agent and other components of a given composition.

"Caustic agents": As used herein, the term "caustic agent" is an agent that is capable of destroying or eating away epithelial tissue by chemical action. Caustic agents can be used to remove dead skin cells. For example, beta-hydroxy acids, naturally derived acids with a strong kerolytic effect, are useful for problem skin or peeling.

"Chelating Agent": The term "chelating agent" as used herein, is an agent that binds to a metal ion such as calcium ($Ca^{2+}$), magnesium ($Mg^{2+}$) and copper ($Cu^{2+}$), forming a metal complex known as a chelate. In some embodiments, a chelating agent is a ligand. In some embodiments, a chelating agent is an atom. In some embodiments, a chelating agent is an ion. In some embodiments, a pharmaceutical composition may contain a chelating agent (e.g., a mild agent, such as, ethylenediaminetetraacetic acid ("EDTA"), EDTA derivatives, or combinations thereof). In some embodiments, a chelating agent enhances a preservative or preservative system of the composition.

"Colorants": As used herein, the term "colorant" refers to pigments and/or dyes or a combination thereof, that are used to change hair color as cosmetic benefit requires. In some embodiments, pigments included in "colorants" include, but are not limited to, iron oxides, and titanium oxides. In some embodiments, dyes included in "colorants" include D&C approved colorants, FD&C approved colorants, and those approved for use in Europe and Japan. See Marmion, D. M., Handbook of US Colorants for Food, Drugs, Cosmetics, and Medical Devices, 3rd ed, 1991 herein incorporated by reference.

"Compatible": The term "compatible" as used herein means that the components of such a composition are capable of being combined with each other in a manner such that there is no interaction that would substantially reduce the efficacy of the composition under ordinary use conditions.

"Demulcent": As used herein, the term "demulcent" is an agent used to primarily alleviate irritation, particularly mucous membranes or abraded tissues. Exemplary demulcents include acacia, agar, alginates, mucilages, benzoin, carbomer, gelatin, glycerin, gums, hydroxyethyl cellulose, hydroxypropyl cellulose, hydroxypropyl methylcellulose, hydrogels, dextrins, starches, certain sugars, and polymeric polyhydric glycols, propylene glycol, sodium alginate, tragacanth, and combinations thereof.

"Deodorant agent": As used herein, the term "deodorant agent" refers to a substance for inhibiting or masking perspiration or other bodily odors. Representative examples of deodorant agents that are usable in the context of the present invention include, without limitation, quaternary ammonium compounds such as benzethonium chloride, cetyl pyridinium chloride, cetyl-trimethylammonium bromide, diisobutyl phenoxy ethoxy ethyl dimethyl benzyl ammonium chloride, lauroyl sarcosine, sodium aluminum chlorohydroxy lactate, sodium N-lauryl sarcosine, sodium N-palmityl sarcosine, N-myristoyl glycine, potassium N-lauryl sarcosine, stearyl, trimethyl ammonium chloride, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts (e.g. as the alkali metal carbonates and bicarbonates, ammonium and tetraalkylammonium carbonates and bicarbonates, especially the sodium and potassium salts) or combination thereof.

"Dialkylamino": The term "dialkylamino" refers to a group having the structure —NRR', wherein R and R' are each an aliphatic group, as defined herein. R and R' may be the same or different in a dialkyamino moiety. In certain embodiments, the aliphatic group contains 1-20 aliphatic carbon atoms. In some embodiments, the aliphatic group contains 1-10 aliphatic carbon atoms. In yet other embodiments, the aliphatic groups employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of dialkylamino groups include, but are not limited to, dimethylamino, methyl ethylamino, diethylamino, methylpropylamino, di (n-propyl) amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

"Effective amount": In general, the "effective amount" of an active agent (e.g., a therapeutic agent, composition, and/or formulation) refers to an amount sufficient to elicit the desired biological response. In some embodiments, a therapeutically effective amount of a substance is an amount that is sufficient, when administered to a subject suffering from or susceptible to a disease, disorder, and/or condition, to treat, diagnose, prevent, and/or delay the onset of one or more symptoms of the disease, disorder, and/or condition. As will be appreciated by those of ordinary skill in this art, and effective amount of a substance may vary depending on such factors as the desired biological endpoint, the substance to be delivered, the pharmacokinetics of the compound, the target cell or tissue, the disease being treated, the mode of administration, and the patient, etc. For example, the effective amount of a composition and/or formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. Those of ordinary skill in the art will appreciate that, commonly, a therapeutically effective amount will be administered over a series of individual doses. In some embodiments, the term "effective amount" when used in a pharmaceutical context (e.g., pharmaceutically effective amount) means that an agent is present in an amount sufficient to achieve a desired therapeutic effect. In some embodiments, the term "effective amount" when used in a cosmetic context (e.g., cosmetically effective amount) means that an agent is present in an amount sufficient to achieve an aesthetic effect. In some embodiments, the term "effective amount" when used in a cosmeceutical context (e.g., cosmeceutically effective amount) means that an agent is present in an amount sufficient to achieve a therapeutic and/or aesthetic effect.

"Emollients": As used herein, the term "emollients" refers to an agent that increases tissue moisture content, thereby rendering skin softer and more pliable. Increased moisture content in the skin can be achieved by preventing water loss with an occlusive water-immiscible barrier, by increasing the water-holding capacity in the skin with humectants, or by altering the desquamation of the outermost skin layer, the stratum corneum. In some embodiments, "emollients" are typically bland, fatty or oleaginous materials which can be applied locally, particularly to the skin. Useful emollients include cetyl alcohol, glycerin, hydrophilic petrolatum, isopropyl myristate, lanolin, mineral oil, myristyl alcohol, oleyl alcohol, paraffin, petrolatum, spermaceti, vegetable oils, waxes, white ointment, white petroleum, yellow ointment or combinations thereof.

"Emulsifier": The term "emulsifier" as used herein promotes formation and stabilization of an emulsion. Suitable emulsifiers may be finely divided solids, natural materials, or synthetic materials. Natural emulsifying agents may be derived from either animal or vegetable sources. Those from animal sources include casein, cholesterol, egg yolk, gelatin, or wool fat or combinations thereof. Those from vegetable sources include acacia, chondrus, pectin or tragacanth or combinations thereof. Vegetable sources specifically from cellulose derivatives include carboxymethyl cellulose and methyl cellulose to increase the viscosity. Finely divided emulsifiers include aluminum hydroxide, bentonite, magnesium hydroxide, or magnesium trisylicate. Synthetic agents include anionic, cationic or nonionic agents, and include benzalkonium chloride, polyethylene glycol 400 monostearate, sodium lauryl sulfate, or combinations thereof.

"Enantiomerically enriched" and "Enantioenriched": As used herein, the terms "enantiomerically enriched" and "enantioenriched" denote that one enantiomer is enriched with respect to other enantiomers of the same compound in a composition. For example, when a compound is substantially in the R-form or the S-form with respect to a particular chiral center, the compound may be considered to have an enantiomeric excess (ee) for that form. In some embodiments, a composition is considered "enriched" when one enantiomer is present in at least 75% ee in the composition. In certain embodiments, the terms denote that one enantiomer is present in at least 80% ee, 85% ee, 90% ee, 95% ee, 97.5% ee, or more. In some embodiments, a composition is considered "enantiomerically pure" or "enantiopure" when one enantiomer is present with an ee of at least about 90%, with respect to other enantiomers. In some embodiments, a composition is considered "enantiomerically pure" or "enantiopure" when one enantiomer is present with an ee of at least about 95%, with respect to other enantiomer(s) present in the composition. In some embodiments, a composition is considered "enantiomerically pure" or "enantiopure" when one enantiomer is present with an ee of at least about 97.5%, with respect to other enantiomer(s) present in the composition. In some embodiments, a composition is considered "enantiomerically pure" or "enantiopure" when one enantiomer is present with an ee of at least about 99%, with respect to other enantiomer(s) present in the composition.

"Fragrance": As used herein, the term "fragrance" refers to an agent having a pleasant aroma. Suitable fragrances include, but are not limited to, camphor synthetic, chamomile, clove oil, eucalyptus oil, lavender, peppermint oil, and the like.

"G-protein mediated condition": The term "G-protein mediated condition", as used herein means any disease or other deleterious condition for which the appearance, incidence, and/or severity of one or more symptoms correlates with changes in a G-protein signaling cascade. In some embodiments, one or more symptoms of the disease or condition is caused by a defect or alteration in G-protein signaling.

"Hair Conditioning Agents": As used herein, the term "hair conditioning agent" refers to an agent that is suitable for use in conditioning hair (e.g., so as to further improve the condition of the hair). In some embodiments, representative hair conditioning agents include, for example, one or more alkoxylated alcohols, alkoxylated amides, alkoxylated carboxylic acids, cationic surfactants, collagens, dimethicone polyols, esters (e.g., glyceryl esters), halogenated quaternary ammonium compounds, keratins, modified silicones, proteins, polymeric ethers, quaternary ammonium compounds, or sorbitan derivatives, or combinations thereof.

"Halo" and "Halogen": The terms "halo" and "halogen" as used herein refer to an atom selected from fluorine, chlorine, bromine, and iodine.

"Heteroaliphatic": The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties (e.g., "substituents") described herein.

"Heteroatom": As used herein, the term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR_x$ (as in N-substituted pyrrolidinyl)).

"Heterocycle" or "Heterocyclyl": As used herein, the terms "heterocycle", "heterocyclyl", "heterocyclic radical", and "heterocyclic ring" are used interchangeably and refer to a stable 3- to 7-membered monocyclic or 7-10-membered bicyclic heterocyclic moiety that is either saturated or partially unsaturated, and having, in addition to carbon atoms, one or more, preferably one to four heteroatoms independently selected from nitrogen, oxygen, or sulfur. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or $NR_x$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. In certain embodiments, one or more carbon atoms may be substituted with an oxo group in the heterocyclyl ring. Examples of such groups include, without limitation, an isoindolin-1,3-dione moiety. A heterocyclyl group may be mono- or bicyclic. The term "heterocyclylalkyl" refers to an alkyl group substituted by a heterocyclyl, wherein the alkyl and heterocyclyl portions independently are optionally substituted.

"Hormone": As used herein, the term "hormone" refers to natural substances produced by organs of the body that travel by blood to trigger activity in other locations or their synthetic analogs. Suitable hormones for use in the context of the present invention include, but are not limited to, calciferol (Vitamin $D_3$) and its products, androgens, estrogens and progesterones.

"Hydrocarbon": The term "hydrocarbon", as used herein, refers to any chemical group comprising hydrogen and carbon. In some embodiments, a hydrocarbon consists of hydrogen and carbon. A hydrocarbon may be substituted or unsubstituted. A hydrocarbon may be unsaturated, saturated, branched, unbranched, cyclic, or polycyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions. As used herein, a "bivalent hydrocarbon" refers to alkylene, alkenylene, or alkynylene, etc.

"Hypopigmenting agents": As used herein, the term "hypopigmenting agents" refers to substances capable of depigmenting the skin. Suitable hypopigmenting agents include hydroquinones, mequinol, and various protease inhibitors including serine protease inhibitors, active soy and retinoic acid.

"In combination": As used herein, the phrase "in combination" refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in the subject's body, they are considered to be administered "in combination".

"Independently selected": The term "independently selected" is used herein to indicate that the referenced groups can be identical or different.

"Irritant": As used herein, the term "irritant" is a material that acts locally on the skin to induce, based on irritant concentration, hyperemia, inflammation, and desiccation. Irritant agents include, but are not limited to, alcohol, aromatic ammonia spirits, benzoin tincture, camphor capsicum, and coal tar extracts. In some embodiments, the irritant is a rubefacient.

"Modulate": The term "modulate" refers to change in a parameter (e.g., a change in a binding interaction or an activity, etc.). Modulation can refer to an increase or a decrease in the parameter (e.g., an increase or decrease in binding, an increase or decrease in activity, etc.).

"Modulator": The term "modulator" refers to an agent that alters level and/or activity of its target in an inflammatory pathway. In some embodiments, a modulator alters interaction between a protein in an inflammatory pathway and one or more other entities. In some embodiments, a modulator alters interaction between a protein in an inflammatory pathway and a substrate. Determination of whether an agent is a modulator can be performed directly or indirectly. Determination of whether an agent modulates an interaction can be performed directly, e.g., using an assay that detects the interaction between a protein in an inflammatory pathway and a substrate. Determination of whether an agent modulates an interaction can be performed with a technique that indirectly detects modulation, e.g., a technique that detects a biological activity that is downstream of, and dependent on, the protein-substrate interaction. In certain embodiments, inflammatory pathways are G-protein-mediated (e.g., purinergic receptor-mediated). In certain embodiments, inflammatory pathways are non-G-protein-mediated (e.g., PPAR-mediated, Toll-like receptor-mediated, and TNF-alpha receptor-mediated).

"Moisturizing agent": As used herein a "moisturizing agent" is a substance that adds or restores moisture to the skin. Representative examples of moisturizing or humectant agents that are usable in the present invention include, without limitation, acetamide monoethanolamine urazole, aloe vera in any of its variety of forms (e.g., aloe vera gel), allantoin, guanidine, glycolic acid and glycolate salts (e.g. ammonium salt and quaternary alkyl ammonium salt), hyaluronic acid, lactamide monoethanolamine, polyethylene glycols, polyhydroxy alcohols (e.g., sorbitol, glycerol, hexanetriol, propylene glycol, butylene glycol, hexylene glycol and the like), sugars and starches, sugar and starch derivatives (e.g., alkoxylated glucose), and any combination thereof.

"Non-steroidal anti-inflammatory agents": As used herein, the term "non-steroidal anti-inflammatory agents" refers to a large group of agents that are aspirin-like in their action, including acetaminophen, Advil®, Aleve®, ibuprofen, naproxen sodium and Tylenol®. Additional examples of non-steroidal anti-inflammatory agents that are usable in the context of the present invention include, without limitation, acetic acid derivatives (e.g., acematacin, clindanac, diclofenac, felbinac, fenclofenac, fentiazac, furofenac, indomethacin, isoxepac, ketorolac, oxepinac, sulindac, tiopinac, tolmetin, zidometacin and zomepirac), benorylate, diflunisal, disalcid, fenamates (e.g., flufenamic, meclofenamic, mefenamic, niflumic and tolfenamic acids), fendosal, oxicams (e.g., CP-14,304, isoxicam, piroxicam, sudoxicarn, and tenoxicam), propionic acid derivatives (e.g., alminoprofen, benoxaprofen, carprofen, fenbufen, fenoprofen, flurbiprofen, ibuprofen, indopropfen, ketoprofen, miroprofen, naproxen, oxaprozin, pirprofen, pranoprofen, suprofen, tiaprofenic and tioxaprofen), pyrazoles (e.g., azapropazone, feprazone, oxyphenbutazone, phenylbutazone and trimethazone), safapryn, solprin, trilisate.

"Partially Unsaturated": As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

"Penetration enhancer" and "pharmaceutically acceptable penetration enhancer": The term "penetration enhancer" and "pharmaceutically acceptable penetration enhancer" as used herein is a non-toxic agent that improves bioavailability of a topical composition. In some embodiments, a penetration enhancer is known to accelerate the delivery of a substance through the skin (e.g., disrupting the barrier function of the skin without compromising its barrier effects on microorganisms and toxins). Typically, a penetration enhancer is selected to be non-toxic to skin of the intended recipient (e.g., human). A penetration enhancer is also desirably compatible with any pharmaceutically active agent with which it is administered. Representative penetration enhancers include, for example, and without limitation, such agents as 1-substituted azacycloheptane-2-ones (e.g., 1-n-dodecyl-cyclazacycloheptan-2-one, available under the trademark Azone® from Whitby Research Incorporated, Richmond, Va.), dipolar-aprotic solvents (e.g., N,N-dimethylacetamide ("DMA"), decylmethylsulfoxide ("$C_{10}$ MSO"), dimethyl formamide ("DMF"), dimethylsulfoxide ("DMSO") and N-methyl-2-pyrrolidone ("NMP")), phospholipids (e.g., allantoin, fatty acid alcohols, lecithin, alcohols including glycerols such as polyethylene glycol monolaurate ("PGML"), glycerol monolaurate ("GML"), urazole, and the like). Penetration enhancer also can be a vegetable oil, such as, but not limited to, corn oil, cottonseed oil, safflower oil, and olive oil. Additional penetration enhancers generally can be found in Remington: The Science and Practice of Pharmacy, 20$^{th}$ ed. (Gennaro, A. R., et al., eds.) Lippincott Williams & Wilkins: Philadelphia (2000), which is incorporated herein by reference.

"pH adjusting agent": As used herein, the term "pH adjusting agent" as used herein is an agent that imparts suitable pH characteristics to compositions provided herein, (e.g., a substantially neutral pH), the pH of which depends on the specific utilization of the composition. In some embodiments, as the pH of skin is 5.5, it may be desirable to formulate compositions for topical skin application (to avoid irritation) having a pH value in a range of from about 4.0 to about 7.0, or in a range of from about 5.0 and 6.0, or about 5.5, or substantially 5.5. Suitable pH adjusting agents include, for example, but are not limited to, one or more adipic acids, buffers, citric acids, calcium hydroxides, glycines, magnesium aluminometasilicates, or combinations thereof.

"Pharmaceutically acceptable salt": The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 66: 1-19, 1977; incorporated herein by reference. Such salts can be prepared in situ during the final isolation and purification of the compounds of the invention, or separately (e.g., by reacting the free base functionality with a suitable organic or inorganic acid). Alternatively, or additionally, salts may form during formulation of a compound. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, disodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

"Pharmaceutically acceptable ester": The term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include formates, acetates, propionates, butyrates, acrylates, and ethylsuccinates. In certain embodiments, the esters are cleaved by enzymes such as esterases.

"Pharmaceutically acceptable prodrugs": The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are transformed in vivo to yield the parent compound of the above formula, for example by hydrolysis in blood. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. Various forms of prodrugs are known in the art, for example as discussed in Bundgaard (ed.), *Design of Prodrugs*, Elsevier (1985); Widder et al. (ed.), *Methods in Enzymology*, vol. 4, Academic Press (1985); Kgrogsgaard-Larsen et al. (ed.); *"Design and Application of Prodrugs", Textbook of Drug Design and Development*, Chapter 5, 113-191 (1991); Bundgaard et al., *Journal of Drug Delivery Reviews*, 8:1-38 (1992); Bundgaard et al., *J. Pharmaceutical Sciences*, 77:285 et seq. (1988); and Higuchi and Stella (eds.), Prodrugs as *Novel Drug Delivery Systems*, American Chemical Society (1975).

"Preservative": As used herein, the term "preservative" has its art-understood meaning and refers to an agent that protects against undesirable chemical modifications of one or more components in a composition (e.g., protection against an undesirable chemical modification of an active ingredient). Suitable preservatives for use in the compositions of the present invention include, but are not limited to, one or more alkanols, disodium EDTA, EDTA salts, EDTA fatty acid conjugates, isothioazolinone, parabens such as methylparaben and propylparaben, polypropylene glycols, sorbates, urea derivatives such as diazolindinyl urea, or combinations thereof.

"Propellant": As used herein, the term "propellant" refers to an agent that propels the delivery of a composition in, e.g., a vaporized, aerosol nebulized, or spray form. Propellants often are used in metered-dose inhalers for the treatment of asthma and other respiratory disorders and for systemic treatments such as insulin for diabetes. Propellants also are used, for example, in nasal inhalers for treatment of allergic rhinitis, topical sprays, oral sprays, and other aerosol applications. An example of such propellants, without limitation, are the Dymel® pharmaceutical propellants manufactured by DuPont®. (Wilmington, Del.).

"Protective": As used herein, the term "protective" refers to an agent that isolates exposed surface of skin or other membrane from harmful or annoying stimuli. Exemplary protectives include dusting powders, adsorbents, mechanical protective agents, and plasters. Mechanical protectives are generally either collodions or plasters, and include, for example aluminum hydroxide gel, collodium, dimethicone, petrolatum gauze, absorbable gelatin film, absorbable gelatin sponge, zinc gelatin, kaolin, lanolin, anhydrous lanolin, mineral oil, mineral oil emulsion, mineral oil light, olive oil, peanut oil, petrolatum, silicones, hydrocolloids and the like. In some embodiments, a protective includes an adherent, continuous film that may be flexible or semi-rigid depending on the materials and the formulations as well as the manner in which they are applied. In some embodiments, a "protective" may be a "demulscent" as described herein.

"Racemic": As used herein, a racemic mixture means about 50% of one enantiomer and about 50% of its corresponding enantiomer relative to all chiral centers in a molecule. Compounds of the present invention may encompass enantiomerically pure, enantiomerically enriched, and racemic mixtures.

"Rubefacient": As used herein, the term "rubefacient" is an agent that induces hyperemia, wherein hyperemia means an increased amount of blood in a body part or organ. Rubefaction, which is induced by rubefacients, results from increased circulation to an injured area and is accompanied by a feeling of comfort, warmth, itching and hyperesthesia.

"Skin Irritant": As used herein, the term "skin irritant" refers to a compound that, when applied to skin or a skin equivalents, elicits a cellular response characterized by the expression of an "irritant responsive gene." Examples of known skin irritants include, but are not limited to, sodium dodecyl sulfate ("SDS"), calcipotriol, and trans-retinoic acid. The term "skin irritant" is also intended to encompass unknown or suspected irritants, including but not limited to, those containing in some pharmaceuticals, cosmetics, and consumer products.

"Solubilizing agent": As used herein, the term "solubilizing agent" are those substances that enable solutes to dissolve. Representative examples of solubilizing agents that are usable in the context of the present invention include, without limitation, complex-forming solubilizers (e.g., citric acid, ethylenediamine-tetraacetate, sodium meta-phosphate, succinic acid, urea, cyclodextrin, polyvinylpyrrolidone, diethylammonium-ortho-benzoate, etc.), n-alkyl amine n-oxides, micelle-forming solubilizers (e.g., TWEEN® including TWEEN 80®), organic solvents (e.g., acetone, phospholipids and cyclodextrins), polyoxamers, polyoxyethylene n-alkyl ethers, and polyoxyethylene sorbitan fatty acid ester.

"Steroidal anti-inflammatory agent": As used herein, the term "steroidal anti-inflammatory agent", refers to any one of numerous compounds containing a 17-carbon 4-ring system and includes the sterols, various hormones (as anabolic steroids), and glycosides. Representative examples of steroidal anti-inflammatory drugs include, without limitation, corticosteroids such as alpha-methyl dexamethasone, ameinafel, ameinafide, beclomethasone dipropionates, beclomethasone dipropionate, betamethasone and the balance of its esters, chloroprednisone, chlorprednisone acetate, clescinolone, clobetasol valerate, clocortelone, cortisone, cortodoxone, desonide, desoxycorticosterone acetate, desoxymethasone, dexamethasone, dexamethasone-phosphate, dichlorisone, dichlorisone, diflorasone diacetate, diflucortolone valerate, difluorosone diacetate, diflurosone diacetate, diflurprednate, fluadrenolone, flucetonide, fluclorolone acetonide, flucloronide, flucortine butylesters, fludrocortisone, fludrocortisone, fludrocortisone, flumethasone pivalate, flunisolide, fluocinonide, fluocortolone, fluoromethalone, fluosinolone acetonide, fluperolone, fluprednidene (fluprednylidene) acetate, fluprednisolone, fluradrenolone acetonide, fluradrenolone, flurandrenolone, halcinonide, hydrocortamate, hydrocortisone acetate, hydrocortisone butyrate, hydrocortisone valerate, hydrocortisone cyclopentylpropionate, hydrocortisone, hydroxyltriamcinolone, medrysone, meprednisone, methylprednisolone, paramethasone, prednisolone, prednisone, triamcinolone acetonide, triamcinolone, and combinations thereof.

"Substituted": It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of inflammatory diseases and/or disorders, e.g., in the modulation of a G-protein signaling cascade.

Some examples of substituents of aliphatic and other moieties of compounds provided by the present invention include, but are not limited to aliphatic; heteroaliphatic; aryl (e.g., phenyl); heteroaryl; arylalkyl; heteroarylalkyl; alkoxy; aryloxy; arylthio, heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

"Stable": As used herein, the term "stable" preferably refers to the state of maintaining integrity of a compound over a period of time (e.g., during manufacture and/or storage).

"Substantially free of": As used herein, the term "substantially free of", when used to describe a material or compound, means that the material or compound lacks a significant or detectable amount of a designated substance. In some embodiments, the designated substance is present at a level not more than about 1%, 2%, 3%, 4% or 5% (w/w or v/v) of the material or compound.

"Surfactants": As used herein, the term "surfactant" is a surface-active substance, such as a detergent. Suitable surfactants for use with the inventive compositions include, but are not limited to, sarcosinates, glutamates, sodium alkyl sulfates, ammonium alkyl sulfates, sodium alkyleth sulfates, ammonium alkyleth sulfates, ammonium laureth-n-sulfates, sodium laureth-n-sulfates, isothionates, glycerylether sulfonates, sulfosuccinates and combinations thereof. More particularly, an anionic surfactant is selected from the group consisting of sodium lauroyl sarcosinate, monosodium lauroyl glutamate, sodium alkyl sulfates, ammonium alkyl sulfates, sodium alkyleth sulfates, ammonium alkyleth sulfates, and combinations thereof.

"Sun screening agent": As used herein, a "sun screening agent" refers to an agent, when topically applied, absorbs or reflects some of the sun's ultraviolet radiation on skin exposed to sunlight, and therefore helps protect against sunburn. In some embodiments, a sun screening agent absorbed in the skin may lead to an increase in reactive oxygen species. Representative examples of sun screening agents usable in the present invention include, without limitation, p-aminobenzoic acid and its salts and derivatives thereof (p-dimethylaminobenzoic acid; ethyl, glyceryl, and isobutyl esters); anthranilates (i.e., o-amino-benzoates; benzyl, cyclohexenyl, linalyl, menthyl, methyl, phenyl, phenylethyl, and terpinyl esters); benzophenones (i.e., hydroxy- or methoxy-substituted benzophenones such as benzoresorcinol, butylmethoxydibenzoylmethane, 2,2'-dihydroxy-4,4'-dimethoxybenzophenone, etocrylene, 4-isopropyldibenzoylmethane, dioxybenzone, 3-4'-methylbenzylidene-boman-2-one, octabenzone, octocrylene, oxybenzene, sulisobenzone, and 2,2',4,4'-tetrahydroxybenzophenone); (butyl carbotol) (6-propyl piperonyl) ether; cinnamic acid derivatives (alpha.-phenyl cinnamonitrile; butyl cinnamoyl pyruvate; benzyl and methyl esters); diazoles (2-acetyl-3-bromoindazole, aryl benzothiazoles, methyl naphthoxazole, and phenyl benzoxazole); dibenzylacetone; dihydroxycinnamic acid derivatives (methylaceto-umbelliferone, methylumbelliferone, umbelliferone); di-hydroxynaphthoic acid and its salts; hydrocarbons (diphenylbutadiene, and stilbene); hydroquinone; o- and p-hydroxybiphenyldisulfonates; coumarin derivatives (3-phenyl, 7-hydroxy, and 7-methyl); naphtholsulfonates (sodium salts of 2-naphthol-3,6-disulfonic and of 2-naphthol-6,8-disulfonic acids); quinine salts (bisulfate, chloride, oleate, sulfate and tannate); quinoline derivatives (8-hydroxyquinoline salts, and 2-phenylquinoline); salicylates (amyl, benzyl, di-propylene glycol, glyceryl, menthyl, octyl, and phenyl esters); tannic acid and its derivatives (e.g., hexaethylether); trihydroxy-cinnamic acid derivatives (daphnetin, daphnin, esculetin, esculin, methylesculetin; and the glucosides); and uric and violuric acids; and combinations thereof.

"Thickeners": As used herein, the term "thickener" refers to agents that make a composition more dense or viscous in consistency. Suitable thickeners that can be used in the context of the present invention include, for example, nonionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids, anionic polymers, and their alkali salts and mixtures thereof.

"Thio": As used herein, the term "thio" used alone or as part of a larger moiety as in "alkylthio", "arylthio", "heteroalkylthio", or "heteroarylthio" refers to replacement of an oxygen. For example, "alkylthio" refers to an alkyl group, as previously defined, attached to the parent molecule through a sulfur atom. Similarly, "arylthio" refers to an aryl group, as previously defined, attached to the parent molecule through a sulfur molecule. Similarly, "heteroalkylthio" refers to a heteroalkyl group, as previously defined, attached to the parent molecule through a sulfur molecule, etc.

"Treat," "treating" and "treatment": As used herein, the terms "treat," "treating" and "treatment," contemplate an action that occurs while a patient is suffering from or susceptible to a specified disease, disorder or condition, which delays onset of and/or reduces the frequency or severity of one or more symptoms or features of the disease disorder or condition. Thus, "treat", "treating", and "treatment" refer to any type of treatment that imparts a benefit to a subject afflicted with a disease, disorder or condition, including improvement in the condition of the subject (e.g., in one or more symptoms), delay in the progression of the disease, disorder or condition, prevention or delay of the onset of the disease, disorder or condition, etc.

Unit dosage form: The expression "unit dosage form" as used herein refers to a physically discrete unit of a provided formulation appropriate for the subject to be treated. It will be understood, however, that the total daily usage of provided formulation will be decided by the attending physician within the scope of sound medical judgment. The specific effective dose level for any particular subject or organism may depend upon a variety of factors including the disorder being treated and the severity of the disorder; activity of specific active agent employed; specific formulation employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts. In some embodiments, a unit dosage form contains an amount of a therapeutically active agent appropriate for use in a therapeutic regimen (i.e., in a regimen that delivers a therapeutically effective amount of an agent). In some embodiments, such a unit dosage form may be considered to contain a "therapeutically effective amount" of an agent even if a single dose would not be expected to be effective.

"Unsaturated": As used herein, the term "unsaturated" means that a moiety has one or more units of unsaturation.

"Vitamin": As used herein, the term "vitamin" refers to any of various organic substances essential in minute quantities to the nutrition of most animals act especially as coenzymes and precursors of coenzymes in the regulation of metabolic processes. Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Z is a substituted or unsubstituted, branched or unbranched, saturated or unsaturated, $C_{10}$-$C_{25}$ aliphatic;

provided that when A and B are both —$CH_2$—, D is hydroxyl, X is —C(O)— and E is hydrogen, Y cannot be hydroxyl, —$OCH_3$ or —$CH_3$.

In one embodiment, presently disclosed compounds include those compounds encompassed by the formula:

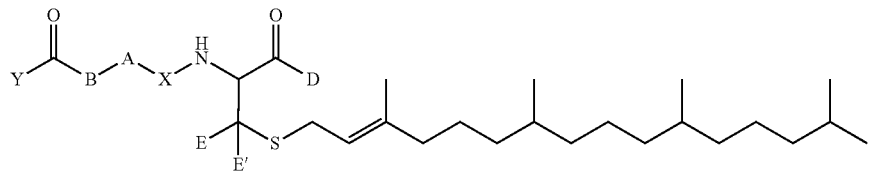

1. Description of Certain Exemplary Compounds

Presently disclosed compounds provided by the present invention include those described generally above, and are further illustrated by all classes, subclasses and species of each of these compounds disclosed herein.

In one embodiment, presently disclosed compounds include those compounds encompassed by the formula:

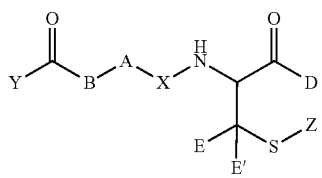

or a pharmaceutically acceptable salt, solvate, prodrug or ester thereof;
wherein:
X is —C(O)— or a covalent bond;
Y is hydroxyl, —$NH_2$, —O—$C_1$-$C_5$ alkyl or $C_1$-$C_5$ alkyl;
A and B are independently selected from NR, N($C_1$-$C_5$ alkyl), N($C_1$-$C_5$ alkylene)-R, N($C_1$-$C_5$ alkylene)-CN, N($C_1$-$C_5$ alkylene carboxyl), each of said alkyl or alkylene group optionally substituted with one or more R groups, —O—, a R-substituted or unsubstituted $C_1$-$C_5$ alkylene, a R-substituted or unsubstituted O—$C_1$-$C_5$ alkylene, a R-substituted or unsubstituted arylene or a R-substituted or unsubstituted heteroarylene having 1-4 heteroatoms independently selected from nitrogen, oxygen, or sulfur, or a R-substituted or unsubstituted $C_3$-$C_6$ cycloalkylene or R-substituted or unsubstituted $C_3$-$C_6$ heterocycloalkylene having 1-4 heteroatoms independently selected from nitrogen, oxygen or sulfur;
or A and B together form a R-substituted or unsubstituted arylene or a R-substituted or unsubstituted heteroarylene having 1-4 heteroatoms independently selected from nitrogen, oxygen, or sulfur, or a R-substituted or unsubstituted $C_3$-$C_6$ cycloalkylene or R-substituted or unsubstituted $C_3$-$C_6$ heterocycloalkylene having 1-4 heteroatoms independently selected from nitrogen, oxygen or sulfur;
D is —OH or —O($C_1$-$C_5$ alkyl); and
E and E' are independently selected from H and $C_1$-$C_5$ alkyl;
R is, independently, H, $C_1$-$C_5$ alkyl, OH, S($C_1$-$C_5$ alkyl), NH($C_1$-$C_5$ alkyl), NH($C_1$-$C_5$ alkylene carboxyl), NH($C_1$-$C_5$ alkylene guanidine), N($C_1$-$C_5$ alkylene amidine), N($C_1$-$C_5$ alkylene amide), $CF_3$, —CN, —COOH or O($C_1$-$C_5$ alkyl); and or a pharmaceutically acceptable salt, solvate, prodrug or ester thereof;
wherein:
X is —C(O)— or a covalent bond;
Y is hydroxyl, —$NH_2$, —O—$C_1$-$C_5$ alkyl or $C_1$-$C_5$ alkyl;
A and B are independently selected from NR, N($C_1$-$C_5$ alkyl), N($C_1$-$C_5$ alkylene)-R, N($C_1$-$C_5$ alkylene)-CN, N($C_1$-$C_5$ alkylene carboxyl), each of said alkyl or alkylene group optionally substituted with one or more R groups, —O—, a R-substituted or unsubstituted $C_1$-$C_5$ alkylene, a R-substituted or unsubstituted O—$C_1$-$C_5$ alkylene, a R-substituted or unsubstituted arylene or a R-substituted or unsubstituted heteroarylene having 1-4 heteroatoms independently selected from nitrogen, oxygen or sulfur, or a R-substituted or unsubstituted $C_3$-$C_6$ cycloalkylene or R-substituted or unsubstituted $C_3$-$C_6$ heterocycloalkylene having 1-4 heteroatoms independently selected from nitrogen, oxygen or sulfur;
or A and B together form a R-substituted or unsubstituted arylene or a R-substituted or unsubstituted heteroarylene having 1-4 heteroatoms independently selected from nitrogen, oxygen, or sulfur, or a R-substituted or unsubstituted $C_3$-$C_6$ cycloalkylene or R-substituted or unsubstituted $C_3$-$C_6$ heterocycloalkylene having 1-4 heteroatoms independently selected from nitrogen, oxygen or sulfur;
D is —OH or —O($C_1$-$C_5$ alkyl);
E and E' are independently selected from H and $C_1$-$C_5$ alkyl;
R is, independently, H, $C_1$-$C_5$ alkyl, OH, S($C_1$-$C_5$ alkyl), NH($C_1$-$C_5$ alkyl), NH($C_1$-$C_5$ alkylene carboxyl), NH($C_1$-$C_5$ alkylene guanidine), N($C_1$-$C_5$ alkylene amidine), N($C_1$-$C_5$ alkylene amide), $CF_3$, —CN, —COOH or O($C_1$-$C_5$ alkyl);
provided that when A and B are both —$CH_2$—, D is hydroxyl, X is —C(O)— and E is hydrogen, Y cannot be hydroxyl, —$OCH_3$ or —$CH_3$.

In one embodiment, presently disclosed compounds include those compounds encompassed by the formula:

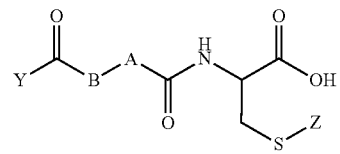

or a pharmaceutically acceptable salt, solvate, prodrug or ester thereof;

wherein:

Y is hydroxyl, —NH$_2$, —O—C$_1$-C$_5$ alkyl or C$_1$-C$_5$ alkyl;

A and B are independently selected from NR, N(C$_1$-C$_5$ alkyl), N(C$_1$-C$_5$ alkylene)-R, N(C$_1$-C$_5$ alkylene)-CN, N(C$_1$-C$_5$ alkylene carboxyl), each of said alkyl or alkylene group optionally substituted with one or more R groups, —O—, a R-substituted or unsubstituted C$_1$-C$_5$ alkylene, a R-substituted or unsubstituted O—C$_1$-C$_5$ alkylene, a R-substituted or unsubstituted arylene or a R-substituted or unsubstituted heteroarylene having 1-4 heteroatoms independently selected from nitrogen, oxygen or sulfur, or a R-substituted or unsubstituted C$_3$-C$_6$ cycloalkylene or R-substituted or unsubstituted C$_3$-C$_6$ heterocycloalkylene having 1-4 heteroatoms independently selected from nitrogen, oxygen or sulfur;

or A and B together form a R-substituted or unsubstituted arylene or a R-substituted or unsubstituted heteroarylene having 1-4 heteroatoms independently selected from nitrogen, oxygen or sulfur, or a R-substituted or unsubstituted C$_3$-C$_6$ cycloalkylene or R-substituted or unsubstituted C$_3$-C$_6$ heterocycloalkylene having 1-4 heteroatoms independently selected from nitrogen, oxygen or sulfur;

unsubstituted arylene or a R-substituted or unsubstituted heteroarylene having 1-4 heteroatoms independently selected from nitrogen, oxygen or sulfur, or a R-substituted or unsubstituted C$_3$-C$_6$ cycloalkylene or R-substituted or unsubstituted C$_3$-C$_6$ heterocycloalkylene having 1-4 heteroatoms independently selected from nitrogen, oxygen or sulfur;

or A and B together form a R-substituted or unsubstituted arylene or a R-substituted or unsubstituted heteroarylene having 1-4 heteroatoms independently selected from nitrogen, oxygen or sulfur, or a R-substituted or unsubstituted C$_3$-C$_6$ cycloalkylene or R-substituted or unsubstituted C$_3$-C$_6$ heterocycloalkylene having 1-4 heteroatoms independently selected from nitrogen, oxygen or sulfur;

R is, independently, H, C$_1$-C$_5$ alkyl, OH, S(C$_1$-C$_5$ alkyl), NH(C$_1$-C$_5$ alkyl), NH(C$_1$-C$_5$ alkylene carboxyl), NH(C$_1$-C$_5$ alkylene guanidine), N(C$_1$-C$_5$ alkylene amidine), N(C$_1$-C$_5$ alkylene amide) or O(C$_1$-C$_5$ alkyl);

provided that when A and B are both —CH$_2$—, Y cannot be hydroxyl, —OCH$_3$ or —CH$_3$.

In one embodiment, the presently disclosed compounds include those compounds encompassed by the formula:

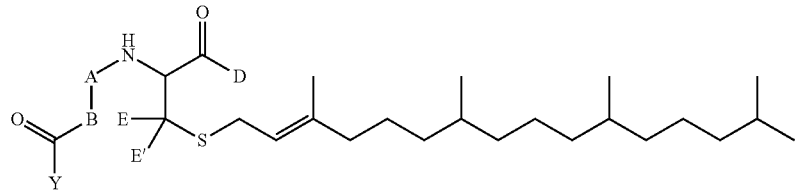

R is, independently, H, C$_1$-C$_5$ alkyl, OH, S(C$_1$-C$_5$ alkyl), NH(C$_1$-C$_5$ alkyl), NH(C$_1$-C$_5$ alkylene carboxyl), NH(C$_1$-C$_5$ alkylene guanidine), N(C$_1$-C$_5$ alkylene amidine), N(C$_1$-C$_5$ alkylene amide), CF$_3$, —CN, —COOH or O(C$_1$-C$_5$ alkyl); and Z is a substituted or unsubstituted, branched or unbranched, saturated or unsaturated, C$_{10}$-C$_{25}$ aliphatic;

provided that when A and B are both —CH$_2$—, Y cannot be hydroxyl, —OCH$_3$ or —CH$_3$.

In one embodiment, Z is selected from a farnesyl or phytyl group. In one embodiment, Z is a farnesyl group. In one embodiment, Z is a phytyl group.

In one embodiment, presently disclosed compounds include those compounds encompassed by the formula:

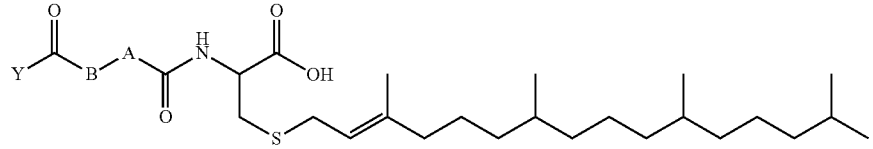

or a pharmaceutically acceptable salt, solvate, prodrug or ester thereof;

wherein:

Y is hydroxyl, —NH$_2$, —O—C$_1$-C$_5$ alkyl or C$_1$-C$_5$ alkyl;

A and B are independently selected from NR, N(C$_1$-C$_5$ alkyl), N(C$_1$-C$_5$ alkylene)-R, N(C$_1$-C$_5$ alkylene)-CN, N(C$_1$-C$_5$ alkylene carboxyl), each of said alkyl or alkylene group optionally substituted with one or more R groups, —O—, a R-substituted or unsubstituted C$_1$-C$_5$ alkylene, a R-substituted or unsubstituted O—C$_1$-C$_5$ alkylene, a R-substituted or or a pharmaceutically acceptable salt, solvate, prodrug or ester thereof;

wherein:

Y is hydroxyl, —NH$_2$, —O—C$_1$-C$_5$ alkyl or C$_1$-C$_5$ alkyl;

A and B together form a R-substituted or unsubstituted arylene or a R-substituted or unsubstituted heteroarylene having 1-4 heteroatoms independently selected from nitrogen, oxygen, or sulfur, or a R-substituted or unsubstituted C$_3$-C$_6$ cycloalkylene or R-substituted or unsubstituted C$_3$-C$_6$ heterocycloalkylene having 1-4 heteroatoms independently selected from nitrogen, oxygen, or sulfur;

D is —OH or —O(C$_1$-C$_5$ alkyl);

E and E' are independently selected from H and C$_1$-C$_5$ alkyl; and

R is, independently, H, C$_1$-C$_5$ alkyl, OH, S(C$_1$-C$_5$ alkyl), NH(C$_1$-C$_5$ alkyl), NH(C$_1$-C$_5$ alkylene carboxyl), NH(C$_1$-C$_5$ alkylene guanidine), N(C$_1$-C$_5$ alkylene amidine), N(C$_1$-C$_5$ alkylene amide), CF$_3$, —CN, —COOH, or O(C$_1$-C$_5$ alkyl).

In one embodiment, presently disclosed compounds include those compounds encompassed by the formula:

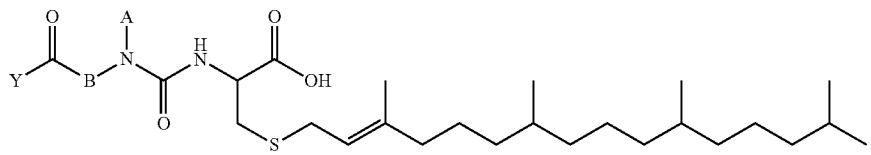

or a pharmaceutically acceptable salt, solvate, prodrug or ester thereof;
wherein:
Y is hydroxyl, —$NH_2$, —O—$C_1$-$C_5$ alkyl or $C_1$-$C_5$ alkyl;
A is selected from R, $C_1$-$C_5$ alkyl, ($C_1$-$C_5$ alkylene)-R, ($C_1$-$C_5$ alkylene)-CN, ($C_1$-$C_5$ alkylene)-carboxyl, each of said alkyl or alkylene group optionally substituted with one or more R groups;
B is an unsubstituted $C_1$-$C_2$ alkylene;
or A, B and the nitrogen atom bound to A and B form a R-substituted or unsubstituted $C_3$-$C_6$ heterocycloalkylene having 1-4 heteroatoms independently selected from nitrogen, oxygen or sulfur; and
R is, independently, H, $C_1$-$C_5$ alkyl, OH, S($C_1$-$C_5$ alkyl), NH($C_1$-$C_5$ alkyl), NH($C_1$-$C_5$ alkylene carboxyl), NH($C_1$-$C_5$ alkylene guanidine), N($C_1$-$C_5$ alkylene amidine), N($C_1$-$C_5$ alkylene amide), $CF_3$, —CN, —COOH or O($C_1$-$C_5$ alkyl).

In one embodiment, presently disclosed compounds include those compounds encompassed by the formula:

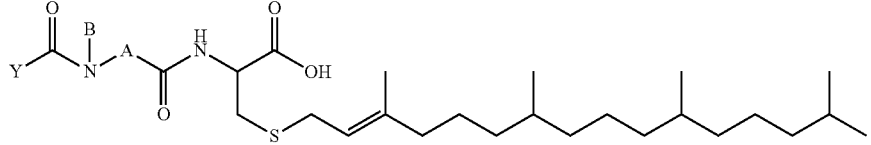

or a pharmaceutically acceptable salt, solvate, prodrug or ester thereof;
wherein:
Y is hydroxyl, —$NH_2$, —O—$C_1$-$C_5$ alkyl or $C_1$-$C_5$ alkyl;
A is an unsubstituted $C_1$-$C_2$ alkylene;
B is selected from R, $C_1$-$C_5$ alkyl, ($C_1$-$C_5$ alkylene)-R, ($C_1$-$C_5$ alkylene)-CN, ($C_1$-$C_5$ alkylene)-carboxyl, each of said alkyl or alkylene group optionally substituted with one or more R groups; or A, B and the nitrogen atom bound to A and B form a R-substituted or unsubstituted $C_3$-$C_6$ heterocycloalkylene having 1-4 heteroatoms independently selected from nitrogen, oxygen or sulfur; and R is, independently, H, $C_1$-$C_5$ alkyl, OH, S($C_1$-$C_5$ alkyl), NH($C_1$-$C_5$ alkyl), NH($C_1$-$C_5$ alkylene carboxyl), NH($C_1$-$C_5$ alkylene guanidine), N($C_1$-$C_5$ alkylene amidine), N($C_1$-$C_5$ alkylene amide), $CF_3$, —CN, —COOH or O($C_1$-$C_5$ alkyl).

In one embodiment, presently disclosed compounds include those compounds encompassed by the formula:

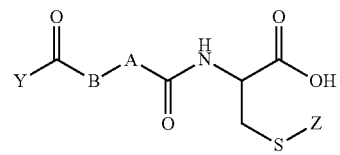

or a pharmaceutically acceptable salt, solvate, prodrug or ester thereof;
wherein:
Y is hydroxyl, —$NH_2$, —O—$C_1$-$C_5$ alkyl or $C_1$-$C_5$ alkyl;
A is NH, N($C_1$-$C_5$ alkyl), N($C_1$-$C_5$ alkylene carboxyl) or a R-substituted or unsubstituted $C_1$-$C_5$ alkylene;
B is NH, N($C_1$-$C_5$ alkyl), N($C_1$-$C_5$ alkylene carboxyl) or a R-substituted or unsubstituted $C_1$-$C_5$ alkylene;
or A and B together form a R-substituted or unsubstituted arylene or a R-substituted or unsubstituted heteroarylene having 1-4 heteroatoms independently selected from nitrogen, oxygen, or sulfur, or a R-substituted or unsubstituted $C_3$-$C_6$ cycloalkylene or R-substituted or unsubstituted $C_3$-$C_6$ heterocycloalkylene having 1-4 heteroatoms independently selected from nitrogen, oxygen or sulfur;
R is, independently, $C_1$-$C_5$ alkyl, OH, S($C_1$-$C_5$ alkyl), NH($C_1$-$C_5$ alkyl), NH($C_1$-$C_5$ alkylene carboxyl), NH($C_1$-$C_5$ alkylene guanidine), N($C_1$-$C_5$ alkylene amidine), N($C_1$-$C_5$ alkylene amide) or O($C_1$-$C_5$ alkyl); and
Z is is a substituted or unsubstituted, branched or unbranched, saturated or unsaturated, $C_{10}$-$C_{25}$ aliphatic;
provided that when A and B are both —$CH_2$—, Y cannot be hydroxyl, —$OCH_3$ or —$CH_3$.

In one embodiment, Z is selected from a farnesyl or phytyl group. In one embodiment, Z is a farnesyl group. In one embodiment, Z is a phytyl group.

In one embodiment, presently disclosed compounds include those compounds encompassed by the formula:

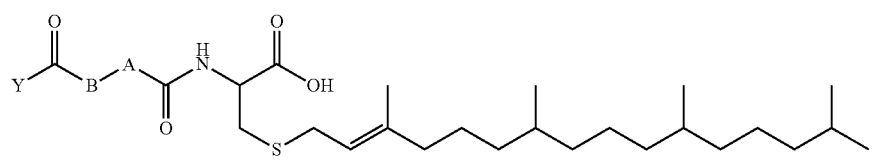

or a pharmaceutically acceptable salt, solvate, prodrug or ester thereof; wherein:
Y is hydroxyl, —$NH_2$, —O—$C_1$-$C_5$ alkyl or $C_1$-$C_5$ alkyl;
A is NH, N($C_1$-$C_5$ alkyl), N($C_1$-$C_5$ alkylene carboxyl) or a R-substituted or unsubstituted $C_1$-$C_5$ alkylene;
B is NH, N($C_1$-$C_5$ alkyl), N($C_1$-$C_5$ alkylene carboxyl) or a R-substituted or unsubstituted $C_1$-$C_5$ alkylene;
or A and B together form a R-substituted or unsubstituted arylene or a R-substituted or unsubstituted heteroarylene having 1-4 heteroatoms independently selected from nitrogen, oxygen or sulfur, or a R-substituted or unsubstituted $C_3$-$C_6$ cycloalkylene or R-substituted or unsubstituted $C_3$-$C_6$ heterocycloalkylene having 1-4 heteroatoms independently selected from nitrogen, oxygen or sulfur;
R is, independently, $C_1$-$C_5$ alkyl, OH, S($C_1$-$C_5$ alkyl), NH($C_1$-$C_5$ alkyl), NH($C_1$-$C_5$ alkylene carboxyl), NH($C_1$-$C_5$ alkylene guanidine), N($C_1$-$C_5$ alkylene amidine), N($C_1$-$C_5$ alkylene amide) or O($C_1$-$C_5$ alkyl);
provided that when A and B are both —$CH_2$—, Y cannot be hydroxyl, —$OCH_3$ or —$CH_3$.

In one embodiment, presently disclosed compounds include those compounds encompassed by the formula:

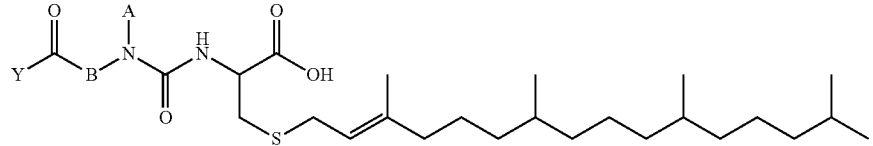

or a pharmaceutically acceptable salt, solvate, prodrug or ester thereof;
wherein:
Y is hydroxyl, —$NH_2$, —O—$C_1$-$C_5$ alkyl or $C_1$-$C_5$ alkyl;
A is hydrogen, an unsubstituted $C_1$-$C_2$ alkyl or $CH_2COOH$;
B is an unsubstituted $C_1$-$C_2$ alkylene;
or A, B and the nitrogen atom bound to A and B form a R-substituted or unsubstituted $C_3$-$C_6$ heterocycloalkylene having 1-4 heteroatoms independently selected from nitrogen, oxygen or sulfur; and R is $C_1$-$C_5$ alkyl, OH, S($C_1$-$C_5$ alkyl), NH($C_1$-$C_5$ alkyl), NH($C_1$-$C_5$ alkylene carboxyl), NH($C_1$-$C_5$ alkylene guanidine), N($C_1$-$C_5$ alkylene amidine), N($C_1$-$C_5$ alkylene amide) or O($C_1$-$C_5$ alkyl).

In one embodiment, presently disclosed compounds include those compounds encompassed by the formula:

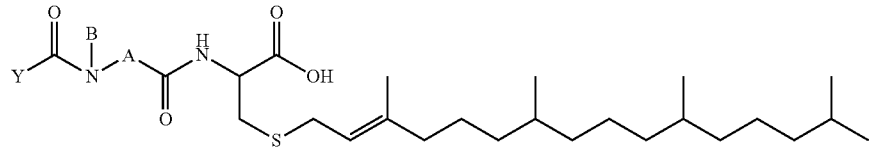

or a pharmaceutically acceptable salt, solvate, prodrug or ester thereof;
wherein:
Y is hydroxyl, —$NH_2$, —O—$C_1$-$C_5$ alkyl or $C_1$-$C_5$ alkyl;
A is an unsubstituted $C_1$-$C_2$ alkylene;
B is hydrogen, an unsubstituted $C_1$-$C_2$ alkyl or $CH_2COOH$;
or A, B and the nitrogen atom bound to A and B form a R-substituted or unsubstituted $C_3$-$C_6$ heterocycloalkylene having 1-4 heteroatoms independently selected from nitrogen, oxygen or sulfur; and R is $C_1$-$C_5$ alkyl, OH, S($C_1$-$C_5$ alkyl), NH($C_1$-$C_5$ alkyl), NH($C_1$-$C_5$ alkylene carboxyl), NH($C_1$-$C_5$ alkylene guanidine), N($C_1$-$C_5$ alkylene amidine), N($C_1$-$C_5$ alkylene amide) or O($C_1$-$C_5$ alkyl).

In one embodiment, presently disclosed compounds include those compounds set forth below in Table 1, or a pharmaceutically acceptable salt, solvate, prodrug or ester thereof.

TABLE 1
Exemplary Compounds
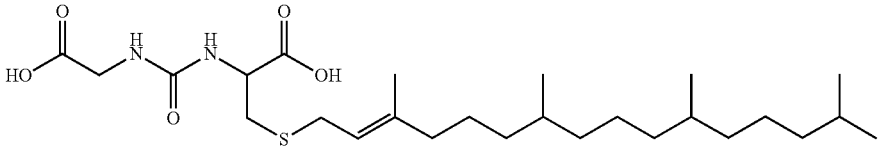 [SMILES: C/C(=C\CSCC(NC(=O)NCC(=O)O)C(=O)O)CCCC(C)CCCC(C)CCCC(C)C]
A
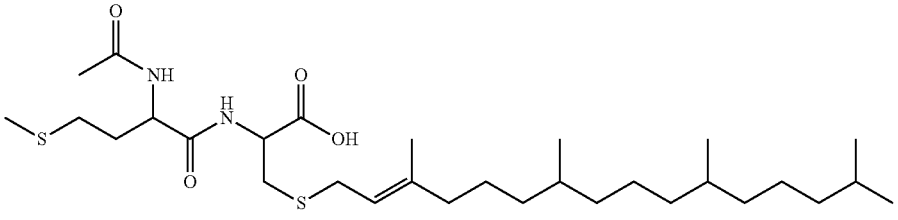
B
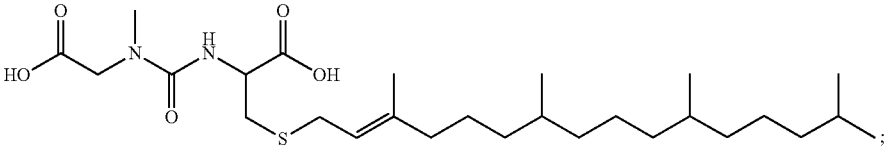 [SMILES: C/C(=C\CSCC(NC(=O)N(C)CC(=O)O)C(=O)O)CCCC(C)CCCC(C)CCCC(C)C]
C
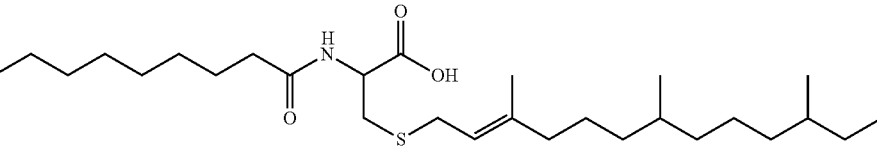
D
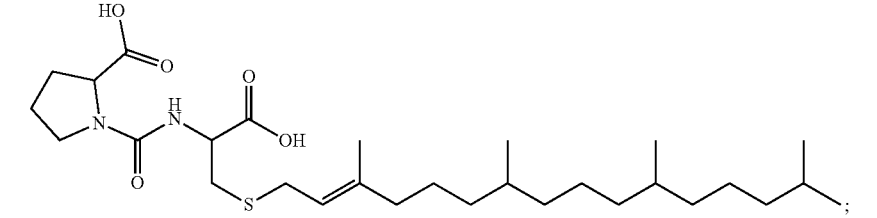 [SMILES: C/C(=C\CSCC(NC(=O)N1CCCC1C(=O)O)C(=O)O)CCCC(C)CCCC(C)CCCC(C)C]
E
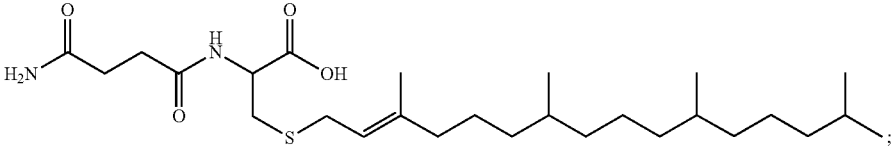 [SMILES: C/C(=C\CSCC(NC(=O)CCC(N)=O)C(=O)O)CCCC(C)CCCC(C)CCCC(C)C]
F
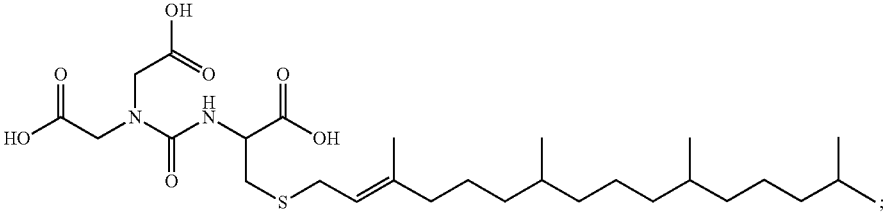 [SMILES: C/C(=C\CSCC(NC(=O)N(CC(=O)O)CC(=O)O)C(=O)O)CCCC(C)CCCC(C)CCCC(C)C]
G
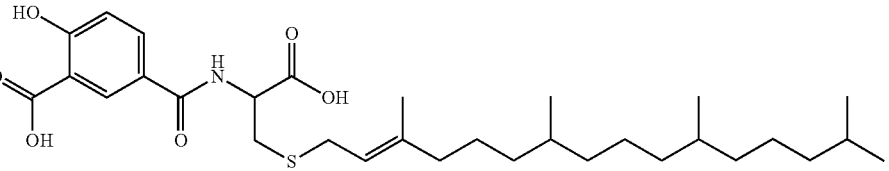
H TABLE 1-continued
Exemplary Compounds
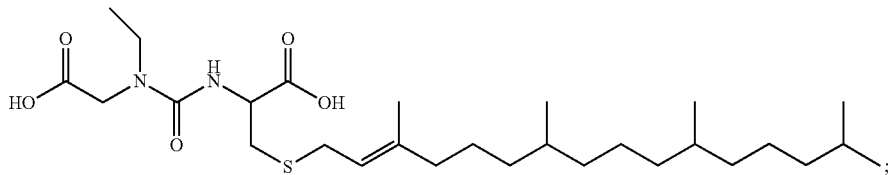 [SMILES: CCN(CC(=O)O)C(=O)NC(CSC/C=C(\C)CCCC(C)CCCC(C)CCCC(C)C)C(=O)O]
I
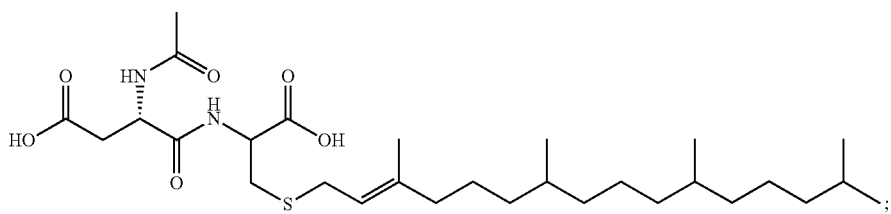 [SMILES: CC(=O)N[C@@H](CC(=O)O)C(=O)NC(CSC/C=C(\C)CCCC(C)CCCC(C)CCCC(C)C)C(=O)O]
J
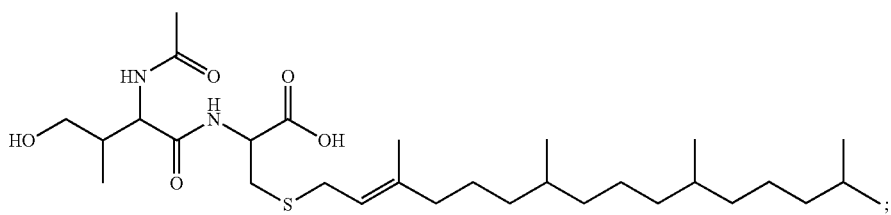 [SMILES: CC(=O)NC(C(=O)NC(CSC/C=C(\C)CCCC(C)CCCC(C)CCCC(C)C)C(=O)O)C(C)CO]
K
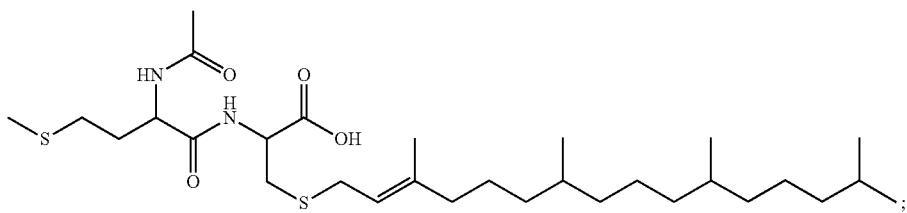 [SMILES: CSCCC(NC(C)=O)C(=O)NC(CSC/C=C(\C)CCCC(C)CCCC(C)CCCC(C)C)C(=O)O]
L
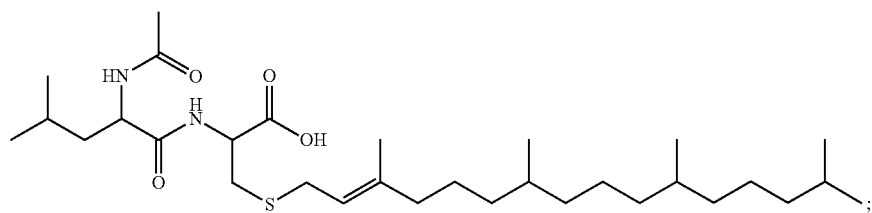 [SMILES: CC(=O)NC(CC(C)C)C(=O)NC(CSC/C=C(\C)CCCC(C)CCCC(C)CCCC(C)C)C(=O)O]
M
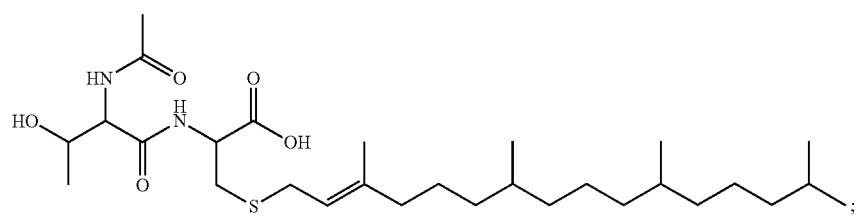 [SMILES: CC(=O)NC(C(=O)NC(CSC/C=C(\C)CCCC(C)CCCC(C)CCCC(C)C)C(=O)O)C(C)O]
N
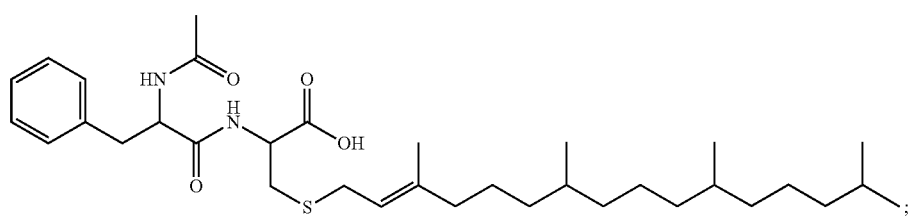 [SMILES: CC(=O)NC(Cc1ccccc1)C(=O)NC(CSC/C=C(\C)CCCC(C)CCCC(C)CCCC(C)C)C(=O)O]
O TABLE 1-continued
Exemplary Compounds
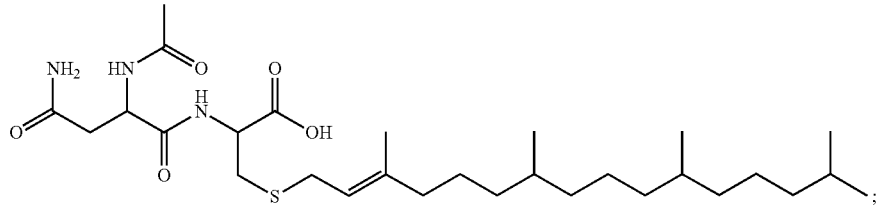 [SMILES: CC(=O)NC(CC(N)=O)C(=O)NC(CSC/C=C(\C)CCCC(C)CCCC(C)CCCC(C)C)C(=O)O]
P
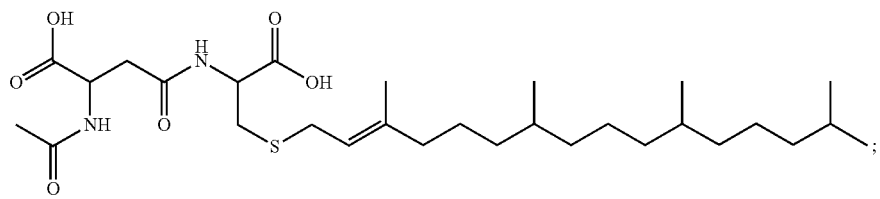 [SMILES: CC(=O)NC(CC(=O)NC(CSC/C=C(\C)CCCC(C)CCCC(C)CCCC(C)C)C(=O)O)C(=O)O]
Q
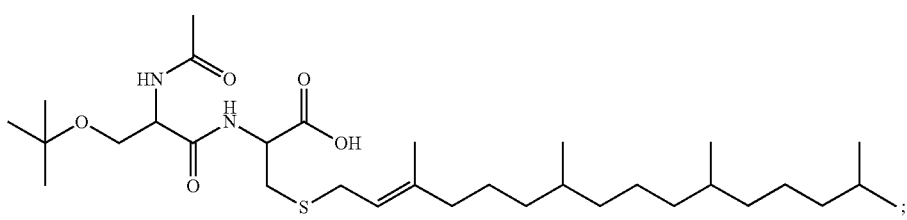 [SMILES: CC(=O)NC(COC(C)(C)C)C(=O)NC(CSC/C=C(\C)CCCC(C)CCCC(C)CCCC(C)C)C(=O)O]
R
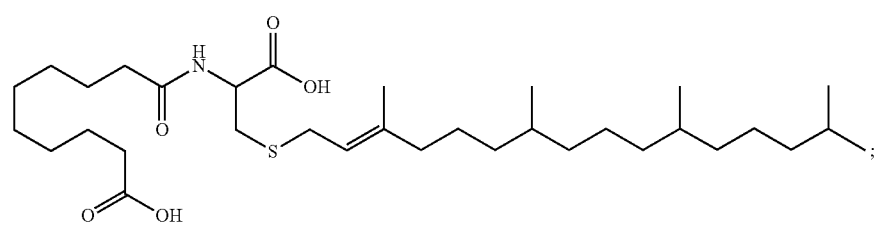 [SMILES: C/C(=C\CSCC(NC(=O)CCCCCCCCC(=O)O)C(=O)O)CCCC(C)CCCC(C)CCCC(C)C]
S
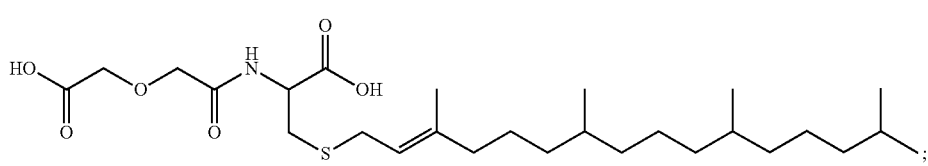 [SMILES: C/C(=C\CSCC(NC(=O)COCC(=O)O)C(=O)O)CCCC(C)CCCC(C)CCCC(C)C]
T
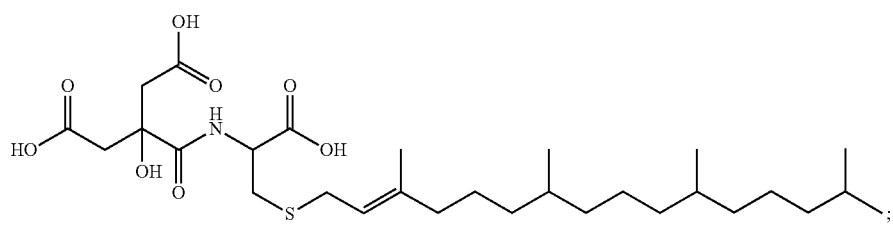 [SMILES: C/C(=C\CSCC(NC(=O)C(O)(CC(=O)O)CC(=O)O)C(=O)O)CCCC(C)CCCC(C)CCCC(C)C]
U
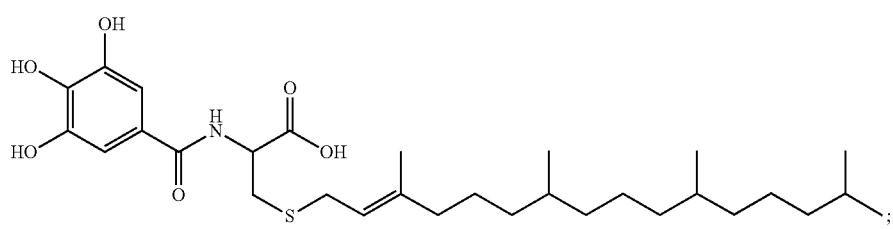 [SMILES: C/C(=C\CSCC(NC(=O)c1cc(O)c(O)c(O)c1)C(=O)O)CCCC(C)CCCC(C)CCCC(C)C]
V TABLE 1-continued Exemplary Compounds

| | |
|---|---|
| (structure) | W |
| (structure) | X |
| (structure) | Y |
| (structure) | Z |
| (structure) | AA |
| (structure) | AB |
| (structure) | AC |
| (structure) | AD |

TABLE 1-continued
Exemplary Compounds
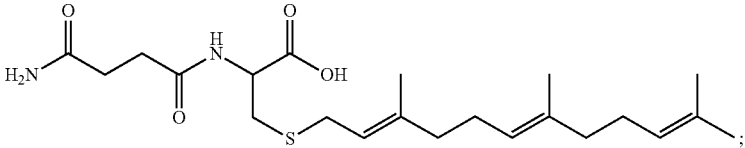 [SMILES: CC(C)=CCC/C(C)=C/CC/C(C)=C/CSCC(NC(=O)CCC(N)=O)C(=O)O]
AE
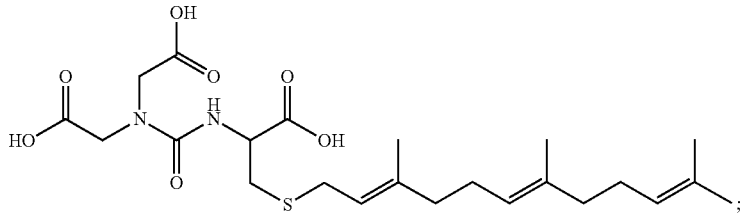 [SMILES: CC(C)=CCC/C(C)=C/CC/C(C)=C/CSCC(NC(=O)N(CC(=O)O)CC(=O)O)C(=O)O]
AF
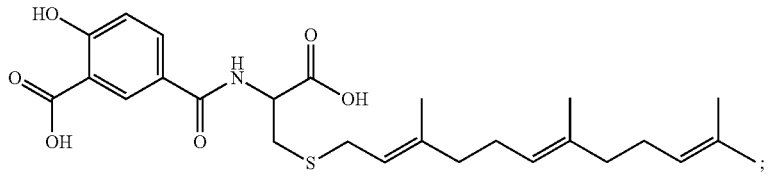 [SMILES: CC(C)=CCC/C(C)=C/CC/C(C)=C/CSCC(NC(=O)c1ccc(O)c(C(=O)O)c1)C(=O)O]
AG
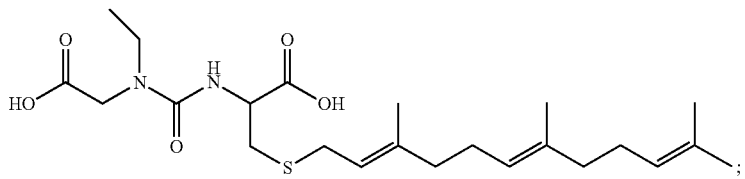 [SMILES: CCN(CC(=O)O)C(=O)NC(CSC/C=C(\C)CC/C=C(\C)CCC=C(C)C)C(=O)O]
AH
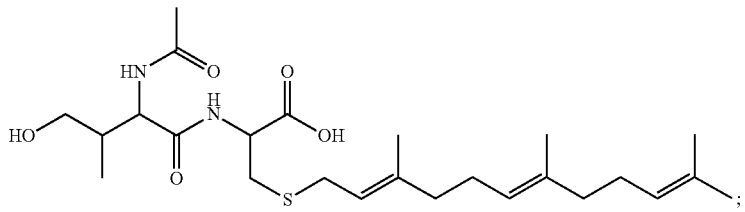 [SMILES: CC(=O)NC(C(=O)NC(CSC/C=C(\C)CC/C=C(\C)CCC=C(C)C)C(=O)O)C(C)CO]
AI
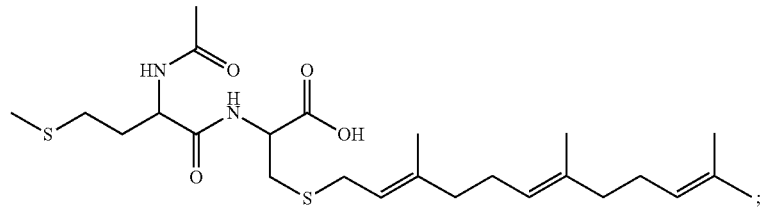 [SMILES: CSCCC(NC(C)=O)C(=O)NC(CSC/C=C(\C)CC/C=C(\C)CCC=C(C)C)C(=O)O]
AJ
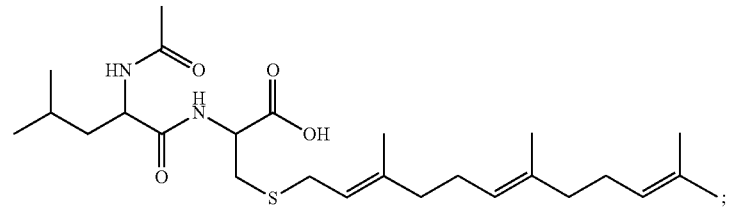 [SMILES: CC(=O)NC(CC(C)C)C(=O)NC(CSC/C=C(\C)CC/C=C(\C)CCC=C(C)C)C(=O)O]
AK TABLE 1-continued
Exemplary Compounds
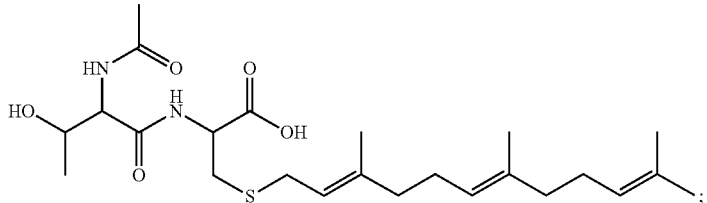 [SMILES: CC(=O)NC(C(=O)NC(CSC/C=C(\C)CC/C=C(\C)CCC=C(C)C)C(=O)O)C(C)O]
AL
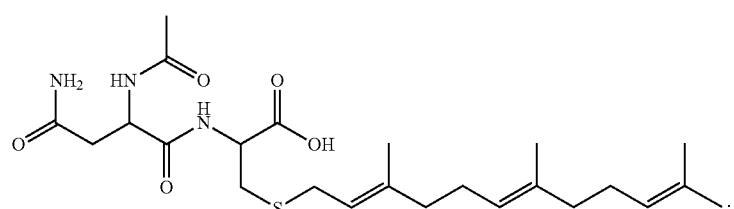
AM
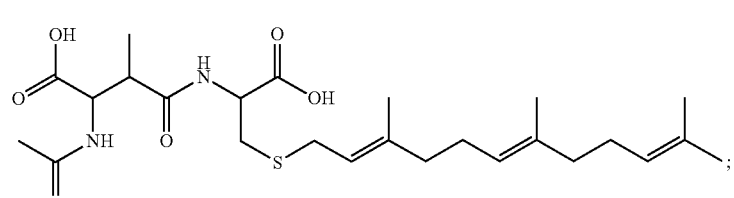
AN
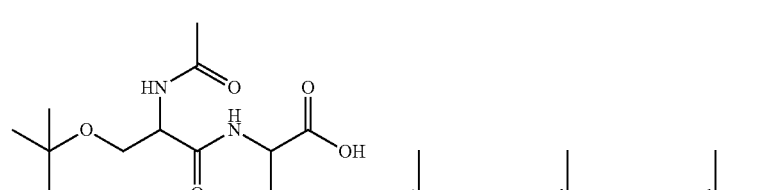
AO
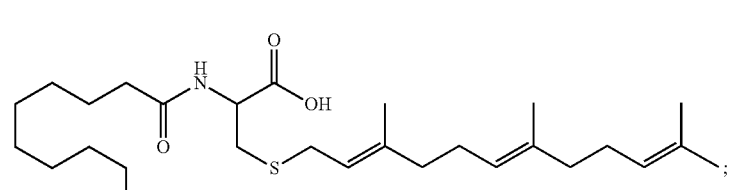
AP
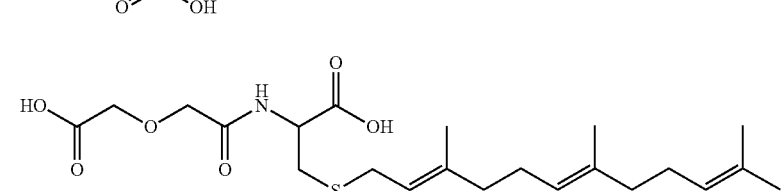
AQ
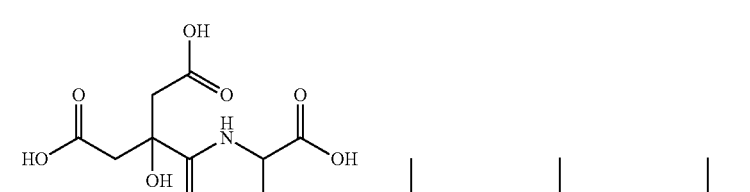
AR TABLE 1-continued Exemplary Compounds

| | |
|---|---|
| (structure) | AS |
| (structure) | AT |
| (structure) | AU |
| (structure) | AV |
| (structure) | AW |
| (structure) | AX |

TABLE 1-continued
Exemplary Compounds
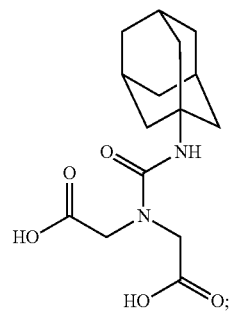 [SMILES: O=C(O)CN(CC(=O)O)C(=O)NC12CC3CC(CC(C3)C1)C2]
AY
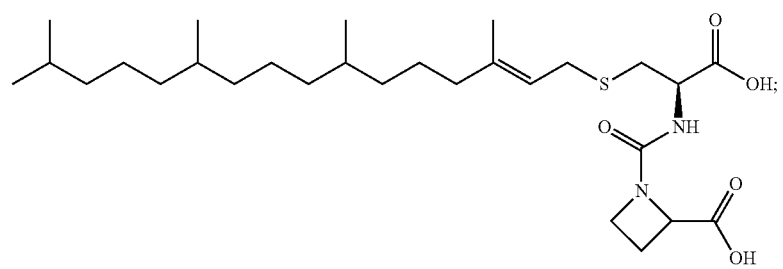 [SMILES: C/C(=C\CSC[C@H](NC(=O)N1CCC1C(=O)O)C(=O)O)CCCC(C)CCCC(C)CCCC(C)C]
AZ
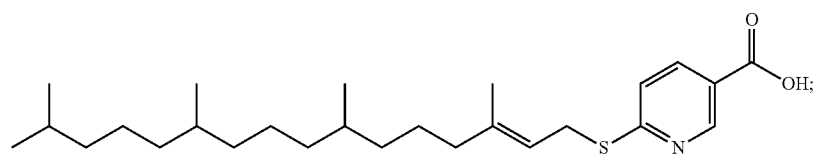 [SMILES: C/C(=C\CSc1ccc(C(=O)O)cn1)CCCC(C)CCCC(C)CCCC(C)C]
BA
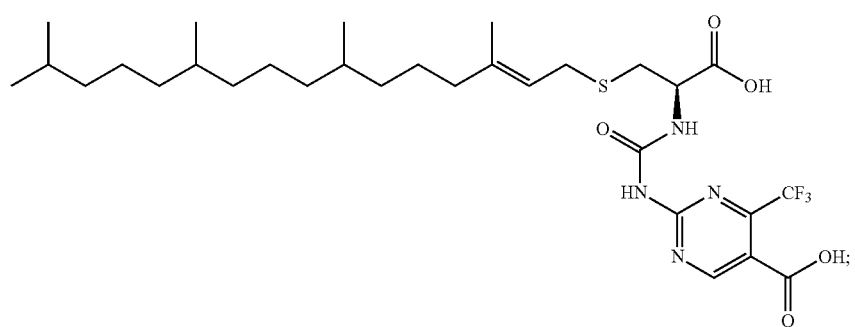 [SMILES: C/C(=C\CSC[C@H](NC(=O)Nc1ncc(C(=O)O)c(C(F)(F)F)n1)C(=O)O)CCCC(C)CCCC(C)CCCC(C)C]
BB
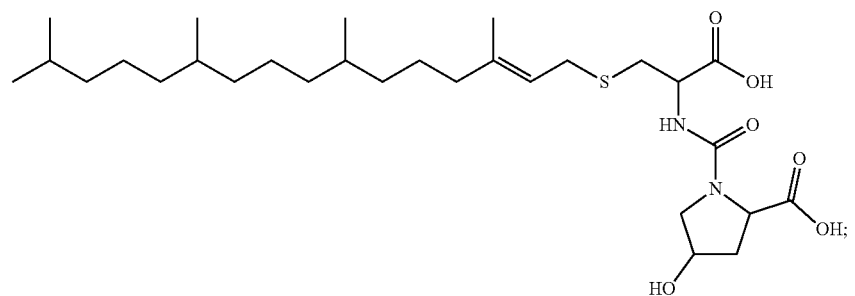 [SMILES: C/C(=C\CSCC(NC(=O)N1CC(O)CC1C(=O)O)C(=O)O)CCCC(C)CCCC(C)CCCC(C)C]
BC TABLE 1-continued
Exemplary Compounds
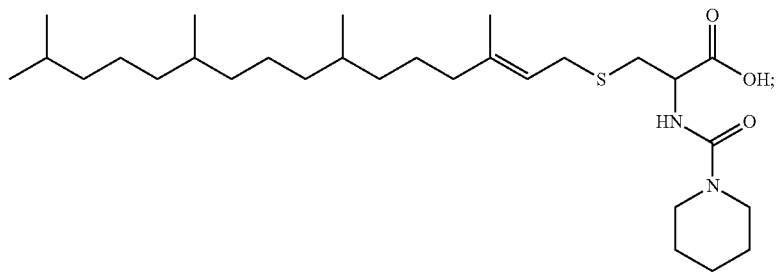 [SMILES: C/C(=C\CSCC(NC(=O)N1CCCCC1)C(=O)O)CCCC(C)CCCC(C)CCCC(C)C]
BD
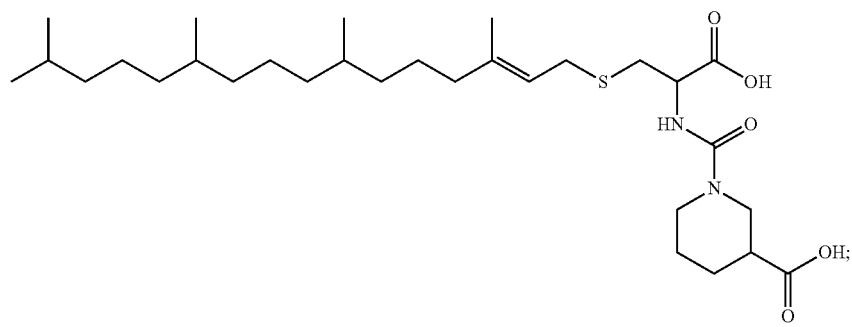 [SMILES: C/C(=C\CSCC(NC(=O)N1CCCC(C(=O)O)C1)C(=O)O)CCCC(C)CCCC(C)CCCC(C)C]
BE
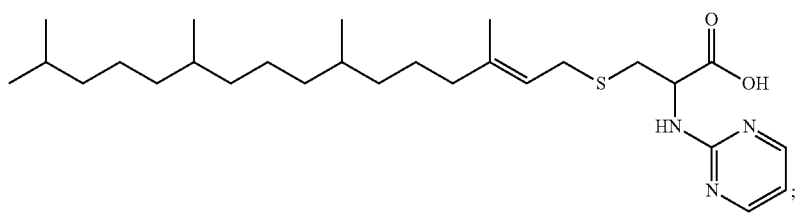 [SMILES: C/C(=C\CSCC(Nc1ncccn1)C(=O)O)CCCC(C)CCCC(C)CCCC(C)C]
BF
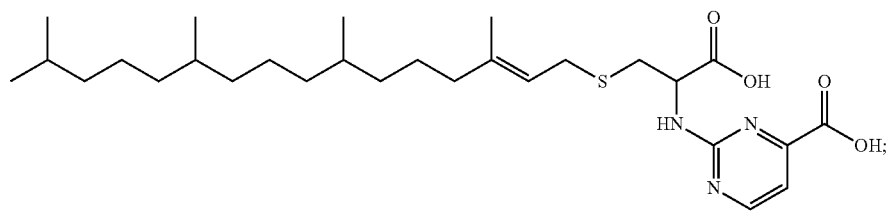 [SMILES: C/C(=C\CSCC(Nc1nccc(C(=O)O)n1)C(=O)O)CCCC(C)CCCC(C)CCCC(C)C]
BG
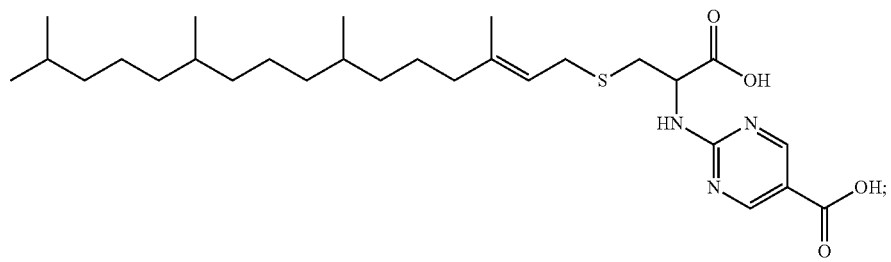 [SMILES: C/C(=C\CSCC(Nc1ncc(C(=O)O)cn1)C(=O)O)CCCC(C)CCCC(C)CCCC(C)C]
BH TABLE 1-continued Exemplary Compounds BI, BJ, BK, BL, BM (chemical structures)

TABLE 1-continued
Exemplary Compounds
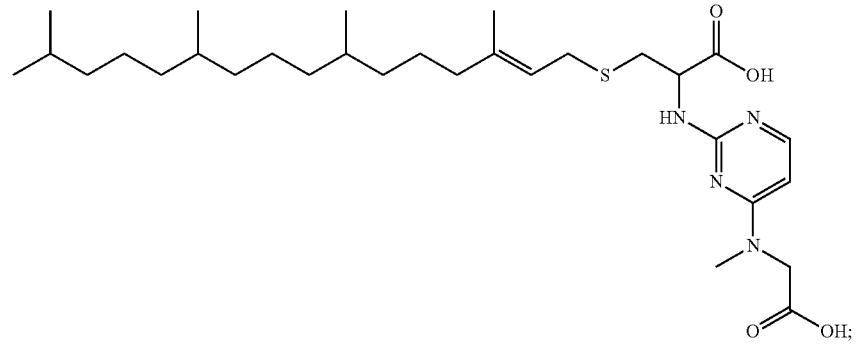 [SMILES: C/C(=C\CSCC(Nc1nccc(N(C)CC(=O)O)n1)C(=O)O)CCCC(C)CCCC(C)CCCC(C)C]
BN
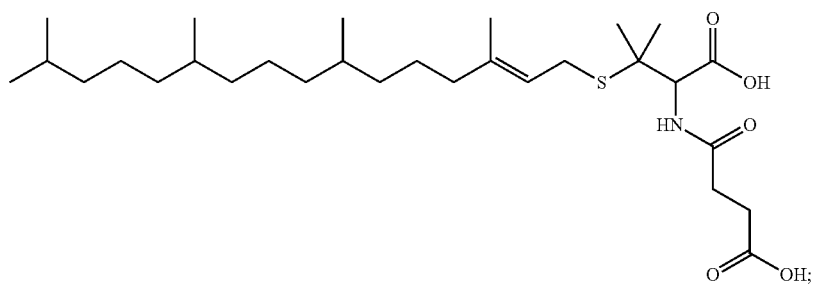 [SMILES: C/C(=C\CSC(C)(C)C(NC(=O)CCC(=O)O)C(=O)O)CCCC(C)CCCC(C)CCCC(C)C]
BO
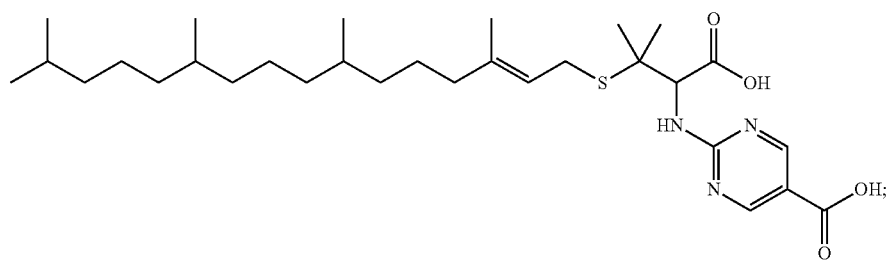 [SMILES: C/C(=C\CSC(C)(C)C(Nc1ncc(C(=O)O)cn1)C(=O)O)CCCC(C)CCCC(C)CCCC(C)C]
BP
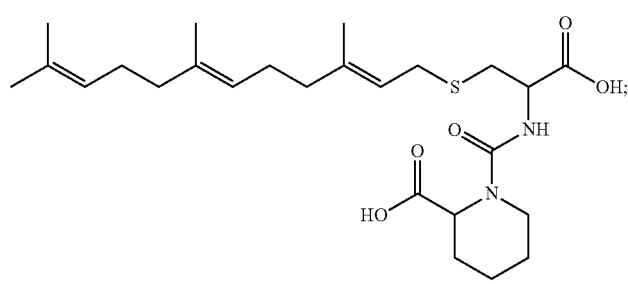 [SMILES: CC(C)=CCC/C(C)=C/CC/C(C)=C/CSCC(NC(=O)N1CCCCC1C(=O)O)C(=O)O]
BQ
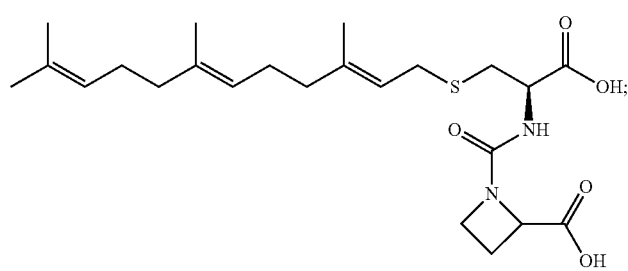 [SMILES: CC(C)=CCC/C(C)=C/CC/C(C)=C/CSC[C@H](NC(=O)N1CCC1C(=O)O)C(=O)O]
BR TABLE 1-continued
Exemplary Compounds
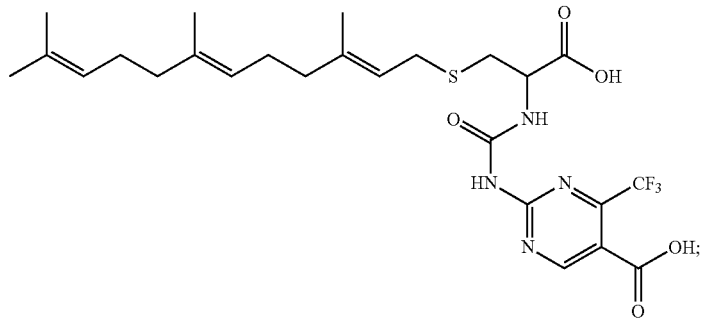 [SMILES: CC(C)=CCC/C(C)=C/CC/C(C)=C/CSCC(NC(=O)Nc1ncc(C(=O)O)c(C(F)(F)F)n1)C(=O)O]
BS
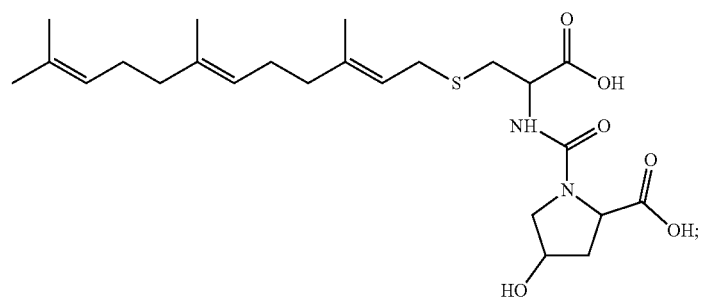 [SMILES: CC(C)=CCC/C(C)=C/CC/C(C)=C/CSCC(NC(=O)N1CC(O)CC1C(=O)O)C(=O)O]
BT
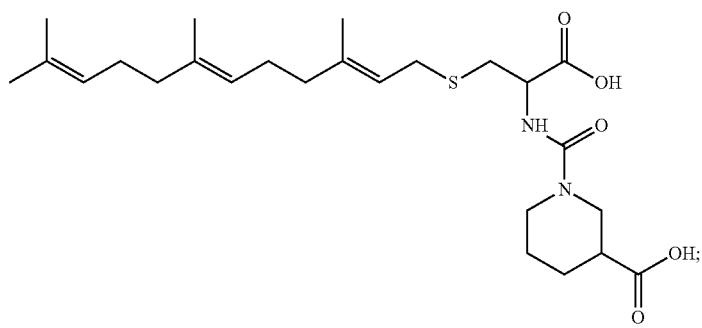 [SMILES: CC(C)=CCC/C(C)=C/CC/C(C)=C/CSCC(NC(=O)N1CCCC(C(=O)O)C1)C(=O)O]
BU
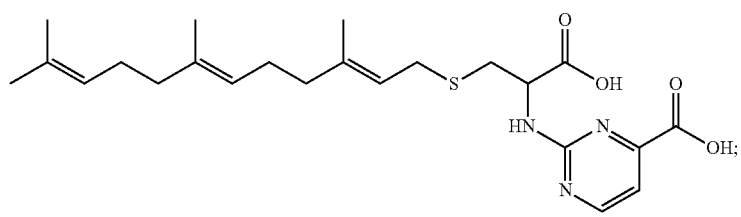 [SMILES: CC(C)=CCC/C(C)=C/CC/C(C)=C/CSCC(Nc1nccc(C(=O)O)n1)C(=O)O]
BV
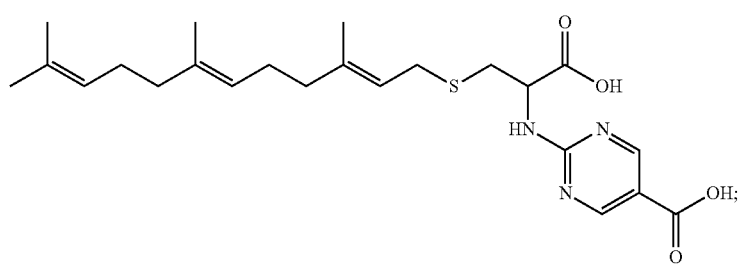 [SMILES: CC(C)=CCC/C(C)=C/CC/C(C)=C/CSCC(Nc1ncc(C(=O)O)cn1)C(=O)O]
BW TABLE 1-continued
Exemplary Compounds
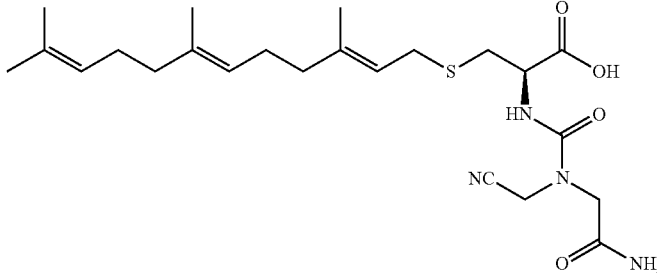
BX
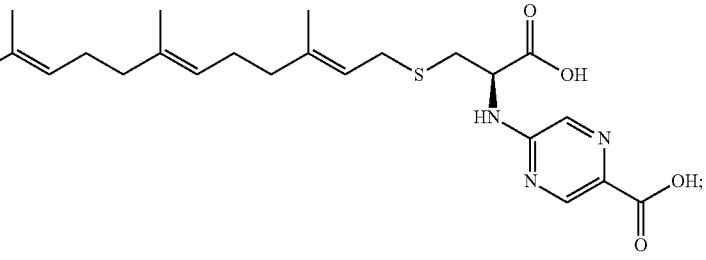
BY
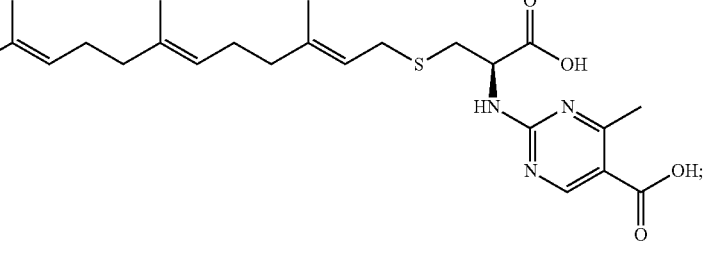
BZ
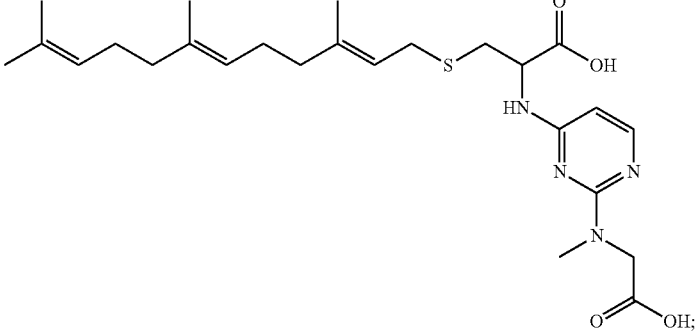
CA
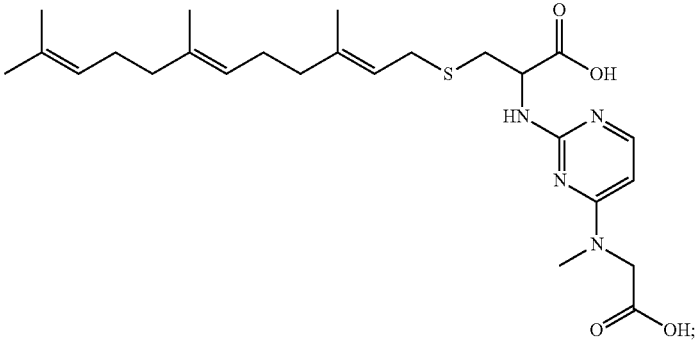 [SMILES: CC(C)=CCC/C(C)=C/CC/C(C)=C/CSCC(Nc1nccc(N(C)CC(=O)O)n1)C(=O)O]
CB TABLE 1-continued Exemplary Compounds

[Structure CC: farnesyl-S-C(CH₃)₂-CH(COOH)-NH-C(O)-CH₂-CH₂-C(O)OH]

CC

[Structure CD: farnesyl-S-C(CH₃)₂-CH(COOH)-NH-(2-pyrimidinyl-5-COOH)]

CD

In certain embodiments, the presently disclosed compounds include any one, or any combination of, the exemplary compounds disclosed below, and pharmaceutically acceptable salts, solvates, prodrugs or esters thereof:

In one embodiment, the presently disclosed compound is compound C, or a pharmaceutically acceptable salt, solvate, prodrug or ester thereof. In one embodiment, the presently disclosed compound is compound E, or a pharmaceutically acceptable salt, solvate, prodrug or ester thereof. In one embodiment, the presently disclosed compound is compound G, or a pharmaceutically acceptable salt, solvate, prodrug or ester thereof.

In one embodiment, compound E, or a pharmaceutically acceptable salt, solvate, prodrug or ester thereof, is excluded as a presently disclosed compound of the present invention. In one embodiment, compound G, or a pharmaceutically acceptable salt, solvate, prodrug or ester thereof, is excluded as a presently disclosed compound of the present invention.

Unless otherwise stated, all tautomeric forms of the presently disclosed compounds are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. Mixtures of isomeric forms may be separated and/or purified by techniques as would be known to one skilled in this art, including but not limited to column chromatography.

The presently disclosed compounds may be provided according to the present invention in any of a variety of useful forms, for example as pharmaceutically acceptable salts, as particular crystal forms, etc. In some embodiments, prodrugs of one or more compounds of the present invention are provided.

In certain embodiments, provided compounds modulate a G-protein signaling cascade. In certain embodiments, provided compounds alter the interactions among polyisoprenylated signal transduction proteins, such as G-proteins and the protein regulatory targets with which they interact, or other intracellular signaling proteins. In certain embodiments, provided compounds modulate the inflammatory response. In certain embodiments, provided compounds inhibit inflammation and are therefore anti-inflammatory.

In some embodiments, provided compounds modulate levels of inflammatory mediators, such as cytokines induced by G-protein-mediated pathways (e.g., purinergic receptors). In some embodiments, provided compounds inhibit the levels of proinflammatory mediators, such as proinflammatory cytokines. In further embodiments, provided compounds inhibit levels of proinflammatory mediators, such as proinflammatory cytokines induced by G-protein-mediated pathways.

In some embodiments, provided compounds modulate levels of inflammatory mediators, such as cytokines induced by other signal transduction pathways [e.g., pathways involving Toll-like receptors ("TLRs") and TNFα receptors]. In some embodiments, provided compounds inhibit levels of proinflammatory mediators, such as proinflammatory cytokines induced by other signal transduction pathways [e.g., pathways involving Toll-like receptors ("TLRs") and TNFα receptors].

In some embodiments, provided compounds inhibit levels of proinflammatory mediators, such as proinflammatory cytokines that are induced by chemicals such as TPA.

In some embodiments, provided compounds modulate the levels of inflammatory mediators such as cytokines characterized using an ovalbumin-induced flaky tail Atopic Dermatis mouse model.

In some embodiments, the presently disclosed compounds modulate the infiltration and accumulation of T-helper lymphocytes. In some embodiments, the presently disclosed compounds modulate T-helper lymphocytes with CD3+ marker. In some embodiments, the presently disclosed compounds modulate the infiltration and accumulation of T-helper lymphocytes characterized using a Stat3c psoriasis mouse model. In some embodiments, the presently disclosed compounds inhibit infiltration and accumulation of T-helper lymphocytes. In some embodiments, the presently disclosed compounds inhibit infiltration and accumulation of T-helper lymphocytes with CD3+ marker. In some embodiments, the presently disclosed compounds inhibit infiltration and accumulation of T-helper lymphocytes characterized using a Stat3c psoriasis mouse model.

In some embodiments, the presently disclosed compounds inhibit methylesterifcation reactions by a specific membrane associated S-adenosylmethionine-dependent isoprenyl-S-isoprenyl methyltransferase ("ICMT") resulting in carboxy-terminal polyisoprenoid cysteine modifications of a number of key factors in G-protein signaling pathway.

In some embodiments, the presently disclosed compounds inhibit oxidative burst from neutrophils and are therefore anti-oxidants.

In certain embodiments, activity of provided compounds may be characterized using a variety of in vitro or in vivo assays, involving a variety of cell-based or animal-based models. For example, data from exemplary assays for: Edema, Erythema and/or Inhibition of Myeloperoxidase; Inflammatory Cytokines; Stat3c-Psoriasis Mouse Model; Inhibition of Methylesterification Reactions; and Inhibition of Oxidative Burst are each described below.

Edema, Erythema and/or Inhibition of Myeloperoxidase (MPO)

Ability of provided compounds to modulate inflammatory responses may be assessed, for example, using assays that assess edema, erythema, and/or inhibition of myeloperoxidase ("MPO") as described, for example, in Example 79 of U.S. Published Application No. 2016/0361283, which is hereby incorporated by reference in its entirety.

In certain embodiments, the presently disclosed compounds are considered to be inhibitors of inflammation when they show a percent inhibition in an edema assay of at least about 30%, about 35%, about 40%, about 50%, about 60%, about 70%, about 80%, about 90 or about 95%, for example when provided at a dose of or about 0.2 mg/20 µl, or at a dose of or about 0.8 mg/20 µL. In certain embodiments, the presently disclosed compounds are considered to be inhibitors of inflammation when they result in an $ED_{50}$ in an edema assay of at least about 0.5, about 1, about 1.5, about 2, about 2.5, about 3, about 3.5, about 4, or about 4.5-fold lower than that observed with AFC.

In certain embodiments, the presently disclosed compounds are considered to be inhibitors of inflammation when they show a percent inhibition in an erythema assay of at least about 25%, about 30%, about 35%, about 40%, about 50%, about 60%, about 70%, about 80%, about 90% or about 95%, for example when provided at a dose of or about 0.2 mg/20 µl, or at a dose of or about 0.8 mg/20 µL. In certain embodiments, the presently disclosed compounds are considered to be inhibitors of inflammation when they result in an $ED_{50}$ in an erythema assay of at least about 0.5, about 1, about 1.5, about 2, about 2.5, about 3, about 3.5, about 4, or about 4.5-fold lower than that observed with AFC.

In certain embodiments, the presently disclosed compounds are considered to be inhibitors of inflammation when they show a percent inhibition in an MPO activity assay of at least about 25%, about 30%, about 35%, about 40%, about 50%, about 60%, about 70%, about 80%, about 90% or about 95%, for example when provided at a dose of or about 02. mg/20 µl, or at a dose of or about 0.8 mg/20 µL. In certain embodiments, the presently disclosed compounds are considered to be inhibitors of inflammation when they result in an $ED_{50}$ in an MPO activity assay of at least about 0.5, about 1, about 1.5, about 2, about 2.5, about 3, about 3.5, about 4, or about 4.5-fold lower than that observed with AFC.

Inflammatory Cytokines (i) TPA-Induced Mouse Ear Inflammatory Model

In certain embodiments, the presently disclosed compounds are considered inhibitors of inflammation when they show a percent inhibition of cytokine release in a TPA-induced mouse ear inflammatory model of at least about 5, 10, 15, 20, 25, 30, 35, 40, 45, 50, 55, 60, 65, 70, 75, 80, 85, 90 or 95%, for example when provided at a dosage of 0.25%. In certain embodiments, the presently disclosed compounds are considered inhibitors of inflammation when they result in an $ED_{50}$ in a TPA-induced mouse ear inflammatory model of at least about 0.01, 0.05, 0.10, 0.15, 0.20, 0.25, 0.30, 0.35 or 0.40 µg cytokine/mouse ear, for example when provided at a dosage of 0.25%. In certain embodiments, the presently disclosed compounds are considered inhibitors of inflammation when they show a percent inhibition of cytokine release in a TPA-induced mouse ear inflammatory model of at least about 5, 10, 15, 20, 25, 30, 35, 40, 45, 50, 55, 60, 65, 70, 75, 80, 85, 90 or 95%, for example when provided at a dosage of 0.50%. In certain embodiments, the presently disclosed compounds are considered inhibitors of inflammation when they result in an $ED_{50}$ in a TPA-induced mouse ear inflammatory model of at least about 0.01, 0.05, 0.10, 0.15, 0.20, 0.25, 0.30, 0.35 or 0.40 µg cytokine/mouse ear, for example when provided at a dosage of 0.50%. In certain embodiments, the presently disclosed compounds are considered inhibitors of inflammation when they show a percent inhibition of cytokine release in a TPA-induced mouse ear inflammatory model of at least about 5, 10, 15, 20, 25, 30, 35, 40, 45, 50, 55, 60, 65, 70, 75, 80, 85, 90 or 95%, for example when provided at a dosage of 1.00%. In certain embodiments, the presently disclosed compounds are considered inhibitors of inflammation when they result in an $ED_{50}$ in a TPA-induced mouse ear inflammatory model of at least about 0.01, 0.05, 0.10, 0.15, 0.20, 0.25, 0.30, 0.35 or 0.40 kg cytokine/mouse ear, for example, when provided at a dosage of 1.00%.

(ii) LPS-TLR4-Induced Cytokine Release Inflammatory Model

In certain embodiments, the presently disclosed compounds are considered inhibitors of inflammation when they show a percent inhibition of cytokine release in a LPS-TLR4-induced cytokine release model, as determined using HMEC-1 cells of at least about 5, 10, 15, 20, 25, 30, 35, 40, 45, 50, 55, 60, 65, 70, 75, 80, 85, 90 or 95%, for example when provided at a dosage of 0.25%. In certain embodiments, the presently disclosed compounds are considered inhibitors of inflammation when they result in an $ED_{50}$ in a LPS-TLR4-induced cytokine release model, as determined using HMEC-1 cells, of at least about 0.01, 0.05, 0.10, 0.15, 0.20, 0.25, 0.30, 0.35 or 0.40 kg cytokine/mouse ear, for example when provided at a dosage of 0.25%. In certain embodiments, the presently disclosed compounds are considered inhibitors of inflammation when they show a percent inhibition of cytokine release in a LPS-TLR4-induced cytokine release model, as determined using HMEC-1 cells, of at least about 5, 10, 15, 20, 25, 30, 35, 40, 45, 50, 55, 60, 65, 70, 75, 80, 85, 90 or 95%, for example when provided at a dosage of 0.50%. In certain embodiments, the presently disclosed compounds are considered inhibitors of inflammation when they result in an $ED_{50}$ in a LPS-TLR4-induced cytokine release model, as determined using HMEC-1 cells, of at least about 0.01, 0.05, 0.10, 0.15, 0.20, 0.25, 0.30, 0.35 or 0.40 kg cytokine/mouse ear, for example when provided at a dosage of 0.50%. In certain embodiments, the presently disclosed compounds are considered inhibitors of inflammation when they show a percent inhibition of cytokine release in a LPS-TLR4-induced cytokine release model, as determined using HMEC-1 cells, of at least about 5, 10, 15, 20, 25, 30, 35, 40, 45, 50, 55, 60, 65, 70, 75, 80, 85, 90 or 95%, for example when provided at a dosage of 1.00%. In certain embodiments, the presently disclosed compounds are considered inhibitors of inflammation when they result in an $ED_{50}$ in a LPS-TLR4-induced cytokine release model, as determined using HMEC-1 cells, of at least about 0.01, 0.05, 0.10, 0.15, 0.20, 0.25, 0.30, 0.35 or 0.40 g cytokine/mouse ear, for example, when provided at a dosage of 1.00%.

(iii) TPA-Induced Cytokine Release Inflammatory Model

In certain embodiments, the presently disclosed compounds are considered inhibitors of inflammation when they show a percent inhibition of cytokine release in a TPA-induced cytokine release model, as determined using NHEK cells of at least about 5, 10, 15, 20, 25, 30, 35, 40, 45, 50, 55, 60, 65, 70, 75, 80, 85, 90 or 95%, for example when provided at a dosage of 0.25%. In certain embodiments, the presently disclosed compounds are considered inhibitors of inflammation when they result in an $ED_{50}$ in a TPA-induced cytokine release model, as determined using NHEK cells, of at least about 0.01, 0.05, 0.10, 0.15, 0.20, 0.25, 0.30, 0.35 or 0.40 µg cytokine/mouse car, for example when provided at a dosage of 0.25%. In certain embodiments, the presently disclosed compounds are considered inhibitors of inflammation when they show a percent inhibition of cytokine release in a TPA-induced cytokine release model, as determined using NHEK cells, of at least about 5, 10, 15, 20, 25, 30, 35, 40, 45, 50, 55, 60, 65, 70, 75, 80, 85, 90 or 95%, for example when provided at a dosage of 0.50%. In certain embodiments, the presently disclosed compounds are considered inhibitors of inflammation when they result in an $ED_{50}$ in a TPA-induced cytokine release model, as determined using NHEK cells, of at least about 0.01, 0.05, 0.10, 0.15, 0.20, 0.25, 0.30, 0.35 or 0.40 µg cytokine/mouse ear, for example when provided at a dosage of 0.50%. In certain embodiments, the presently disclosed compounds are considered inhibitors of inflammation when they show a percent inhibition of cytokine release in a TPA-induced cytokine release model, as determined using NHEK cells, of at least about 5, 10, 15, 20, 25, 30, 35, 40, 45, 50, 55, 60, 65, 70, 75, 80, 85, 90 or 95%, for example when provided at a dosage of 1.00%. In certain embodiments, the presently disclosed compounds are considered inhibitors of inflammation when they result in an $ED_{50}$ in a TPA-induced cytokine release model, as determined using NHEK cells, of at least about 0.01, 0.05, 0.10, 0.15, 0.20, 0.25, 0.30, 0.35 or 0.40 µg cytokine/mouse ear, for example, when provided at a dosage of 1.00%.

(iv) Ovalbumin-Induced Atopic Dermatis Mouse Model

In certain embodiments, the presently disclosed compounds are considered inhibitors of inflammation when they show a percent inhibition of cytokine release in an Ovalbumin-induced Atopic Dermatitis mouse model, of at least about 5, 10, 15, 20, 25, 30, 35, 40, 45, 50, 55, 60, 65, 70, 75, 80, 85, 90 or 95%, for example when provided at a dosage of 0.25%. In certain embodiments, the presently disclosed compounds are considered inhibitors of inflammation when they result in an $ED_{50}$ in an Ovalbumin-induced Atopic Dermatitis mouse model, of at least about 0.01, 0.05, 0.10, 0.15, 0.20, 0.25, 0.30, 0.35 or 0.40 µg cytokine/mouse ear, for example when provided at a dosage of 0.25%.

In certain embodiments, the presently disclosed compounds are considered inhibitors of inflammation when they show a percent inhibition of cytokine release in an Ovalbumin-induced Atopic Dermatitis mouse model, of at least about 5, 10, 15, 20, 25, 30, 35, 40, 45, 50, 55, 60, 65, 70, 75, 80, 85, 90 or 95%, for example when provided at a dosage of 0.50%. In certain embodiments, the presently disclosed compounds are considered inhibitors of inflammation when they result in an $ED_{50}$ in an Ovalbumin-induced Atopic Dermatitis mouse model, of at least about 0.01, 0.05, 0.10, 0.15, 0.20, 0.25, 0.30, 0.35 or 0.40 µg cytokine/mouse ear, for example when provided at a dosage of 0.50%. In certain embodiments, the presently disclosed compounds are considered inhibitors of inflammation when they show a percent inhibition of cytokine release in an Ovalbumin-induced Atopic Dermatitis mouse model, of at least about 5, 10, 15, 20, 25, 30, 35, 40, 45, 50, 55, 60, 65, 70, 75, 80, 85, 90 or 95%, for example when provided at a dosage of 1.00%. In certain embodiments, the presently disclosed compounds are considered inhibitors of inflammation when they result in an $ED_{50}$ in an Ovalbumin-induced Atopic Dermatitis mouse model, of at least about 0.01, 0.05, 0.10, 0.15, 0.20, 0.25, 0.30, 0.35 or 0.40 µg cytokine/mouse ear, for example, when provided at a dosage of 1.00%.

Inhibition of Methylesterification Reactions

For example, ability of the presently disclosed compounds to inhibit methylesterification reactions by ICMT may be assessed, for example, using assays that measure the reduction of methylated acetyl farnesyl cysteine, an ICMT substrate as described for example in Example 87 of U.S. Published Application No. 2016/0361283. In certain embodiments, the presently disclosed compounds are considered inhibitors of ICMT when they show a percent reduction of methylated acetyl-farnesyl-cysteine, as ICMT substrate of at least about 30, 35, 40, 50, 60, 70, 75, 80, 85, 90, 95 or 100%, for example when provided at a concentration of 25 µM.

Inhibition of Oxidative Burst

For example, ability of the presently disclosed compounds to inhibit oxidative burst from neutrophils may be assessed, for example, using assays that measure the reduction of superoxide formation, as described for example in Example 88 of U.S. Published Application No. 2016/0361283. In certain embodiments, the presently disclosed compounds are considered inhibitors of oxidative burst from neutrophils when they show a percent reduction of superoxide formation of at least about 30, 35, 40, 50, 60, 70, 75, 80, 85, 90, 95 or 100%, for example when provided at a concentration of 25 µM.

2. Methods of Syntheses

The present invention provides methods of preparing compounds provided herein. As will be appreciated by one of skill in the art, the synthetic methods described herein may be modified without departing from the scope of the present invention. For example, different starting materials and/or different reagents may be used in the inventive synthetic methods.

Generally, presently provided compounds (e.g., Compounds B, D, F, H and I) can be prepared starting with an appropriately lipidated cysteine (preferably with phytyl or farnesyl moieties) to be added to a solution of the corresponding activated acid (e.g., with HATU [1-[Bis(dimethylamino)methylene]-1H-1,2,3-triazolo[4,5-b]pyridinium 3-oxid hexafluorophosphate] or DCC [N,N'-Dicyclohexylcarbodiimide]) in the presence of an organic base (e.g., trimethylamine or Hünig's base [N,N-Diisopropylethylamine]) to form an amide bond in the end compound. After isolation, these end compounds can be further purified by crashing their sodium salts from alcoholic solution with sodium hydroxide or sodium ethoxide. Overall yield after filtration and drying in vacuum for these end compounds can be, in certain embodiments, in the 30-84% range.

The above method, however, does not produce satisfactory yields for some compounds of the present invention, particularly compounds C, E, G and I. The appropriately lipidated cysteine (preferably with phytyl or farnesyl moieties) did not produce any synthetically useful yields of the end compounds when treated with CDI, triphosgene or phosgene under multiple conditions following introduction of the corresponding secondary amines. Surprisingly, the appropriately lipidated cysteine methyl ester (preferably with phytyl or farnesyl moieties) when treated with CDI in organic solvent (preferably DMF, THF or similar polarity solvent), following by introduction of the corresponding secondary amine and base (preferably trimethylamine or Hünig's base [N,N-Diisopropylethylanine] or inorganic base like $Na_2CO_3$) and gentle heating to 50° C. formed the desired urea moiety in the title compounds in good to excellent yields. After isolation, these compounds were further purified by crashing their sodium salts from alcoholic solution with sodium hydroxide or sodium ethoxide. Overall yield after filtration and drying in vacuum for these compounds prepared in this alternative manner can be in 30-84% range.

3. Compositions and Formulations

The present invention provides compositions comprising compounds as presently described herein. In some embodiments, provided compositions contain additional components. In some embodiments, all such additional components are pharmaceutically acceptable and provided compositions are pharmaceutical compositions suitable for administration to a human or other animal. In some embodiments, all such additional components are cosmetically acceptable and provided compositions are cosmetic compositions. In some embodiments, all such additional components are cosmoceutically acceptable and provided compositions are cosmeceutical compositions.

In general, one or more compounds of the present invention may be formulated into pharmaceutical compositions that include at least one provided compound of the present invention together with one or more pharmaceutically acceptable carriers, including excipients, such as diluents, binders and the like, and additives, such as stabilizing agents, preservatives, solubilizing agents, and buffers, as desired. Formulation excipients may include polyvinylpyrrolidone, gelatin, hydroxy cellulose, acacia, polyethylene glycol, manniton, sodium chloride and sodium citrate. In some embodiments, inventive compositions contain a pharmaceutically acceptable carrier. In some embodiments, the compositions of the present invention include a cosmetically acceptable carrier. In some embodiments, the compositions of the present invention include a cosmeceutically acceptable carrier.

A carrier in certain compositions according to the present invention may include liquid and, in particular may comprise a buffered, isotonic, aqueous solution.

A carrier, including a pharmaceutically acceptable carrier, may be, or include, an excipient, such as a diluent, binder (e.g., binding agent) and the like, and or an additive, such as a stabilizing agent, preservative, solubilizing agent, and/or buffer as hereafter described. Pharmaceutical carriers include, without limitation, a binding agent (e.g., hydroxypropyl methylcellulose, polyvinylpyrrolidone, or pregelatinised maize starch, etc.); a filler (e.g., calcium hydrogen phosphate calcium sulfate, ethyl cellulose, gelatin, lactose and other sugars, microcrystalline cellulose, pectin, polyacrylates, etc.); a disintegrant (e.g., glycolate, sodium starch, starch, etc.); a lubricant (e.g., colloidal silicon dioxide, corn starch, hydrogenated vegetable oils, polyethylene glycols, magnesium stearate, metallic stearates, silica, sodium benzoate, sodium acetate, stearic acid, talc, etc.); or a wetting agent (e.g., sodium lauryl sulphate, etc.). Additional pharmaceutically acceptable carriers include, for example, petroleum jelly (Vaseline®), and petroleum.

Additional suitable carriers for the compositions of the present invention include, but are not limited to, alcohols, amyloses, animal oil, anti-irritants, chelating agents, colorants, deodorant agents, emulsifiers, fragrances, gelatins, hair conditioning agents, hydroxymethylcelluloses, magnesium stearates moisturizing agents (e.g., humectants), microcrystalline, mineral oil, natural polymers (e.g., collagen, gum arabic, polyols, and xanthanes, and the like), organic, ozocerite wax, and inorganic waxes, paraffin, penetration enhancers, pH adjusting agents, preservatives, propellants, salt solutions, silicic acids, surfactants tales, solubilizing agents, thickeners, viscous paraffins, and water, and combinations thereof. In some embodiments, the presently disclosed compounds act as acceptable carrier(s) and/or excipient(s). In certain embodiments, AFC acts as an acceptable carrier and/or excipient, and may be included in compositions containing the presently disclosed compounds. In some embodiments, it may be desirable to use the carriers in cosmetic compositions, as described in the CTFA International Cosmetic Ingredient Dictionary and Handbook, 8th edition, edited by Wenninger and Canterbery, (The Cosmetic, Toiletry, and Fragrance Association, Inc., Washington, D.C., 2000), which is herein incorporated by reference. Also included are the carriers described hereinabove.

In some embodiments, pharmaceutically acceptable carriers of the composition include a sustained release or delayed release carrier. Such carriers can be any material capable of sustained or delayed release of presently disclosed compounds to provide a more efficient administration resulting in less frequent and/or decreased dosage of the presently disclosed compounds, ease of handling, and extended or delayed effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes which may enhance the localized delivery of the compounds of the inventive composition within skin layers, may be formed from a variety of phospholipids, such as cholesterol, stearylamines or phosphatidylcholines.

For injection or other liquid administration formulations, water containing at least one or more buffering constituents is commonly utilized, and stabilizing agents, preservatives and solubilizing agents may also be employed. In some embodiments, a provided pharmaceutical composition is or comprises an isotonic solution.

For solid administration formulations, any of a variety of thickening, filler, bulking and carrier additives may be employed, such as starches, sugars, fatty acids and the like. Topical compositions of the present invention can be applied locally to the skin or mucosa and may be in any form including solutions, oils, creams, ointments, gels, lotions, shampoos, milks, cleansers, moisturizers, sprays, skin patches and the like.

For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a provided compound over a period of time. For example, gelatin, sodium carboxymethylcellulose and/or other cellulosic excipients may be included to provide time-release or slower-release formulations, especially for administration by subcutaneous and intramuscular injection.

In certain embodiments use, the presently disclosed compounds can be combined as the active ingredient in an admixture with a pharmaceutical carrier according to conventional pharmaceutical compounding techniques. Pharmaceutical compositions for the present invention may be formulated for delivery by any of a variety of routes including, for example, oral, parenteral (including intravenous), urethral, vaginal, nasal, topical (e.g., dermal, transdermal), pulmonary, deep lung, inhalation, buccal, sublingual routes, or the like.

In preparing compositions containing the presently disclosed compounds for cutaneous administration, such as topical (i.e., local), such compositions can include pharmaceutical carriers (e.g., sterile and non-sterile aqueous solutions, non-aqueous solutions in common solvents such as alcohols, or solutions of presently disclosed compounds in liquid or solid oil bases). Such pharmaceutical carrier solutions also can contain buffers, diluents and other suitable additives.

Representative compositions suitable for oral use include, for example, mouthwash, rinse, oral spray, suspension, dental gel, and the like. Typical oral carriers known in the art may be used in the present invention. In certain embodiments, the pharmaceutical and/or cosmetic carriers include water, ethanol, or water-ethanol mixtures. Water-ethanol mixtures can be employed in a weight ratio, for example, from about 1:1 to about 20:1, preferably from about 3:1 to about 20:1, and most preferably from about 3:1 to about 10:1, respectively. The pH value of the oral vehicle is generally from about 4 to about 7, and preferably from about 5 to about 6.5. An oral topical vehicle having a pH value below about 4 is generally irritating to the oral cavity and an oral vehicle having a pH value greater than about 7 generally results in an unpleasant mouth feel.

Oral topical inventive compositions may also contain conventional additives normally employed in those products. Conventional additives as described herein include a coloring agents, emulsifiers, fluorine providing compounds, humectants, sweetening agents, and pH adjusting agents, provided that such additives do not interfere with the therapeutic, cosmetically, or cosmeceutically beneficial properties of inventive compositions. Additional ingredients that may be used in compositions of the present invention include fluorine providing compounds, additional active ingredients, new excipients, protectives, and demulcents, as described herein.

Fluorine providing compounds may be fully or slightly water soluble and are characterized by their ability to release fluoride ions or fluoride containing ions in water and by their lack of reaction with other components in the composition. Typical fluorine providing compounds include alkali metal fluorides, inorganic fluoride salts such as water-soluble alkali metal, alkaline earth metal, heavy metal salts, for example, aluminum mono- and di-fluorophosphates, ammonium fluoride, ammonium fluorosilicate, barium fluoride, cuprous fluoride, fluorinated sodium calcium pyrophosphate, potassium fluoride, sodium fluoride, sodium fluorosilicate, sodium fluorozirconate, sodium monofluorophosphate, stannic fluoride, stannous fluoride and zinc fluoride, monofluorophosphates, such as sodium and stannous fluoride, sodium monofluorophosphate, tin fluoride and combinations thereof.

Amounts of fluorine providing compounds present in oral, topical inventive compositions provided herein depend upon the type of fluorine providing compound employed, solubility of the fluorine compound, and the nature of the final oral inventive composition. Amount of fluorine providing compounds used must be a nontoxic amount. In general, fluorine providing compounds when used will be present in an amount up to about 1%, from about 0.001% to about 0.1%, and rom about 0.001% to about 0.05%, by weight of oral topical inventive compositions provided herein.

Typical sweetening agents (sweeteners) that are well known in the art include those that are both natural and artificial sweeteners, may be employed. Sweetening agent used may be selected from a wide range of materials including water-soluble sweetening agents, water-soluble artificial sweetening agents, water-soluble sweetening agents derived from naturally occurring water-soluble sweetening agents, dipeptide based sweetening agents, and protein based sweetening agents, including mixtures thereof.

In some embodiments, compositions of the present invention can further include one or more additional ("compatible", as defined herein) active ingredients which are aimed at providing compositions with another pharmaceutical, cosmetic, or cosmeceutical effect, in addition to that provided by the presently disclosed compound of inventive compositions provided herein.

Additional active ingredients according to the present invention include, without limitation, one or more, in any combination, of a protective agent, an emollient, an astringent, an irritant, a keratolytic, a sun screening agent, a sun tanning agent, an antibiotic agent, an antifungal agent, an antiviral agent, an antiprotozoal agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, a hormone, an anti-dandruff agent, an anti-wrinkle agent, an anti-skin atrophy agent, a sclerosing agent, a cleansing agent, a caustic agent and a hypo-pigmenting agent.

Compositions according to the present invention, which further include one or more additional active ingredients, can therefore be further efficiently used, in addition to their use as a treatment for an epithelial-related condition, in the treatment of any medical, cosmetic and/or cosmeceutical condition in which applying the additional active ingredient is beneficial.

Protectives as described herein may take the form of dusting powders, adsorbents, mechanical protective agents, and plasters. Dusting powders are relatively inert and insoluble materials that are used to cover and protect epithelial surfaces, ulcers and wounds. Usually, these substances are finely subdivided powders that absorb moisture and can act as a dessicant. The absorption of skin moisture decreases friction and also discourages certain bacterial growth. Some of the materials used as protective adsorbents include bentonite, insoluble salts of bismuth, boric acid, calcium carbonate, (precipitated), cellulose, corn starch, magnesium stearate, talc, titanium dioxide, zinc oxide, and zinc stearate.

In some embodiments, protectives also can be administered to the skin to form an adherent, continuous film that may be flexible or semi-rigid depending on the materials and the formulations as well as the manner in which they are applied. This material may serve several purposes including providing occlusion from the external environment, providing chemical support, and serving as vehicles for other medicaments.

In some embodiments, protectives included in compositions of the present invention are demulcents. Demulcents often are applied to the surface in a viscid, sticky preparation that covers the area readily and may be medicated. A number of chemical substances possess demulcent properties.

In practical use, provided compounds herein can be combined as an active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, dermal, transdermal, pulmonary, deep lung, inhalation, buccal, sublingual, or the like.

In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

In some embodiments, one or more of the presently disclosed compounds, carrier and, optionally, additional active ingredients are formed into a composition in the form of a solution, emulsion or gel suspension, as will be further described herein.

In some embodiments, a presently disclosed compound, a pharmaceutical or cosmetic carrier and, optionally, one or more additional active ingredients, are in the form of a solution. A solution can be prepared by mixing a solute or dissolved substance (such as a compound of the invention and, optionally, one or more active ingredient(s)) uniformly throughout a solvent carrier such as water or organic solvents, such as the alcohols (e.g. ethanol or isopropanol, acetone).

In some embodiments, the solution is an aqueous solution wherein a provided compound may be appropriately buffered by means of saline, acetate, phosphate, citrate, acetate or other buffering agents, which may be at any physiologically acceptable pH, generally from about pH 4 to about pH 7. Combinations of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, suitable preservatives may be employed, to prevent or limit bacteria and other microbial growth. One such preservative that may be employed is 0.05% benzalkonium chloride.

In some embodiments, inventive compositions comprising a presently disclosed compound, a carrier and other, optional, ingredients are provided in the form of an emulsion. Emulsions are a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of two phases will not occur unless a third substance, an emulsifying agent, is incorporated. Thus, a basic emulsion in the context of the present invention typically contains two or more components (e.g., two immiscible liquid carriers, an emulsifying agent, and a presently disclosed compound(s)). In some embodiments, a presently disclosed compound can itself be an emulsifying agent, or compositions containing a presently disclosed compound can include an emulsifying agent. Typically, emulsions incorporate an aqueous phase into a non-aqueous phase (or vice versa). However, it is possible to prepare emulsions that are largely non-aqueous, for example, anionic and cationic surfactants of the non-aqueous immiscible system glycerin and olive oil. Exemplary emulsifying agents are described herein.

In some embodiments, inventive compositions including a presently disclosed compound, are provided in the form of gel suspensions, (a semi-solid carrier) or solid carrier to form a paste, powder, ointment, cream, lotion, hydrogel or the like. Exemplary ointments that may be prepared as a gel-suspension include semi-solid preparations intended for external application to the epithelium. Generally, ointment bases are categorized into hydrocarbon bases (oleaginous), which may use white petroleum as a base; adsorption bases (anhydrous), which might use hydrophilic petroleum or anhydrous lanolin; emulsion bases (water and oil type); emulsion bases (oil and water type); and water soluble bases, which often use polyethylene glycol as an ointment base.

Additional compositions of the present invention can be readily prepared using technology known in the art as described in Remington's Pharmaceutical Sciences, $18^{th}$ or $19^{th}$ editions, published by the Mack Publishing Company of Easton, Pa.

In some embodiments, inventive compositions formulated as aqueous suspensions wherein a presently disclosed compound is in admixture with excipients additives and/or suitable for the manufacture of aqueous suspensions. Such additives and/or excipients are suspending agents, for example, sodium carboxymethylcellulose, methylcellulose, hydroxy propylmethylcellulose, sodium alginate, polyvinylpyrrolidone, gum tragacanth, and gum acacia; dispersing or wetting agents may be a naturally occurring phosphatide such as lecithin, or condensation products of an alkylene oxide with fatty acids, for example, polyoxyethylene stearate, or condensation products of ethylene oxide with long chain aliphatic alcohols, for example, heptadecaethyl eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions also may contain one or more coloring agents, one or more flavoring agents, and one or more sweetening agents, such as sucrose or saccharin.

In some embodiments, inventive compositions formulated as oily suspensions by suspending a provided compound in a vegetable oil (e.g., arachis oil, olive oil, sesame oil, coconut oil, or a mineral oil, such as liquid paraffin). Oily suspensions may contain a thickening agent (e.g., beeswax, hard paraffin or cetyl alcohol). Sweetening agents, such as those described herein, and flavoring agents may be added to provide a palatable oral composition. Such compositions may be preserved by the addition of an antioxidant (e.g., ascorbic acid).

In some embodiments, inventive compositions formulated as dispersible powders and/or granules are suitable for compositions of an aqueous suspension by adding water. A presently disclosed compound in such powders and granules can be provided in admixture with a dispersing or wetting agent, suspending agent, and one or more preservatives. Suitable dispersing or wetting agents and suspending agents are exemplified by those already mentioned herein. Additional excipients, for example, sweetening, flavoring and coloring agents also may be incorporated.

Compositions of the invention also may be in the form of oil in water emulsions. The oily phase may be a vegetable oil, for example, olive oil or arachis oil, or a mineral oil, for example a liquid paraffin, or a mixture thereof. Suitable emulsifying agents may be naturally occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

Besides oral and topical compositions, compositions containing the presently disclosed compounds can also be provided, for example, for parenteral and pulmonary administration, as disclosed in U.S. Published Application No. 2016/0361283, which is hereby incorporated by reference.

4. Administration and Dosage Forms

The presently disclosed compounds of the invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, antioxidants and other agents known in the art. In general, any route of administration by which provided compounds of the invention are introduced across an epidermal layer of cells may be employed. Administration means may thus include administration through mucous membranes, buccal administration, oral administration, dermal administration, inhalation administration, pulmonary administration, nasal administration, urethral administration, vaginal administration, and the like.

In general, compositions comprising a therapeutically or pharmaceutically effective amount of an inventive composition including a presently disclosed compound may be formulated for administration in unit dosage forms.

Oral Administration

Because of their ease of administration, tablets and capsules represent an advantageous oral unit dosage form. If desired, a composition including a presently disclosed compound may be coated by standard aqueous or nonaqueous techniques. The amount of active compound, i.e. a presently disclosed compound of the present invention, in such therapeutically useful compositions is such that an effective dosage will be obtained. In another advantageous dosage unit form, sublingual pharmaceutical compositions may be employed, such as sheets, wafers, tablets or the like. Compositions of the present invention may be in additional forms suitable for oral use, for example, troches, lozenges, pills, aqueous or oily suspensions, solutions, dispersible powders or granules, emulsions, hard or soft capsules, syrups or elixirs, pastes, gels or the like.

Topical Administration

Formulations of the present invention suitable for topical application to the skin can take the form of an ointment, cream, lotion, paste, gel, spray, aerosol, or oil. Additives which may be used include vaseline, lanoline, polyethylene glycols, alcohols, transdermal enhancers, and combinations of two or more thereof.

In some embodiments, formulations suitable for topical application achieve transdermal delivery. Transdermal pharmaceutical devices include patches, occlusive dressings, occlusive formulations, hypodermic sprays, iontophoretic systems, gels and infusion pumps, all of which are well known in the art. A transdermal patch which includes a pharmaceutical may generally include a backing layer impermeable to the pharmaceutical, a reservoir to house the pharmaceutical, and an adhesive cover to be removed upon use of the patch and for adhesion to the skin of a patient.

Formulations suitable for transdermal administration may also be presented as medicated bandages or discrete patches adapted to remain in intimate contact with the epidermis of the recipient for a prolonged period of time. Representative examples of suitable transdermal patches include, for example, those developed by NeuroDerm Ltd. (Israel) and/or that used to deliver estradiol, for example, those developed by Novogyne Pharmaceuticals. Formulations suitable for transdermal administration may also be delivered by iontophoresis (passage of a small electric current (15 mA) to "inject" electrically charged ions into the skin) through the skin. For this, the dosage form typically takes the form of an optionally buffered aqueous solution of the active compound, i.e. a presently disclosed compound.

Formulations suitable for transdermal administration may also be delivered by using an infusion pump connected to a needle that is inserted through the skin, for example, those developed by Medtronic used to deliver insulin. Amounts of compound used in a transdermal device as described herein may vary, depending on many factors including the size of the device and its release characteristics, the amount of the pharmaceutical active agent and the estimated duration of action of the device. Broadly, amounts of a presently disclosed compound typically range from about 0.1% to about 10% w/v.

5. Dosage: Therapeutically Effective Amount

The actual quantity of the presently disclosed compounds administered to a patient will vary depending on the severity and type of indication, the mode of administration, the particular compound used, the formulation used, and the response desired.

The dosage for treatment is administration, by any of the foregoing means or any other means known in the art, of an amount sufficient to bring about the desired therapeutic effect. Thus, a therapeutically effective amount may be an amount of a presently disclosed compound or pharmaceutical composition that is sufficient to induce a desired effect, including but not limited to an anti-inflammation effect. Those of ordinary skill in the art will appreciate that a therapeutically effective amount may be administered by means of a single dose or multiple doses, and that compositions provided herein may contain a unit dose of a therapeutically effective amount.

In general, the presently disclosed compounds are highly active. For example, a presently disclosed compound may be administered from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of a presently disclosed compound per subject body weight per day to obtain a desired therapeutic effect. A desired dosage may be delivered to a subject only once. A desired dosage may be delivered more than three times per day, three times per day, two times per day, once per day, every other day, every third day, every week, every two weeks, every three weeks, every four weeks, every two months, every six months, every twelve months, every two years, every three years, every four years, every five years, every 10 years, or every 20 years. In certain embodiments, the desired dosage may be delivered using multiple administrations (e.g., two, three, four, five, six, seven, eight, nine, ten, eleven, twelve, thirteen, fourteen, fifteen, or more administrations). The skilled artisan will appreciate that certain factors can influence the dosage and timing required to effectively treat a subject, including but not limited to the specific compound selected, the desired therapeutic response, the route of administration, the formulation, the severity of the disease or disorder, previous treatments, the general health and/or age of the subject, other diseases present, and/or other factors known to those of skill in the art.

6. Uses

In certain embodiments, the present invention provides novel compounds, which might themselves be added to or combined with other pharmaceutically active agents, compositions comprising at least one presently disclosed compound or combination with other pharmaceutically active agents thereof, and/or methods of their preparation or use in the amelioration, treatment or prevention of, for example, certain conditions, diseases or disorders associated with inflammation or the suppression of inflammatory responses.

In certain particular embodiments, the present invention provides anti-inflammatory compounds and compositions described here that inhibit inflammation and are therefore useful in the treatment of diseases, conditions or disorders associated with inflammation.

In certain embodiments, the present invention provides novel compounds and compositions that modulate inflammation. Although not wishing to be bound by one theory, it is believed that compounds and compositions described herein modulate levels of inflammatory mediators, for example, cytokines. Non-limiting examples of inflammatory mediators modulated by provided compounds and compositions include but are not limited to IL-1α, IL-1β, IL-2, IL-3, IL-4, IL-5, IL-6, IL-7, IL-8, IL-9, IL-10, IL-11, IL-12/IL-23 p40, IL13, IL-17, IL-18, TGF-β, IFN-γ, GM-CSF, Groα, MCP-1 and TNF-α. Although not wishing to be bound by one theory, it is believed that compounds and compositions described herein modulate levels of inflammatory mediators that are associated with a variety of signal transduction pathways. Non-limiting examples of signal transduction pathways that result in release of inflammatory mediators such as cytokines, include but are not limited to G-protein-mediated, PPAR-mediated, Toll-like receptor-mediated, and TNF-α receptor-mediated. Although not wishing to be bound by one theory, it is believed that the presently disclosed compounds modulate T-helper cell infiltration and accumulation. Although not wishing to be bound by one theory, it is believed that the presently disclosed compounds and compositions inhibit oxidative burst from neutrophils and are therefore anti-oxidants.

In certain embodiments, the present invention provides novel compounds and compositions that relate to treating or lessening the severity of one or more diseases in which protein inhibitors that modulate the G-protein signaling cascade are known to play a role. Although not wishing to be bound by one theory, it is believed that the presently disclosed compounds inhibit methylesterifcation reactions by a specific membrane associated S-adenosylmethionine-dependent isoprenyl-S-isoprenyl methyltransferase ("ICMT") resulting in carboxy-terminal polyisoprenoid cysteine modifications of a number of key factors in G-protein signaling pathway. In certain embodiments, the presently disclosed compounds alter the interactions among polyisoprenylated signal transduction proteins, such as G-proteins and the protein regulatory targets with which they interact, or other intracellular signaling proteins.

In certain embodiments, the presently disclosed compounds are administered in vitro. In certain embodiments, such compounds are administered in vivo.

Another aspect of the present invention is directed to methods of treating, preventing, or ameliorating inflammation by administering an effective amount of a presently disclosed compound.

In some embodiments, one or more inventive compounds, alone or together with one or more other pharmaceutically active agents, is used to whiten skin. In some such embodiments, a presently disclosed compound is applied topically to whiten skin.

In general, the actual quantity of provided compounds of the present invention administered to a patient will vary depending on the severity and type of indication, the mode of administration, the particular compound used, the formulation used, and the response desired.

The dosage for treatment is administration, by any of the foregoing means or any other means known in the art, of an amount sufficient to bring about the desired therapeutic effect. Thus, an effective amount includes an amount of a presently disclosed compound (or a mixture of presently disclosed compounds) that is sufficient to induce a desired effect, including specifically, for example, an anti-inflammation effect or a proinflammatory effect depending on the diseases, disorders, conditions, syndromes, and the like, being treated, prevented or promoted.

Methods (A) Anti-Inflammatory

Specifically, the present invention relates to a method of treating or lessening the severity of inflammatory diseases or disorders selected from inflammation (acute or chronic), inflammatory diseases or disorders (e.g., asthma, autoimmune diseases, and COPD including emphysema, chronic bronchitis and small airways disease, etc.), inflammatory responses of the immune system, skin diseases (e.g., reducing acute skin irritation for patients suffering from rosacea, atopic dermatitis, seborrheic dermatitis, psoriasis), irritable bowel syndrome (e.g., Crohn's disease and ulcerative colitis, etc.), Neurodegenerative Disorders (Parkinson's disease, Alzheimer's disease, Huntington's disease, Dementia pugilistica, Pick's disease, Guam parkinsonism dementia complex, Fronto-temporal dementia, Cortico-basal degeneration, Pallido-pontal-nigral degeneration, Progressive supranuclear palsy, Dementia with Lewy bodies (DLB), and multiple system atrophy (MSA)), as well as inflammation associated with spinal cord injury to promote nerve regeneration and inhibition of rejection of genetically engineered cells by the immune system during in vivo gene therapy, wherein the method comprises administering to a patient in need thereof a composition of the present invention that includes one or more of the presently disclosed compounds.

In some embodiments, the presently disclosed compounds of the present invention are capable of effectively inhibiting inflammatory responses. Thus, the presently disclosed compounds are inhibitors of edema, erythema and myeloperoxidase and are therefore useful for treating one or more disorders associated with inflammatory diseases or disorders as described herein.

In some embodiments, the provided anti-inflammatory compounds of the present invention are capable of effectively inhibiting inflammatory responses by decreasing the levels or production of inflammatory mediators such as inflammatory cytokines, for example IL-1α, IL-1β, IL-2, IL-3, IL-4, IL-5, IL-6, IL-7, IL-8, IL-9, IL-10, IL-11, IL-12/IL-23 p40, IL13, IL-17, IL-18, TGF-3, IFN-γ, GM-CSF, Groα, MCP-1 and TNF-α. Thus, the presently disclosed compounds are inhibitors of proinflammatory cytokines and are therefore useful in treating one or more disorders associated with inflammatory diseases, conditions or disorders described herein. Therefore, the presently disclosed compounds are administered to a subject suffering from or susceptible to one or more inflammatory diseases, conditions or diseases.

In some embodiments, the treatment of inflammatory diseases or disorders is achieved using the presently disclosed compounds without having the side effects of corticosteroids or NSAIDS.

In some embodiments, the presently disclosed compounds of the present invention are capable of effective inhibiting oxidative burst response from neutrophils. Thus, the presently disclosed compounds are inhibitors of oxidative burst response and are therefore useful in the treatment or amelioration of symptoms relating to oxidative damage caused by chemical or environmental factor (e.g., UV damage on the skin). Therefore, the presently disclosed compounds are administered to a subject suffering from conditions associated with oxidative damage. In some embodiments, combinations of such sun screening agents with one or more presently disclosed compounds provided herein exhibit antioxidant effects (e.g., inhibition of superoxide formation).

(B) Skin Conditions

In some embodiments, provided herein is a method for treating or preventing a skin condition, the method comprising the step of topically applying onto a surface of a subject, including a human, in need thereof, an effective amount of a composition comprising at least one presently disclosed compound, a carrier and optionally an additional active ingredient. In one particular embodiment, provided herein is a method for treating or preventing a skin condition, the method comprising the step of topically applying onto a surface of a subject, including a human, in need thereof, at least, for example, 0.1 mg of a presently disclosed compound. In a further embodiment, provided herein is a method of promoting healthy skin in a subject, including a human, in need thereof, the method comprising the step of topically applying onto a surface of a subject, including a human, in need thereof, an effective amount of a composition comprising at least one presently disclosed compound, a carrier and optionally an additional active ingredient. In a further embodiment, provided herein is a method of promoting healthy skin in a subject, including a human, in need thereof, the method comprising the step of topically applying onto a surface of a subject, including a human, in need thereof, at least 0.1 mg of a presently disclosed compound.

In a further embodiment, the present invention provides a method for treating or preventing inflammation in a subject, including a human, in need thereof, comprising the step of administering an effective amount of a composition comprising at least one presently disclosed compound, a carrier and optionally an additional active ingredient. In a further aspect, the present invention provides a method for treating or preventing inflammation in a subject, including a human, in need thereof, comprising the step of administering at least 0.1 mg of a presently disclosed compound.

In certain embodiments, the present invention provides uses of a presently disclosed compound in the treatment or prevention of diseases or conditions associated with suppression of inflammatory responses. In certain embodiments, the present invention provides a composition for treating or preventing conditions associated with suppression of the inflammatory responses, in a subject, including a human, in need of treatment thereof, that comprises of at least one a presently disclosed compound, a carrier and optionally, an additional active ingredient. In a further embodiment, provided herein is a method for treating or preventing a disease or condition associated with suppression of inflammatory responses, in a subject, including a human, in need thereof, the method comprising the step of administering an effective amount of a composition comprising at least one presently disclosed compound, a carrier and optionally an additional active ingredient. In a further aspect, provided herein is a method for treating or preventing a disease or condition associated with suppression of inflammatory responses, in a subject, including a human, in need thereof, the method comprising the step of administering at least 0.1 mg of a presently disclosed compound.

Exemplary diseases, disorders or conditions (e.g., rosacea, psoriasis, atopic dermatitis and seborrhic dermatitis) that may be treated with a presently disclosed compound, in accordance with the present invention are addressed individually below.

Rosacea

Rosacea is a chronic, inflammatory skin disorder that afflicts about 14 million people in the US (FoxAnalytics, *The Dermatology Market Outlook to* 2011, B.I. LTD, Editor: London, UK, p. 201; Crandall, M. A. *Market Intelligence Report*, K. Information, Editor, 2008: New York. p 359). With peak onset between the ages of 51 and 60, its incidence will grow substantially in the years ahead. The condition is characterized by a constellation of symptoms that include central facial erythema, telangiectasias, papules, granulomatous nodules, phyma formation and ocular changes. Flares and remissions occur without rationale. There are no known cures for rosacea. Exemplary cytokines associated with rosacea may include TNFα, ILβ, IL-6, IL-8, MCP-1 and Groα.

Psoriasis

Psoriasis is a chronic inflammatory skin disease affecting about 125 million people worldwide and approximately 2-3% of the general population in the US and Europe (Crandall, M. A. *Market Intelligence Report*, K. Information, Editor, 2008: New York. P. 359; Naldi, L., *Curr. Drug Targets Inflamm. Allergy,* 2004, 3: 121-128). Although the pathogenesis of psoriasis has not been fully elucidated, recent advances demonstrate targeting key mediators of inflammation as a promising therapeutic approach (Numerof et al., *BioDrugs,* 2006, 20: 93-103; Menter et al., *J. Am. Acad. Dermatol.,* 2009, 60: 643-659). Direct therapeutic approaches include using antibodies or soluble receptors (i.e., biologics) to directly neutralize the specific cytokine of interest. However, biologic cytokine-derived therapies are expensive to produce, require sustained high blood levels in order to develop significant skin levels, may induce the production of neutralizing antibodies (leading to a diminished response to therapy), and must be administered by injection. Topical treatments have largely been ineffective, so market growth has been driven by systemic agents that have serious potential side effects. Corticosteroids remain the cornerstone of current topical treatment, but they are far from ideal. Long-term steroid use brings safety concerns ranging from issues of systemic absorption to cutaneous atrophy and its various clinical presentations. Today's US market for psoriasis treatments is greatly underserved, as only 60% of sufferers are being treated (Horn et al., *J. Am. Acad. Dermatol.* 2007, 57: 957-962).

Psoriasis can be conceived in simple terms, as a self-reinforcing loop, in which deregulated inflammatory activity stimulates the epidermal Stat3c signaling pathway in the epidermis resulting in epidermal hyperplasia. The affected keratinocytes secrete cytokines which simulate the immune system, including T-helper cell (THc) infiltration and accumulation. Cytokines from the activated immune cells positively feedback on to the epidermal Stat3c pathway maintaining and amplifying the pathophysiology. Inhibition of THc infiltration and accumulation would decrease Stat3c expression and the onset of psoriasis. Exemplary cytokines associated with psoriasis may include TNFα, IL1α, ILβ, IL-2, IL-6, IL-8, IL-12, IL-17, MCP-1, Groα and IFNγ.

Inflammatory Cytokines and Psoriasis

In some embodiments, the present invention provides methods of treating, ameliorating, controlling, or preventing inflammatory skin conditions such as psoriasis comprising administering to a subject in need thereof a dosage form comprising at least about 0.1 mg of a presently disclosed compound, wherein cytokine levels and/or activity (e.g., TNF-α levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a presently disclosed compound, wherein cytokine levels and/or activity (e.g., IL-α levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a presently disclosed compound, wherein cytokine levels and/or activity (e.g., IL-β levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a presently disclosed compound, wherein cytokine levels and/or activity (e.g., IL-2 levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a presently disclosed compound, wherein cytokine levels and/or activity (e.g., IL-6 levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a presently disclosed compound, wherein cytokine levels and/or activity (e.g., IL-8 levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a presently disclosed compound, wherein cytokine levels and/or activity (e.g., IL-12 levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a presently disclosed compound, wherein cytokine levels and/or activity (e.g., IFN-γ levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a presently disclosed compound, wherein cytokine levels and/or activity (e.g., MCP-1 levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a presently disclosed compound, wherein cytokine levels and/or activity (e.g., Gro-α levels and/or activity) are reduced by more than about 20% (e.g., as determined using a K5.Stat3c psoriasis mouse model).

In some embodiments, the present invention provides methods of treating, ameliorating, controlling, or preventing inflammatory skin conditions such as psoriasis comprising administering to a subject in need thereof a dosage form comprising at least about 0.1 mg of a presently disclosed compound, having an activity in the inhibition of (more than about 20%) of levels of CD3+ T-helper cells, determined using a K5.Stat3c psoriasis mouse model.

Atopic Dermatitis

Atopic dermatitis, or eczema, is characterized by chronic inflammation and irritation of the skin. Its causes are varied but immunological in nature. In the US, prevalence is 10% to 20% in children and 1% to 3% in adults. Topical dermatitis is caused by exposure to substances such as poison ivy, detergents and cosmetics that trigger allergic skin reactions. According to present theories, atopic dermatitis is thought to be caused by skin barrier defects that lead to increased exposure to substances such as allergens exposed by inhalation or ingestion. When dermatitis occurs, corticosteroids are the primary treatment. Atopic dermatitis, however, disproportionately affects children, and long-term steroid use in this population raises safety concerns. Exemplary cytokines associated with atopic dermatitis include but are not limited to TNFα, IL1β, IL-6, IL-8, MCP-1, Groα, IL-4, IL-5, IL-10, IL-13, IL-17 and IFNγ.

Histopathology of atopic dermatitis (AD) skin lesions reveals an intense mononuclear cell infiltrate in the dermis with T cells playing a critical role in inducing and maintaining inflammatory cutaneous conditions. While not bound by any particular theory, in the acute stage of AD, the predominant phenotype is a Th2/Th17 immune response, while chronic AD lesions are primarily Th1. The cytokines produced in these skewed immune responses are targets for therapeutic intervention. Activation of Toll-like receptor-4 (TLR4) signaling via several ligands (e.g. Ni2+, *S. aureus*, and LPS) in endothelial cells, keratinocytes and monocytes also contributes to the developing inflammatory response that results in atopic dermatitis. Thus, effectively targeting both TLR and Th1/Th17/Th2 cytokine signaling, which is provided in embodiments of the present invention by administering present compounds to a subject, provides a novel therapeutic approach for topically treating atopic dermatitis.

The present compounds (e.g., Compound C) target both TLR cytokine signaling and Th1/Th17/Th2 cytokine signaling, multiple targets in atopic dermatitis pathogenesis. As discussed in greater detail in the Examples, the presently disclosed compounds (e.g., Compound C) are shown in multiple cell-based assays targeting key pro-inflammatory cytokines that drive AD allergic pathogenesis. In human PBMCs, the present compounds inhibit IL-4 cytokine release elicited by CD3/CD28 and abrogates a $Ni^{2+}$-TLR4 response in endothelial cells by reducing IL-6. In NHEKs, the present compounds inhibit *S. aureus*-induced release of TSLP. Activity in vitro is equal to or more potent than topical AD therapies, AN2728, with the possible exception of the inhibition of IL-4 induction by AN2728. Allergic responses are characterized by early and late phases, possibly representing different inflammatory pathways.

While not being bound by any particular theory, it is believed that strong inhibition of IL-6 production will prove particularly effective to treat the early inflammatory phase of AD. Utilizing in vivo models, the present compounds (e.g. Compound C) exhibit anti-inflammatory activity in the TPA acute inflammation car model. Moreover, in the delayed type hypersensitivity (DTH) oxazolone mouse model, which involves both early and late phases, the present compounds are shown to have higher potency than AN2728, reducing edema and have similar effect on blocking IL-4 production, possibly due to the present compound's greater effect on early phase pathways.

Inflammatory Cytokines and Atopic Dermatitis

According to one aspect, the present invention provides methods of treating, ameliorating, controlling, or preventing inflammatory skin conditions such as atopic dermatitis comprising administering to a subject in need thereof a dosage form comprising at least about 0.1 mg of a presently disclosed compound, wherein cytokine levels and/or activity (e.g., TNF-α levels and/or activity) are reduced by more than about 20% (e.g., as determined using an oxazolone-challenged atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a presently disclosed compound, wherein cytokine levels and/or activity (e.g., IL-α levels and/or activity) are reduced by more than about 20% (e.g., as determined using an oxazolone-challenged atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a presently disclosed compound, wherein cytokine levels and/or activity (e.g., IL-β levels and/or activity) are reduced by more than about 20% (e.g., as determined using an oxazolone-challenged atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a presently disclosed compound, wherein cytokine levels and/or activity (e.g., IL-2 levels and/or activity) are reduced by more than about 20% (e.g., as determined using a oxazolone-challenged atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a presently disclosed compound, wherein cytokine levels and/or activity (e.g., IL-6 levels and/or activity) are reduced by more than about 20% (e.g., as determined using an oxazolone-challenged atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a presently disclosed compound, wherein cytokine levels and/or activity (e.g., IL-8 levels and/or activity) are reduced by more than about 20% (e.g., as determined using an oxazolone-challenged atopic dermatitis mouse model).

According to one aspect, the present invention provides methods of treating, ameliorating, controlling, or preventing inflammatory skin conditions such as atopic dermatitis comprising administering to a subject in need thereof a dosage form comprising at least about 0.1 mg of a presently disclosed compound, wherein cytokine levels and/or activity (e.g., IL-12 levels and/or activity, IFN-γ levels and/or activity, MCP-1 levels and/or activity or Gro-α levels and/or activity) are reduced by more than about 20% (e.g., as determined using an oxazolone-challenged atopic dermatitis mouse model).

Seborrhic Dermatitis

Seborrheic dermatitis, commonly called dandruff, is a disease that causes redness, itchiness, and flaking of the skin. It affects the scalp, face, trunk, and particularly the sebum-gland rich areas of the skin, usually causing the skin to look inflamed and scaly.

Seborrheic dermatitis most often occurs in adults from 30 to 60 years of age and is more common in men than in women. Although the exact cause is not known, those afflicted with seborrheic dermatitis often have an unfavorable epidermic response caused by infections. Seborrheic dermatitis has also been linked to neurologic disorders such as Parkinson's disease and epilepsy. The treatment of seborrheic dermatitis depends on its location on the body. Treatment also depends on the person's age. Dandruff is often treated with a shampoo that contains salicylic acid, the prescription medicine selenium sulfide, zinc pyrithione, ketoconazole or coal tar. Steroid lotions may be used in adolescents and adults. Exemplary cytokines associated with seborrhic dermatitis include, but are not limited to, TNFα, ILβ, IL-6, IL-8, MCP-1, and Groα.

Inflammatory Cytokines and Rosacea, Psoriasis, Atopic Dermatitis and Seborrhic Dermatitis As described herein, the present invention provides methods of treating ameliorating, controlling, or preventing inflammatory skin conditions (e.g., rosacea, psoriasis, atopic dermatitis and seborrhic dermatitis).

In some embodiments, the present invention provides methods of treating ameliorating, controlling, or preventing inflammatory skin conditions (e.g., rosacea, psoriasis, atopic dermatitis and seborrhic dermatitis) by administering a presently disclosed compound, provided that at least 0.1 mg of the compound is administered. In other embodiments, the present invention provides methods of treating ameliorating, controlling, or preventing inflammatory skin conditions (e.g., rosacea, psoriasis, atopic dermatitis and seborrhic dermatitis) by administering a presently disclosed compound, provided that at least 2 mg of the compound is administered.

According to one aspect, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein inflammatory activity (e.g., MPO activity) is reduced by more than about 30% (e.g., as determined using an MPO activity assay).

According to one aspect, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein inflammatory activity (e.g., MPO activity) is reduced by more than about 60% (e.g., as determined using an MPO activity assay).

According to one aspect, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein inflammatory activity (e.g., erythema activity) is reduced by more than about 30% (e.g., as determined using an erythema activity assay).

According to one aspect, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein inflammatory activity (e.g., edema activity) is reduced by more than about 30% (e.g., as determined using an edema activity assay).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., TNF-α, levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-1β levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-8 levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrheic dermatitis) comprising administering to a subject in need thereof a dosage form comprising at least about 0.1 mg of a presently disclosed compound, wherein cytokine levels and/or activity (e.g., IL-6 levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., MCP-1 levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., Groα levels and/or activity) are reduced by more than about 20% (e.g., as determined using a TPA-induced mouse ear inflammatory model).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., TNF-α levels and/or activity) are reduced by more than about 20% (e.g., as determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-1β levels and/or activity) are reduced by more than about 20% (e.g., as determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-8/KC levels and/or activity) are reduced by more than about 20% (e.g., as, determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-6 levels and/or activity) are reduced by more than about 20% (e.g., as determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., MCP-1 levels and/or activity) are reduced by more than about 20% (e.g., as determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., Gro-$\alpha$ levels and/or activity) are reduced by more than about 20% (e.g., as determined using an LPS-TLR4-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., TNF-$\alpha$ levels and/or activity) are reduced by more than about 20% (e.g., as determined using an ATP$\gamma$S-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-10 levels and/or activity) are reduced by more than about 20% (e.g., as determined using an ATP$\gamma$S-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrheic dermatitis) comprising administering to a subject in need thereof a dosage form comprising at least about 0.1 mg of a presently disclosed compound, wherein cytokine levels and/or activity (e.g., IL-8/KC levels and/or activity) are reduced by more than about 20% (e.g., as determined using an ATP$\gamma$S-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-6 levels and/or activity) are reduced by more than about 20% (e.g., as determined using an ATP$\gamma$S-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., MCP-1 levels and/or activity) are reduced by more than about 20% (e.g., as determined using an ATP$\gamma$S-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., Gro-$\alpha$ levels and/or activity) are reduced by more than about 20% (e.g., as determined using an ATP$\gamma$S-purinergic receptor-induced cytokine release inflammatory model in HMEC-1 cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., TNF-$\alpha$ levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-1$\beta$ levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-8/KC levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-6 levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., MCP-1 levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., Gro-α levels and/or activity) are reduced by more than about 20% (e.g., as determined using a TPA-induced cytokine release inflammatory model in NHEK cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., TNF-α levels and/or activity) are reduced by more than about 20% (e.g., as determined using a TNFα-induced cytokine release inflammatory model in HUVEC cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-1β levels and/or activity) are reduced by more than about 20% (e.g., as determined using a TNFα-induced cytokine release inflammatory model in HUVEC cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity are reduced by more than about 20%, such as IL-8/KC, determined using a TNFα-induced cytokine release inflammatory model in HUVEC cell line.

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., IL-6 levels and/or activity) are reduced by more than about 20% (e.g., as determined using a TNFα-induced cytokine release inflammatory model in HUVEC cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., MCP-1 levels and/or activity) are reduced by more than about 20% (e.g., as determined using a TNFα-induced cytokine release inflammatory model in HUVEC cell line).

In some embodiments, the present invention provides methods of treating, ameliorating, controlling, or preventing inflammatory skin conditions (e.g., rosacea, psoriasis, atopic dermatitis and seborrhic dermatitis) comprising administering to a subject in need thereof a dosage form comprising at least about 0.1 mg of a presently disclosed compound, wherein cytokine levels and/or activity (e.g., Gro-α levels and/or activity) are reduced by more than about 20% (e.g., as determined using a TNFα-induced cytokine release inflammatory model in HUVEC cell line).

Sun Screen (Protection from UV Damage)

Oxidative stresses caused by environmental insults such as ultraviolet ("UV") rays from the sun, cigarette smoke exposure, consumption of foods with high saturated fat and environmental pollutants as well as the natural process of aging, contributing to the generation of free radicals and reactive oxygen species ("ROS"), stimulate inflammatory responses, especially in the skin (Pilla et al. Intl J. Cosm. Sci. 2005 v27 p 17-34). High levels of ROS contribute to adverse effects on the skin including erythema, edema, photoaging and skin cancer (Trouba et al. Antioxid. Redox Signal 2002 v4 p 665-673). Neutrophil infiltration during inflammatory responses is associated with increased oxygen consumption and generation of ROS. Extracellular inflammatory agonists such as fMLP bind to GPCRs such as formyl peptide receptors ("FPR"), to trigger the oxidative burst response (i.e., the rapid release of ROS).

In certain embodiments, the present invention provides methods of treating, ameliorating, controlling, or preventing UV damage to especially the skin of a subject, in need thereof, by administering a presently disclosed compound. In certain embodiments, at least 0.1 mg of a presently disclosed compound is administered to treat, ameliorate, control, or prevent UV damage. In certain embodiments, the present invention provides methods of treating, ameliorating, controlling, or preventing UV damage to especially the skin of a subject, in need thereof, by administering at least 2 mg of a presently disclosed compound.

According to one embodiment, the present invention provides methods of treating, ameliorating, controlling, or preventing UV damage to especially the skin of a subject, in need thereof, comprising administering to a subject in need thereof a dosage form comprising at least about 0.1 mg of a presently disclosed compound, having an activity in the inhibition of more than about 20% of superoxide formation.

(C) Anti-Bacterial

The presently disclosed compounds exhibit anti-bacterial activity and are useful in the inhibition of bacterial cell growth or bacterial cell death or bacterial decolonization from surfaces. Thus, in certain embodiments, the presently disclosed compounds are useful in the inhibition of bacterial cell growth or bacterial cell death or bacterial decolonization from surfaces, and/or in the treatment, prevention and management of bacterial-associated conditions.

In some embodiments, the present invention provides, inter alia, methods to treat, prevent or ameliorate the symptoms of epithelial-related diseases, disorders, or conditions, caused or aggravated by bacteria in animals, particularly humans, in need of treatment thereof. In some embodiments, provided methods are useful for epithelial-related conditions (e.g. skin conditions, respiratory conditions, nasal conditions, ocular conditions, oral conditions, conditions of the external ear, vaginal conditions, genitourinary conditions, rectal conditions, bacterial-related conditions of similar tissues, etc.).

In some embodiments, exemplary skin conditions caused or aggravated by bacteria include, but are not limited to, impetigo; acne vulgaris; eczema; atopic dermatitis; infective dermatitis; psoriasis; rosacea; erythema; necrotizing cellulitis; cutaneous anthrax; cellulitis; erysipelas; ecthyma; cutaneous anthrax; necroticizing fasciitis; gangrene; septicaemia; pyoderma; endocarditis; toe web infections; sycosis barbae; furuncles and carbuncles; Staphylococcal scalded skin syndrome; blistering distal dactylitis; acute paronychia; folliculitis; cutaneous diphtheria; erythrasma; and bacterial colonization of open wounds (e.g., cuts, lesions, scrapes, burns, lacerations, chronic wounds, infected animal bites, ulcerations, etc.).

In some embodiments, exemplary respiratory conditions caused or aggravated by bacteria include, but are not limited to, pneumonia; hypersensitivity pneumonitis; upper and lower respiratory tract infections (e.g., secondary bacterial infections in chronic bronchitis, asthma, etc.); chronic obstructive pulmonary disease; diphtheria; bronchopulmonary dysplasia; pertussis; legionellosis (e.g., Legionnaires' disease, Pontiac fever; pharyngitis, etc.).

In some embodiments, exemplary nasal conditions caused or aggravated by bacteria include bacterial rhinitis; paranasal sinusitis, etc.

In some embodiments, exemplary ocular conditions caused or aggravated by bacteria include chronic blepharitis; endophthalmitis, etc.

In some embodiments, exemplary oral conditions caused or aggravated by bacteria include gingivitis; dental caries; early childhood caries, etc.

In some embodiments, exemplary conditions of the external ear caused or aggravated by bacteria include otitis media, etc.

In some embodiments, exemplary vaginal conditions caused or aggravated by bacteria include bacterial vaginosis; chanchroid; syphilis; donovanosis; gonorrhea; lymphogranuloma venereum; non-gonococcal urethritis; staphylococcal infection, vulvovaginitis; etc.

In some embodiments, exemplary genitourinary conditions caused or aggravated by bacteria include for example, Granuloma inquinale, perianal infections, etc.

In some embodiments, bacteria inhibited by the presently disclosed compounds include Gram positive bacteria. In some embodiments, bacteria inhibited by the presently disclosed compounds include Gram negative bacteria. In some embodiments, bacteria inhibited by the presently disclosed compounds include Gram variable bacteria. Particularly relevant Gram positive bacteria include, for example, *Actinomyces* sp. (e.g., *Actinomyces israelli*, etc.); *Bacillus* sp. (e.g., *Bacillus anthracis*, etc.); *Corynebacterium* sp. (e.g., *Corynebacterium diphtheriae*, etc.); *Enterococcus* sp. (e.g., *Enterococcus faecalis*, etc.); *Gardnerella* sp. (e.g., *Gardnerella vaginalis*, etc.); *Mobiluncus* sp. (e.g., *Mobiluncus curtisii, Mobiluncus mulieris*, etc.); *Mycobacterium* sp. (e.g., *Mycobacterium immunogenum, Mycobacterium tuberculosis*, etc.); *Mycoplasma* sp. (e.g., *Mycoplasma pneumonia, Mycoplasma hyopneumoniae, Mycoplasma gallisepticum, Mycoplasma synoviae, Mycoplasma meleagridis, Mycoplasma gallinarum, Mycoplasma anatis, Mycoplasma hominis*, etc.); *Nocardia* sp. (e.g., *Nocardia asteroides, Nocardia brasiliensis, Nocardia caviae*, etc.); *Propionibacterium* sp. (e.g., *Propionibacterium acnes, Propionibacterium propionicus, Propionibacterium freudenreichii*, etc.); *Staphylococcus* sp. (e.g., *Staphylococcus aureus, Staphylococcus pseudintermedius, Staphylococcus epidermidis, Staphylococcus saprophyticus, Staphylococcus pyogenes*, etc.); *Streptococcus* sp. (e.g., *Streptococcus pneumoniae, Streptococcus mutans, Streptococcus mitis, Streptococcus salivarius, Streptococcus pyogenes*, etc.).

Particularly relevant Gram negative bacteria include, for example, *Actinobacillus* sp. (e.g., *Actinobacillus pleuropneumoniae*, etc.); *Bordatella* sp. (e.g., *Bordatella pertussis*, etc.); *Branhamella* (*Moraxella*) sp. (e.g., *Branhamella catarrhalis*, etc.); *Calymmatobacterium* sp. (e.g., *Calymmatobacterium granulomatis*, etc.); *Chlamydia* sp. (e.g., *Chlamydia trachomatis*, etc.); *Chlamydophila* sp. (e.g., *Chlamydophila pneumoniae*, etc.); *Eikenella* sp. (e.g., *Eikenella corrodens*, etc.); *Enterobacter* sp. (e.g., *Enterobacter aerogenes, Enterobacter cloacae*, etc.); *Escherichia* sp. (e.g., *Escherichia coli*, etc.); *Fusobacterium* sp. (e.g., *Fusobacterium nucleatum*, etc.); *Gardnerella* sp. (e.g., *Gardnerella vaginalis*, etc.); *Haemophilus* sp. (e.g., *Haemophilus influenza, Haemophilus ducreyi*, etc.); *Histophilus* sp. (e.g., *Histophilus somnus*, etc.); *Klebsiella* sp. (e.g., *Klebsiella pneumoniae*, etc.); *Legionella* sp. (e.g., *Legionella pneumophila*, etc.); *Mannheimia* sp. (e.g., *Mannheimia haemolytica*, etc.); *Neisseria* sp. (e.g., *Neisseria gonorrhoeae*, etc.); *Ornithobacterium* sp. (e.g., *Ornithobacterium rhinotracheale*, etc.); *Pasteurella* sp. (e.g., *Pasteurella multocida*, etc.); *Pneumocystis* sp. (e.g., *Pneumocystis carinii*, etc.); *Prevotella* sp. (e.g., *Prevotella melaninogenica, Prevotella intermedia*, etc.); *Proteus* sp. (e.g., *Proteus vulgaris, Proteus mirabilis, Proteus penneri*, etc.); *Psuedomonas* sp. (e.g., *Psuedomonas aeruginosa*, etc.); *Treponema* sp. (e.g., *Treponema pallidum*, etc.); *Ureaplasma* sp. (e.g., *Ureaplasma urealyticum*, etc.); *Vibrio* sp. (e.g., *Vibrio vulnificus*, etc.); *Yersinia* sp. (e.g., *Yersinia pestis*, etc.), etc. Particularly relevant Gram variable bacteria include, for example, *Gardnerella* sp. (e.g., *Gardnerella vaginalis*, etc.).

In some embodiments, the present invention provides, inter alia, methods to treat, prevent or ameliorate the symptoms of acne. *Propionibacterium acnes* (*P. acnes*) is a major contributing factor to acne vulgaris, a common disorder among postpubescent teens that is estimated to affect 9.4% of the global population.

Comedones, the primary acne lesions, are the result of abnormal follicular keratinization related to excessive sebum secretion. *P. acnes* colonize and proliferate within the pilosebaceous follicles causing the induction of a local inflammatory response. This is mediated through the interaction of *P. acnes* with epidermal keratinocytes leading to activation of toll-like receptor (TLR2) and later resulting in the production and secretion of pro-inflammatory mediators. More particularly, the interaction of bacterial cell-wall components including peptidoglycan (PGN) and lipopolysaccharides (LPS) with keratinocytes (NHEK) leads to an innate immune response via activation of toll-like receptors (TLR2, TLR4) resulting in the production and secretion of pro-inflammatory mediators.

In certain embodiments of the present invention, presently disclosed compounds down regulate these inflammatory signaling pathways and directly decrease *P. acnes* viability. As detailed in greater detail in the Examples, cultured human keratinocytes were exposed to *P. acnes* and peptidoglycan (PGN) to induce pro-inflammatory cytokine production. In these cell-based models, compounds of the present invention (e.g., compounds E and G) inhibit IL-8 production versus both TLR2 inducers. In an in vitro growth inhibition assay of cultured *P. acnes*, presently disclosed compounds outperform commonly applied anti-acne agents, benzoyl peroxide and salicylic acid, exhibiting a minimal inhibitory concentration (MIC) of 3-4 μg/mL. These data demonstrate that presently disclosed compounds represent a novel chemical-class that provides a dual modulating anti-acne benefit by (a) limiting *P. acnes* bacterial proliferation and (b) inhibiting inflammation by down regulating inflammatory signaling pathways (e.g., activation of toll-like receptors (TLR2, TLR4) resulting in the production and secretion of pro-inflammatory mediators).

7. Combination Therapy

It is contemplated that a presently disclosed compound can be used in combination with other drugs or therapeutic agents.

In some embodiments, a presently disclosed compound as described herein are administered in combination with one or more other agents intended to treat the same condition, or disease. As used herein, additional therapeutic agents that are normally administered to treat a particular disease, or condition, are known as "appropriate for the disease, or condition, being treated."

For example, in some embodiments, compounds of the present invention, or a pharmaceutically acceptable composition thereof, are administered in combination with other anti-inflammatory agents to treat inflammatory diseases and/or disorders. Examples of known anti-inflammatory agents include, but are not limited to, dexamethasone, indomethacin and clobetasol.

In some embodiments, a presently disclosed compound is administered in combination with one or more other pharmaceutically active agents intended to treat a different disease, disorder, or condition. For example, in some embodiments, it may be desirable to administer a presently disclosed compound in order to reduce inflammation while concurrently administering a different pharmaceutically active agent in order to achieve a different biological result.

To give but one example, it is not uncommon that a skin irritating agent (e.g., sodium dodecyl sulfate) be administered prior to or concurrent with application of a transdermal device such as, for example, a transdermal patch, in order to facilitate the delivery. Alternatively, addition or co-administration of a presently disclosed compound in combination with transdermal administration of another pharmaceutically active agent can reduce inflammation and/or irritation associated with the transdermal administration of the other pharmaceutically active agent.

It is also known that single or chronic injections of a pharmaceutically active agent may sometimes result in inflammation, whether due to the identity of the pharmaceutically active agent (i.e., as an irritant) or to the mode of delivery. The present invention contemplates co-administration of one or more compounds of the present invention, in order to reduce inflammation associated with single or chronic injection of a pharmaceutically active agent.

Exemplary pharmaceutically active agents whose delivery, whether transdermally or by injection, may cause skin irritation include levadopa, pro-drug forms of levadopa, insulin, estradiol, estrogen, progesterone, progestins, progestogen, testosterone, nicotine, nitroglycerin, cholinesterase inhibitors, stimulants, antidepressants, and analgesics.

To give another example, application of certain agents such as, for example, hair relaxants, which commonly are or contain basic agents (e.g., NaOH), can cause skin irritation (e.g., irritation and/or inflammation of the scalp). According to the present invention, one or more presently disclosed compound can be administered together with such a hair relaxant (or other agent) to reduce skin irritation and/or inflammation.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

EXAMPLES

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all classes, subclasses and species of each of these compounds, disclosed herein.

Example 1

Synthesis of disodium(2R)-2-{[(carboxylatomethyl)(methyl)carbamoyl]amino}-3-{[(2E)-3,7,11,15-tetramethylhexadec-2-en-1-yl]sulfanyl}propanoate A solution of toluene (99.5+%, CAS [108-88-3], Aldrich) and phosphorous tribromide (99+%, CAS [7789-60-8], Aldrich) is added to a mixture of a commercially phytol (97%, CAS [7541-49-3], toluene, and triethylamine (99.5+%, CAS [121-44-8], Aldrich) at a controlled rate keeping the temperature in the pot below 10° C. The mixture is warmed to 20-25° C. and sampled for reaction completion. The reaction is quenched with agitation by the addition of water, keeping the temperature below 25° C. The mixture is stirred to dissolve all phosphorous acid amine salts and then allowed to settle. The lower aqueous layer is split off and the organic layer washed with 15% brine, settled, and split. The organic layer is recovered and then vacuum stripped to remove the toluene from the desired phytyl bromide. Commercial L-cysteine methyl ester (98%, [18598-63-5], Aldrich) and isopropanol (99.5%, [67-63-0], Aldrich) are charged to a kettle at 24° C. Sodium carbonate (99.5%, powder, [497-19-8], Aldrich) is added through a star valve to form the sodium salt of L-cysteine plus carbon dioxide. The mixture is then vigorously stirred and phytyl bromide is added slowly. The mixture is sampled for reaction completion and then isopropanol is removed under reduced pressure. Water is added to quench the reaction and dissolve the solids and then pH is adjusted to 7 with 2N HCl. The mixture is stirred for 30 min to ensure complete hydrolysis of any traces of phytyl bromide (monitored by HPLC), settled, and the amorphous solid is separated by filtration. The solid is dissolved in the THF (>99.9%, [109-99-9] Aldrich) and CDI (>97%, [530-62-1], Aldrich) are added, followed by addition of triethylamine (99.5+%, CAS [121-44-8], Aldrich). Finally, sarcosine methyl ester hydrochloride (98%, [13515-93-0], Aldrich) was added and the reaction mixture was heated to 50° C. Upon cooling reaction is quenched with water and pH is adjusted to 3 with 2N HCl followed by splitting off the bottom layer and the additional wash with brine. Then the organic layer was treated with LiOH (aqueous; 1N), followed by adjusting pH to 3 with 2N HCl. The organic layer was separated, dried over magnesium sulfate, filtered and concentrated to yield a glassy solid, which is re-dissolved in ethanol followed by formation of its disodium salt with the appropriate sodium hydroxide. The final product disodium(2R)2{[(carboxylatomethyl)-(methyl)carbamoyl]amino}-3-{[(2E)-3,7,11,15-tetramethylhexadec-2-en-1-yl]sulfanyl}propanoate is separated by filtration, dried in the vacuum oven at 25° C. and packaged under nitrogen in glass jars in a 61% yield.

This synthesis scheme is summarized below:

powder, [497-19-8], Aldrich) is added through a star valve to form the sodium salt of L-cysteine plus carbon dioxide. The mixture is then vigorously stirred and phytyl bromide is added slowly. The mixture is sampled for reaction completion and then isopropanol is removed under reduced pressure. Water is added to quench the reaction and dissolve the solids and then pH is adjusted to 7 with 2N HCL. The

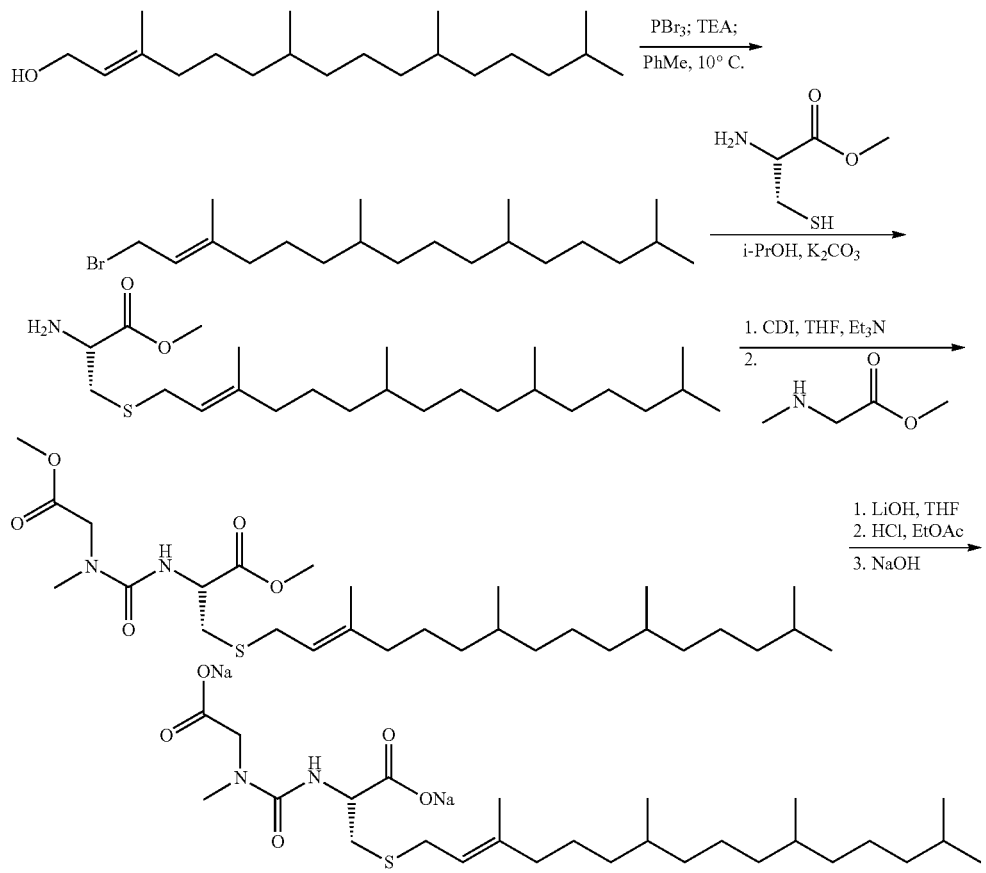

Example 2

Synthesis of disodium (2R)-2-{[(carboxylatomethyl)(ethyl)carbamoyl]amino}-3-{[(2E)-3,7,11,15-tetramethylhexadec-2-en-1-yl]sulfanyl}propanoate A solution of toluene (99.5+%, CAS [108-88-3], Aldrich) and phosphorous tribromide (99+%, CAS [7789-60-8], Aldrich) is added to a mixture of a commercially phytol (97%, CAS [7541-49-3], toluene, and triethylamine (99.5+%, CAS [121-44-8], Aldrich) at a controlled rate keeping the temperature in the pot below 10° C. The mixture is warmed to 20-25° C. and sampled for reaction completion. The reaction is quenched with agitation by the addition of water, keeping the temperature below 25° C. The mixture is stirred to dissolve all phosphorous acid amine salts and then allowed to settle. The lower aqueous layer is split off and the organic layer washed with 15% brine, settled, and split. The organic layer is recovered and then vacuum stripped to remove the toluene from the desired phytyl bromide. Commercial L-cysteine methyl ester (98%, [18598-63-5], Aldrich) and isopropanol (99.5%, [67-63-0], Aldrich) are charged to a kettle at 24° C. Sodium carbonate (99.5%, mixture is stirred for 30 min to ensure complete hydrolysis of any traces of phytyl bromide (monitored by HPLC), settled, and the amorphous solid is separated by filtration. The solid is dissolved in the THF (>99.9%, [109-99-9] Aldrich) and CDI (>97%, [530-62-1], Aldrich) are added, followed by addition of triethylamine (99.5+%, CAS [121-44-8], Aldrich). Finally, N-Ethyl Glycine methyl ester hydrochloride (97%, [1121527-61-4], Enamine) was added and the reaction mixture was heated to 50° C. Upon cooling reaction is quenched with water and pH is adjusted to 3 with 2N HC followed by splitting off the bottom layer and the additional wash with brine. Than the organic layer was treated with LiOH (aqueous; 1N), followed by adjusting pH to 3 with 2N HCL. The organic layer was separated, dried over magnesium sulfate, filtered and concentrated to yield a glassy solid, which is re-dissolved in ethanol followed by formation of its disodium salt with the appropriate sodium hydroxide. The final product disodium (2R)-2-{[(carboxylatomethyl)(ethyl)carbamoyl]amino}-3-{[(2E)-3,7,11,15-tetramethylhexadec-2-en-1 yl]sulfanyl}-propanoate is separated by filtration, dried in the vacuum oven at 25° C. and packaged under nitrogen in glass jars in 48% yield.

This synthesis scheme is summarized below:

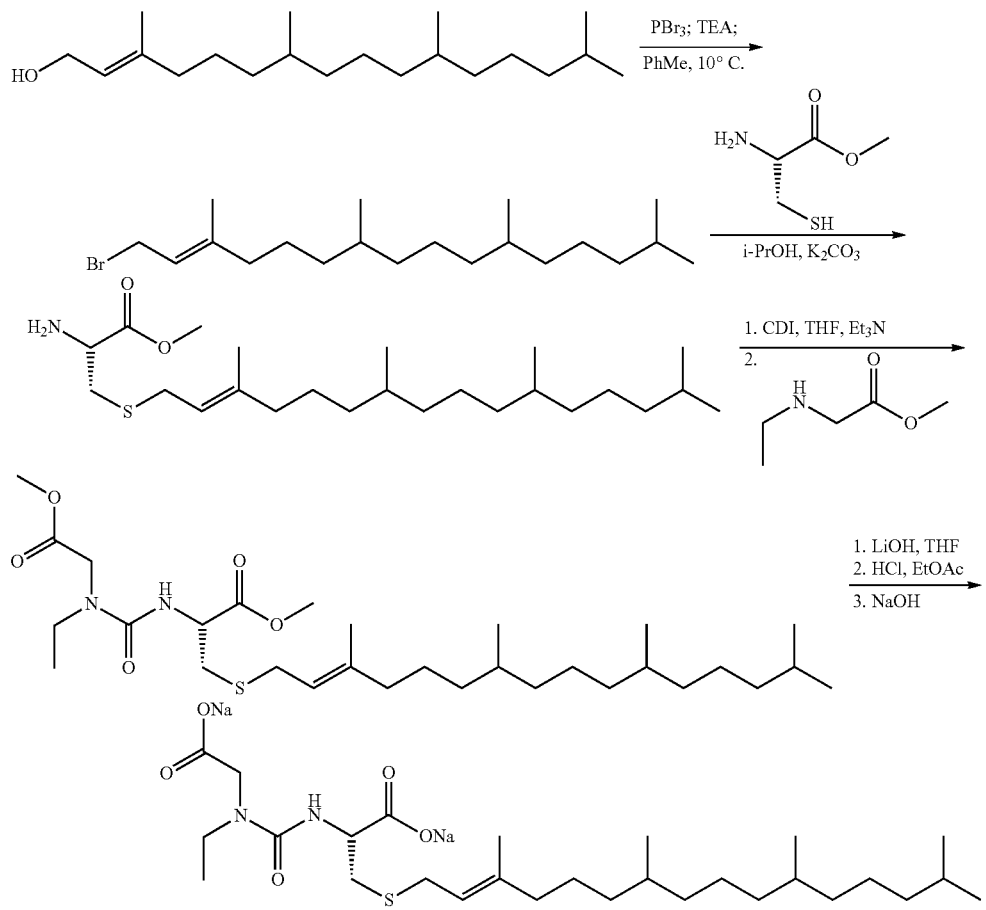

Example 3

Synthesis of (disodium (2S)-1-{[(1R)-1-carboxylato-2-{[(2E)-3,7,11,15-tetramethylhexadec-2-en-1-yl]sulfanyl}ethyl]carbamoyl}pyrrolidine-2-carboxylate)

A solution of toluene (99.5+%, CAS [108-88-3], Aldrich) and phosphorous tribromide (99+%, CAS [7789-60-8], Aldrich) is added to a mixture of a commercially phytol (97%, CAS [7541-49-3], toluene, and triethylamine (99.5+%, CAS [121-44-8], Aldrich) at a controlled rate keeping the temperature in the pot below 10° C. The mixture is warmed to 20-25° C. and sampled for reaction completion. The reaction is quenched with agitation by the addition of water, keeping the temperature <25° C. The mixture is stirred to dissolve all phosphorous acid amine salts and then allowed to settle. The lower aqueous layer is split off and the organic layer washed with 15% brine, settled, and split. The organic layer is recovered and then vacuum stripped to remove the toluene from the desired phytyl bromide. Commercial L-cysteine methyl ester (98%, [18598-63-5], Aldrich) and isopropanol (99.5%, [67-63-0], Aldrich) are charged to a kettle at 24° C. Sodium carbonate (99.5%, powder, [497-19-8], Aldrich) is added through a star valve to form the sodium salt of L-cysteine plus carbon dioxide. The mixture is then vigorously stirred and phytyl bromide is added slowly. The mixture is sampled for reaction completion and then isopropanol is removed under reduced pressure. Water is added to quench the reaction and dissolve the solids and then pH is adjusted to 7 with 2N HCl. The mixture is stirred for 30 min to ensure complete hydrolysis of any traces of phytyl bromide (monitored by HPLC), settled, and the amorphous solid is separated by filtration. The solid is dissolved in the THF (>99.9%, [109-99-9] Aldrich) and CDI (>97%, [530-62-1], Aldrich) are added, followed by addition of trimethylamine (99.5+%, CAS [121-44-8], Aldrich). Finally, proline methyl ester hydrochloride (98%, [2133-40-6], Aldrich) was added and the reaction mixture was heated to 50° C. Upon cooling reaction is quenched with water and pH is adjusted to 3 with 2N HCl followed by splitting off the bottom layer and the additional wash with brine. Than the organic layer was treated with LiOH (aqueous; 1N), followed by adjusting pH to 3 with 2N HCl. The organic layer was separated, dried over magnesium sulfate, filtered and concentrated to yield a glassy solid which is re-dissolved in ethanol followed by formation of its disodium salt with the appropriate sodium hydroxide. The final product (disodium (2S)-1-{[(1R)-1-carboxylato-2-{[(2E)-3,7,11,15-tetramethylhexadec-2-en-1-yl]sulfanyl}ethyl]carbamoyl}pyrrolidine-2-carboxylate) is separated by filtration, dried in the vacuum oven at 25° C. and packaged under nitrogen in glass jars in 67% yield.

This reaction scheme is summarized below:

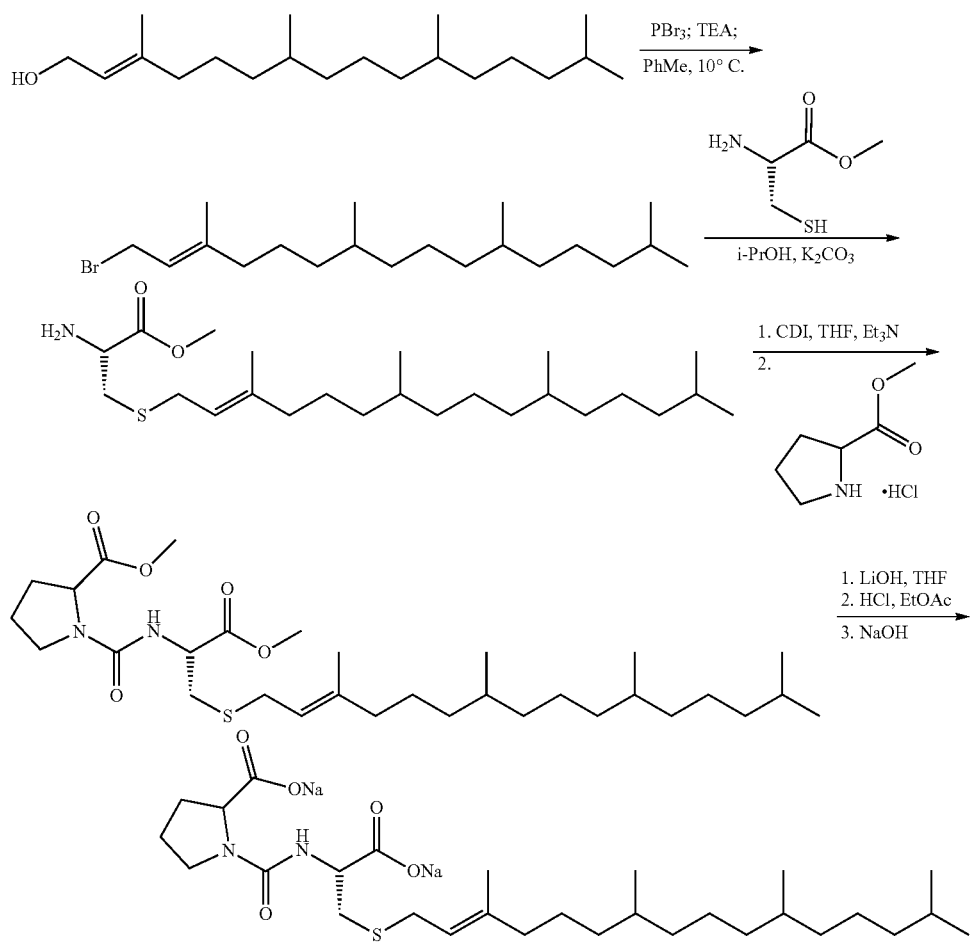

Example 4

Synthesis of (trisodium (2R)-2-{[bis(carboxylatomethyl)carbamoyl]amino}-3-{[(2E)-3,7,11,15-tetramethylhexadec-2-en-1-yl]sulfanyl}propanoate A solution of toluene (99.5+%, CAS [108-88-3], Aldrich) and phosphorous tribromide (99+%, CAS [7789-60-8], Aldrich) is added to a mixture of a commercially phytol (97%, CAS [7541-49-3], toluene, and triethylamine (99.5+%, CAS [121-44-8], Aldrich) at a controlled rate keeping the temperature in the pot below 10° C. The mixture is warmed to 20-25° C. and sampled for reaction completion. The reaction is quenched with agitation by the addition of water, keeping the temperature below 25° C. The mixture is stirred to dissolve all phosphorous acid amine salts and then allowed to settle. The lower aqueous layer is split off and the organic layer washed with 15% brine, settled, and split. The organic layer is recovered and then vacuum stripped to remove the toluene from the desired phytyl bromide. Commercial L-cysteine methyl ester (98%, [18598-63-5], Aldrich) and isopropanol (99.5%, [67-63-0], Aldrich) are charged to a kettle at 24° C. Sodium carbonate (99.5%, powder, [497-19-8], Aldrich) is added through a star valve to form the sodium salt of L-cysteine plus carbon dioxide. The mixture is then vigorously stirred and phytyl bromide is added slowly. The mixture is sampled for reaction completion and then isopropanol is removed under reduced pressure. Water is added to quench the reaction and dissolve the solids and then pH is adjusted to 7 with 2N HCl. The mixture is stirred for 30 min to ensure complete hydrolysis of any traces of phytyl bromide (monitored by HPLC), settled, and the amorphous solid is separated by filtration. The solid is dissolved in the THF (>99.9%, [109-99-9] Aldrich) and CDI (>97%, [530-62-1], Aldrich) are added, followed by addition of triethylamine (99.5+%, CAS [121-44-8], Aldrich). Finally, dimethyl 2,2'-iminodiacetate (98%, [6096-81-7], MolBase) was added and the reaction mixture was heated to 50° C. Upon cooling reaction is quenched with water and pH is adjusted to 3 with 2N HCl followed by splitting off the bottom layer and the additional wash with brine. Than the organic layer was treated with LiOH (aqueous; 1N), followed by adjusting pH to 3 with 2N HCl. The organic layer was separated, dried over magnesium sulfate, filtered and concentrated to yield a glassy solid which is re-dissolved in ethanol followed by formation of its disodium salt with the appropriate sodium hydroxide. The final product (trisodium (2R)-2-{[bis(carboxylatomethyl)carbamoyl]amino}-3-{[(2-E)-3,7,11,15-tetramethylhexadec-2-en-1-yl]sulfanyl} propanoate is separated by filtration, dried in the vacuum oven at 25° C. and packaged under nitrogen in glass jars in 70% yield.

This synthesis scheme is summarized below:
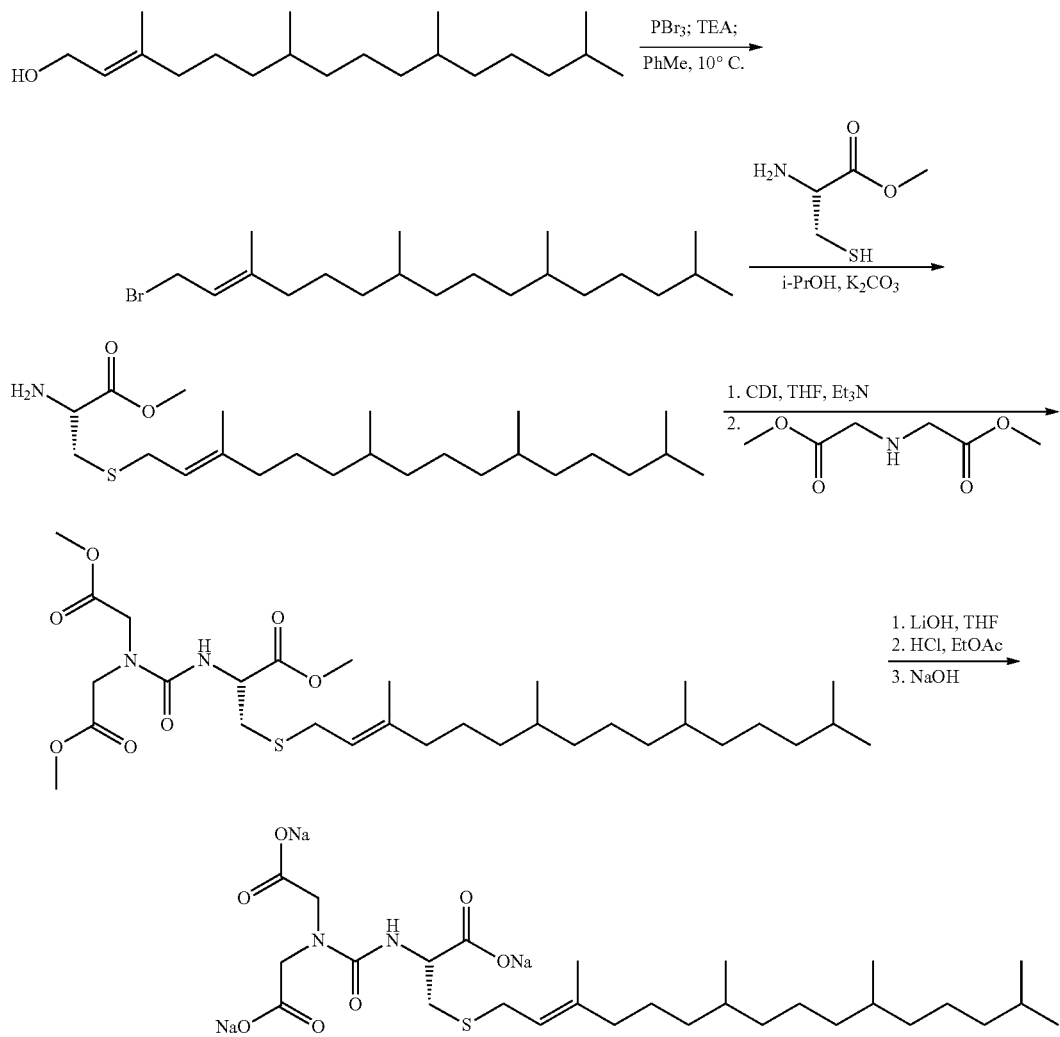
Example 5
Synthesis of Disodium N-(2-(carboxylatomethoxy)acetyl)-S-((E)-3,7,11,15-tetramethylhexadec-2-en-1-yl)-L-cysteinate
The titled compound was prepared by the synthesis scheme set forth below:
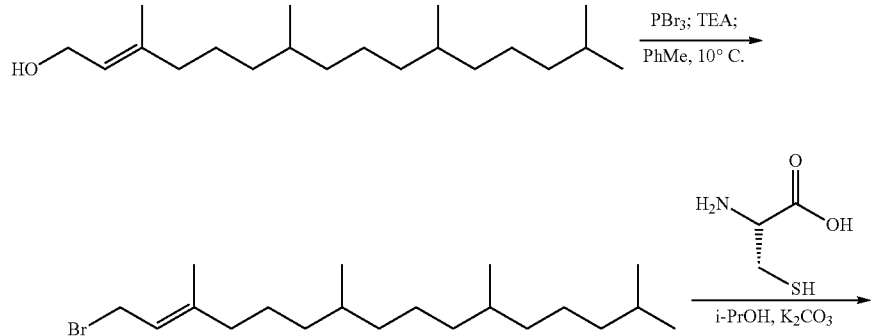

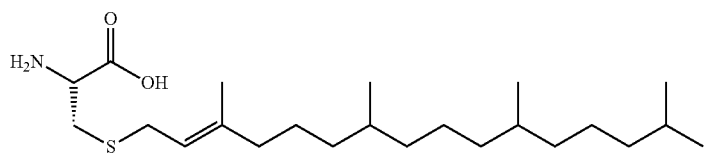
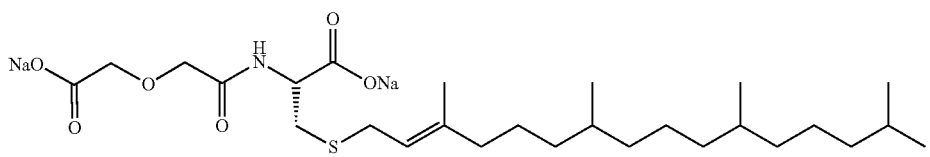

Example 6

Synthesis of (2S)-1-{[(1R)-1-carboxy-2-{[(2E)-3,7,11,15-tetramethylhexadec-2-en-1-yl]sulfanyl}ethyl]carbamoyl}piperidine-2-carboxylic acid The following general experimental procedures were used for Examples 6-35 as described below. Proton Nuclear Magnetic Resonance ($^1$HNMR) spectroscopy was recorded on a Bruker 500 MHz spectrometer, dimethyl sulfoxide (DMSO-d6), methanol ($CD_3OD$) or chloroform ($CDCl_3$) was used as the $^1$H-NMR solvent. The residual proton absorption of the deuterated solvent was used as the internal standard. All $^1$H-NMR chemical shift are reported as δ values in the parts per million (ppm). The splitting pattern abbreviations are as follows: s, singlet; d, doublet; t, triplet; q, quartet; br, broad; m, multiplet; dd, doublet of doublet; dt, doublet of triplets. The HPLC analysis was done using a phenomenex luna $C_{18}$(2)50×4.6 mm column. The mobile phase is 60% water, 40% acetonitrile containing 0.05% trifluoroacetic acid at 2 ml per minute flow rate for the first 2.5 minutes, followed by a gradient to 100% acetonitrile containing 0.05% TFA over 10 minutes. The eluent was observed at 214 nm.

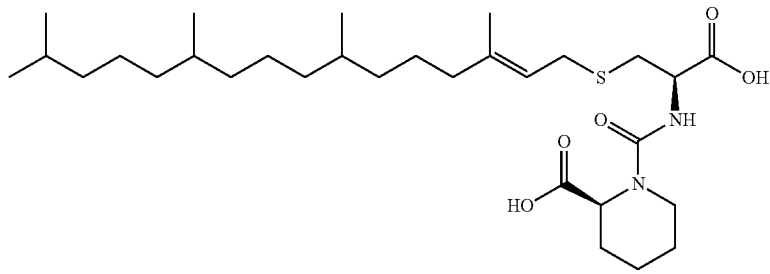 [SMILES: C/C(=C\CSC[C@H](NC(=O)N1CCCC[C@H]1C(=O)O)C(=O)O)CCCC(C)CCCC(C)CCCC(C)C]

The titled compound, shown above, was prepared according to the general procedure described in Examples 1-5. The prepared compound was characterized as follows: 1H-NMR (500 MHz, CDCl3) δ 0.78 (m, 12H), 1.21-1.64 (m, 26H), 1.72 (s, 3H), 1.76 (m, 1H), 2.02 (br s, 3H), 2.48 (br s, 1H), 2.27 (t, 1H), 3.42 (m, 4H), 3.81 (dd, 1H), 4.27 (dd, 1H), 4.82 (t, 1H), 5.20 (t, 1H); 13C-NMR (125 MHz, CDCl3) δ 16.1, 19.1, 21.9, 23.7, 25.4, 25.6, 25.7, 26.2, 26.7, 34.4, 37.8, 38.0, 38.2, 38.9, 39.3, 40.2, 40.6, 47.7, 53.0, 116.3, 137.4, 140.3, 150.2, 167.2, 168.7.

Example 7

Synthesis of trisodium (2R)-2-{[bis(carboxylatomethyl)carbamoyl]amino}-3-(methylsulfanyl)propanoate

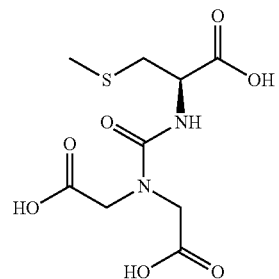 [SMILES: CSC[C@H](NC(=O)N(CC(=O)O)CC(=O)O)C(=O)O]

S-Methyl cysteine methyl ester (500 mg, 2.69 mmol) was suspended in THF (10 mL) followed by addition of Hunigs base (470 uL, 2.69 mmol), followed by CDI (611 mg, 3.23 mmol). The reaction was stirred for 2 hrs at room temperature and was monitored by TLC. Once the starting material was consumed, diethylaminoacetate (414 uL, 2.69 mmol) was added and reaction was further stirred overnight. The reaction mixture was concentrated partitioned between EtOAc (20 mL) and water (20 mL). The organic layer was dried over sodium sulfate, passed through a silica gel plug and concentrated. The resulting trimester derivative was dissolved in THF (10 mL) and 1N NaOH (3 mL) was added. The reaction mixture was stirred at room temperature for 6 hrs, then acidified with 1N HCl (4 mL) and extracted with EtOAc (3×10 mL). The organic layer was dried over magnesium sulfate and concentrated to yield the titled compound (235 mg, 29%).

This compound was characterized as follows. (535 mg, 82% yield): $^1$H-NMR (500 MHz, D$_2$O) δ 2.11 (s, 3H), 2.72 (dd, 1H), 2.81 (dd, 1H), 3.70 (m, 2H), 3.82 (d, 2H), 4.26 (dd, 1H); $^{13}$C-NMR (125 MHz, D$_2$O) δ 25.7, 36.6, 52.2, 55.1, 158.3, 178.2, 182.5.

Example 8

Synthesis of 2-{[(adamantan-1-yl)carbamoyl](carboxymethyl)amino}acetic acid

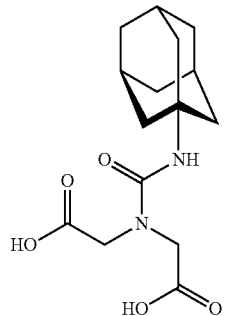

To a solution of adamantylisocyanate (500 mg, 2.82 mmol) in DCM diethyliminoacetate (433 uL, 2.82 mmol) was added and the reaction mixture was stirred for 2 hrs at room temperature. The reaction was monitored by TLC. The reaction mixture was concentrated and re-dissolved in THD (10 mL). 1N NaOH (6 ml) was added and the mixture was stirred for 4 hrs at room temperature. The hydrolysis was monitored by HPLC. The product was isolated by adding 1N HCl (8 mL) followed by extraction with EtOAc. The organic layer was dried over sodium sulfate and concentrated to yield the titled compound (743 mg, 85%) as a white solid.

This compound was characterized as follows. $^1$H-NMR (500 MHz, CDCl$_3$) δ 1.62 (m, 6H), 2.03 (m, 9H), 4.02 (s, 4H), 4.98 (s, 111); $^{13}$C-NMR (125 MHz, CDCl$_3$) δ 29.2, 38.7, 41.9, 51.6, 158.1, 171.2;

Example 9

Synthesis of 1-{[(1R)-1-carboxy-2-{[(2E)-3,7,11,15-tetramethylhexadec-2-en-1-yl]sulfanyl}ethyl]carbamoyl}azetidine-2-carboxylic

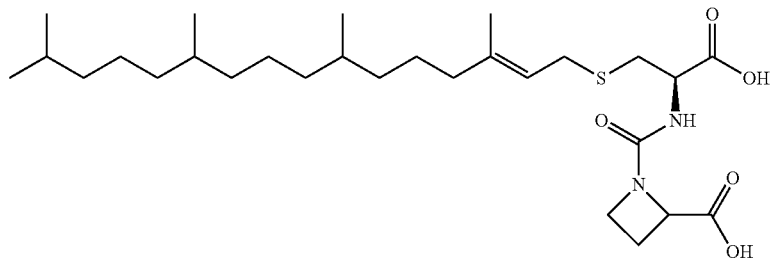 [SMILES: C/C(=C\CSC[C@H](NC(=O)N1CCC1C(=O)O)C(=O)O)CCCC(C)CCCC(C)CCCC(C)C]

The titled compound, shown above, was prepared according to the general procedure described in Examples 1-5. The prepared compound was characterized as follows: $^1$H-NMR (500 MHz, CDCl$_3$) δ 0.79 (m, 12H), 1.19-1.61 (m, 24H), 1.66 (m, 1H), 1.71 (s, 31H), 1.98 (hr s, 3H), 2.84 (m, 2H), 3.27 (m, 2H), 3.47 (m, 1H), 4.24 (m, 2H), 4.59 (m, 1H), 5.22 (m, 1H); $^{13}$C-NMR (125 MHz, CDCl$_3$) δ 17.3, 20.1, 20.8, 23.7, 26.1, 26.3, 26.6, 29.8, 34.2, 38.7, 39.1, 39.4, 39.9, 53.2, 54.4 117.5, 142.2, 158.8, 167.1, 168.7.

Example 10

Synthesis of 6-{[(2E)-3,7,11,15-tetramethylhexadec-2-en-1-yl]sulfanyl}pyridine-3-carboxylic acid

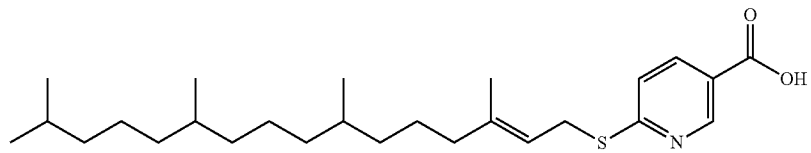 [SMILES: C/C(=C\CSc1ccc(C(=O)O)cn1)CCCC(C)CCCC(C)CCCC(C)C]

To a solution of phytyl cysteine methyl ester (464 mg; 1.03 mmol) and 2-chloro-5-methylcarboxylate-pyridine (181 mg; 1.03 mmol) in isopropanol (5 mL) Cs₂CO₃ (738 mg; 2.27 mmol) was added. The reaction mixture was heated for 4 hrs to a gentle reflux and monitored by HPLC. Once the starting material was fully consumed, the reaction mixture was concentrated and THF (2 ml) was added followed by 1N NaOH (2 mL). The resulting mixture was stirred overnight at room temperature. After 16 hrs HPLC indicated that diester intermediate was fully hydrolyzed and reaction mixture was acidified with 1N HCl to pH 3 and extracted with EtOAc (2×10 mL). The organic layer was concentrated and the product (28 mg; 7% yield) was isolated by column chromatography.

The titled compound was characterized as follows: ¹H-NMR (500 MHz, CDCl₃) δ 0.88 (m, 12H), 1.21-1.65 (m, 18H), 1.66 (m, 1H), 1.71 (s, 3H), 1.98 (br s, 3H), 2.21 (m, 2H), 3.77 (m, 1H), 5.27 (m, 1H); ¹³C-NMR (125 MHz, CDCl₃) δ 17.9, 18.6, 20.3, 20.4, 20.6, 20.8, 29.0, 30.5, 39.4, 109.2, 114.1, 124.7, 137.9, 139.2, 150.1, 162.2, 172.0.

Example 11

Synthesis of 2-{[(1R)-1-carboxy-2-{[(2E)-3,7,11,15-tetramethylhexadec-2-en-1-yl]sulfanyl}ethyl]amino}-4-(trifluoromethyl)pyrimidine-5-carboxylic acid disodium

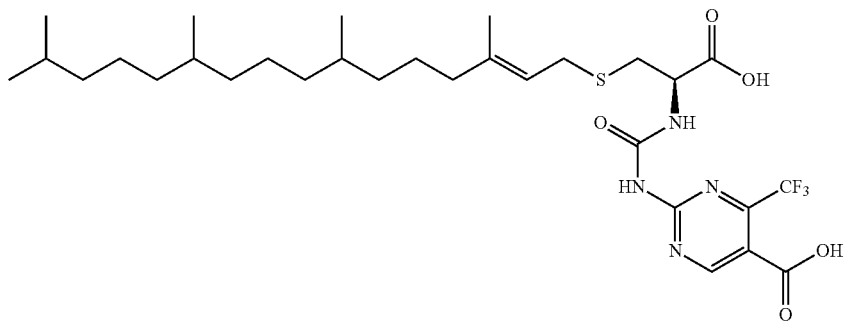 [SMILES: C/C(=C\CSC[C@H](NC(=O)Nc1ncc(C(=O)O)c(C(F)(F)F)n1)C(=O)O)CCCC(C)CCCC(C)CCCC(C)C]

To a solution of phytyl cysteine methyl ester (464 mg; 1.03 mmol) and 2-chloro-4-trifluoromethyl-5-methylcarboxylate-pyrimidine (262 mg; 1.03 nmol) in isopropanol (5 nL) Cs₂CO₃ (738 mg; 2.27 mmol) was added. The reaction mixture was heated for 4 hrs to a gentle reflux and monitored by HPLC. Once the starting material was fully consumed, the reaction mixture was concentrated and THF (2 mL) was added followed by 1N NaOH (2 mL). The resulting mixture was stirred overnight at room temperature. After 16 hrs HPLC indicated that diester intermediate was fully hydrolyzed and reaction mixture was acidified with 1N HCl to pH 3 and extracted with EtOAc (2×10 mL). The organic layer was concentrated and the product (211 mg; 34% yield) was isolated by column chromatography. The titled compound was characterized as follows: ¹H-NMR (500 MHz, CDCl₃) δ 0.87 (m, 12H), 1.21-1.63 (m, 22H), 1.68 (m, 1H), 1.77 (s, 3H), 2.03 (br s, 2H), 3.07-3.22 (m, 31), 4.58 (m, 1H), 5.29 (m, 1H); ¹³C-NMR (125 MHz, CDCl₃) δ 14.9, 18.8, 20.2, 20.5, 20.6, 20.7, 28.8, 30.7, 39.2, 39.5, 52.1, 110.5, 119.9, 126.6, 126.9, 129.6, 131.6, 139.1, 139.6, 161.9, 172.1.

Example 12

Synthesis of disodium (2R)-2-[2-(carboxylatomethoxy)acetamido]-3-{[(2E)-3,7,11,15-tetramethylhexadec-2-en-1-yl]sulfanyl}propanoate

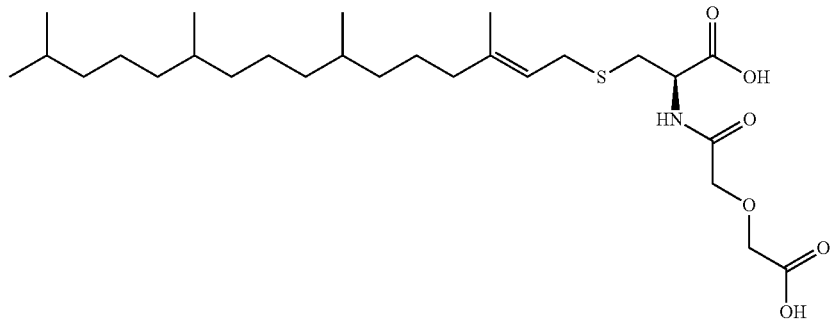 [SMILES: C/C(=C\CSC[C@H](NC(=O)COCC(=O)O)C(=O)O)CCCC(C)CCCC(C)CCCC(C)C]

Diglycolic anhydride (154 mg, 1.33 mmol) was added to a stirring solution of phytyl cysteine methyl ester (500 mg, 1.21 mmol) in THF (10 mL) at room temperature. The reaction mixture was heated at 50° C. for 30 minutes, at which time the reaction was complete by HPLC. The crude reaction mixture was then cooled to room temperature, and a 1M solution of lithium hydroxide (5 mL) was added at room temperature. Enough methanol was added to the bi-phasic mixture so that it became a homogenous solution and was stirred at 50° C. for 1 hour. The reaction was monitored by HPLC for completion. Upon completion, the reaction was cooled to room temperature, diluted in ethyl acetate, washed once with a 1N HCl solution, once with brine and dried over magnesium sulfate. The ethyl acetate was filtered, and concentrated to dryness on a rotary evaporator to give 354 mg of the product as a brown oil in 56% yield. The titled compound was characterized as follows: $^1$H NMR (500 MHz, Chloroform-d) δ 8.39 (s, 2H), 7.89 (d, J=8.4 Hz, 1H), 5.35-5.16 (m, 1H), 4.89 (ddd, J=8.5, 6.7, 4.9 Hz, 1H), 4.43-4.26 (m, 2H), 4.22-4.09 (m, 2H), 3.48-3.15 (m, 2H), 3.07-2.86 (m, 2H), 2.05-1.94 (m, 2H), 1.69 (s, 3H), 1.54 (dp, J=13.2, 6.6 Hz, 1H), 1.44-1.02 (m, 19H), 0.92-0.83 (m, 12H).

Example 13

Synthesis of (2R)-2-{[(carboxymethyl)(methyl)carbamoyl]amino}-3-{[(2E)-3,7,11,15-tetramethylhexadec-2-en-1-yl]sulfanyl}propanoic acid

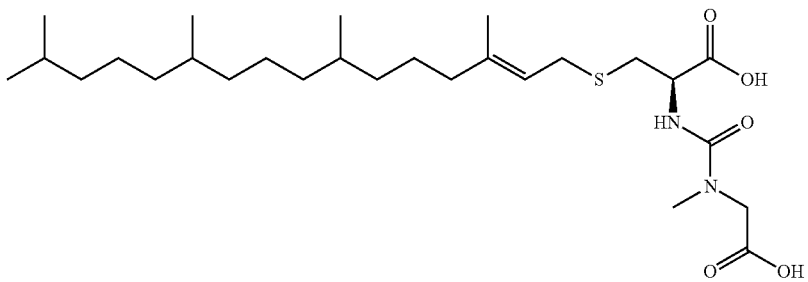 [SMILES: C/C(=C\CSC[C@H](NC(=O)N(C)CC(=O)O)C(=O)O)CCCC(C)CCCC(C)CCCC(C)C]

Carbonyl diimidazole (107 mg, 1.2 mmol) was added to a solution of phytyl cysteine methyl ester (500 mg, 1.21 mmol) in THF (10 mL) at room temperature and stirred until consumption of starting material was observed by HPLC. After conversion to the imidazole urea was complete, sarcosine hydrochloride (201 mg, 1.44 mmol) was added to the reaction mixture, followed by N,N-diisopropylethylamine (0.418 mL, 2.4 mmol) at room temperature. The reaction mixture was heated at 50° C. and monitored by HPLC for consumption of the imidazole urea. After disappearance of the imidazole urea was observed, 0.552 mL of a 1M lithium hydroxide solution was added to the reaction mixture and stirred at room temperature. When hydrolysis of the bis-ester was complete by HPLC, the reaction mixture was partitioned between ethyl acetate and a 10% citric acid solution. The organic layer was washed with brine and dried over magnesium sulfate. The ethyl acetate was filtered and concentrated to dryness. The crude product was purified by flash chromatography using ethyl acetate/hexanes as the eluent to give 74 mg of the product as a white waxy solid in 78% yield. $^1$H NMR (500 MHz, Methanol-d4) δ 5.29-5.20 (m, 1H), 4.49 (dd, J=8.1, 4.9 Hz, 1H), 4.15-4.02 (m, 2H), 3.33-3.24 (m, 2H), 3.21-3.14 (m, 1H), 3.04 (s, 3H), 3.03-2.99 (m, 1H), 2.86 (dd, J=14.0, 8.1, 1.0 Hz, 1H), 2.05-2.00 (m, 2H), 1.70 (d, J=1.4 Hz, 3H), 1.60-1.54 (m, 1H), 1.52-1.04 (m, 19H), 0.95-0.82 (m, 12H). This compound corresponds to Compound C.

Example 14

Synthesis of (2S)-1-{[(1R)-1-carboxy-2-{[(2E)-3,7,11,15-tetramethylhexadec-2-en-1-yl]sulfanyl}ethyl]carbamoyl}pyrrolidine-2-carboxylic acid

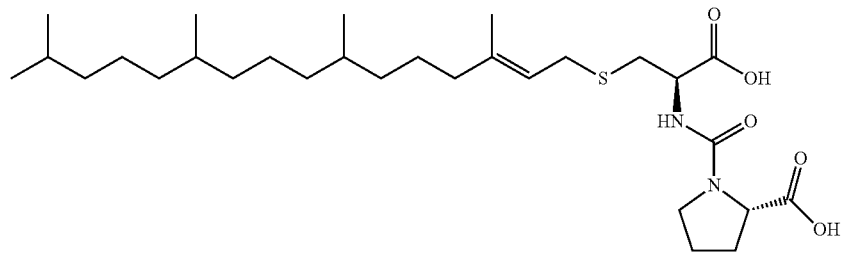 [SMILES: C/C(=C\CSC[C@H](NC(=O)N1CCC[C@H]1C(=O)O)C(=O)O)CCCC(C)CCCC(C)CCCC(C)C]

The title compound was prepared according to the procedure for Example 13 to give 216 mg of an off-white solid in 33% yield. The titled compound was characterized as follows: $^1$H NMR (501 MHz, Chloroform-d) δ 8.82 (s, 2H), 5.61-5.44 (m, 1H), 5.21 (t, 1H), 4.67-4.43 (m, 2H), 3.60-3.33 (m, 2H), 3.28-3.13 (m, 2H), 3.07-2.90 (m, 2H), 2.43-1.92 (m, 6H), 1.66 (s, 3H), 1.54 (dp, J=13.3, 6.7 Hz, 1H), 1.47-1.01 (m, 19H), 0.95-0.78 (m, 12H).

Example 15

Synthesis of (2R)-2-{[(carboxymethyl)(ethyl)carbamoyl]amino}-3-{[(2E)-3,7,11,15-tetramethylhexadec-2-en-1-yl]sulfanyl}propanoic acid

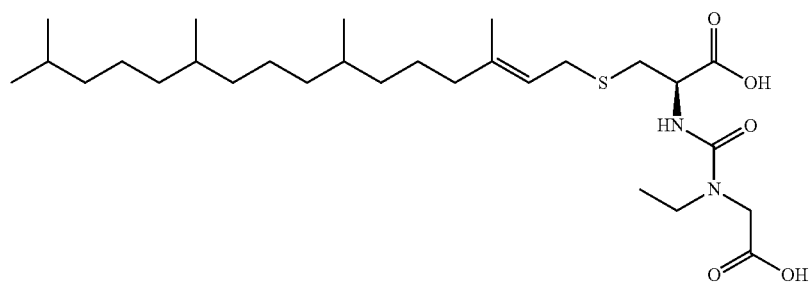 [SMILES: CCN(CC(=O)O)C(=O)N[C@@H](CSC/C=C(\C)CCCC(C)CCCC(C)CCCC(C)C)C(=O)O]

The title compound was prepared according to the procedure for Example 13 to give 335 mg of a light yellow oil in 49% yield. $^1$H NMR (501 MHz, Chloroform-d) δ 7.85 (s, 2H), 5.72 (d, J=7.0 Hz, 1H), 5.20 (t, J=7.7 Hz, 1H), 4.59 (d, J=6.0 Hz, 1H), 4.18-3.91 (m, 2H), 3.37 (d, J=7.5 Hz, 2H), 3.20 (qd, J=13.0, 7.8 Hz, 2H), 2.98 (qd, J=13.8, 5.6 Hz, 3H), 2.04-1.91 (m, 2H), 1.65 (s, 3H), 1.53 (hept, J=6.6 Hz, 1H), 1.46-1.00 (m, 19H), 0.91-0.81 (m, 12H).

Example 16

Synthesis of (2R)-2-{[bis(carboxymethyl)carbamoyl]amino}-3-{[(2E)-3,7,11,15-tetramethylhexadec-2-en-1-yl]sulfanyl}propanoic acid

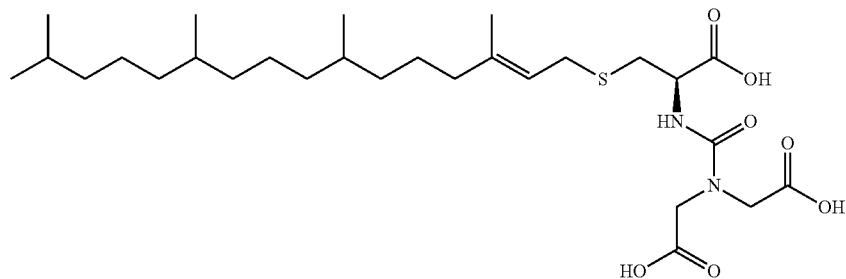 [SMILES: C/C(=C\CSC[C@H](NC(=O)N(CC(=O)O)CC(=O)O)C(=O)O)CCCC(C)CCCC(C)CCCC(C)C]

The title compound was prepared according to the procedure for Example 13 to give 407 mg of a foamy yellow solid in 60% yield. $^1$H NMR (500 MHz, Methanol-d4) δ 5.27-5.19 (m, 1H), 4.47 (dd, J=7.8, 5.0 Hz, 1H), 4.21-4.10 (m, 4H), 3.28 (dd, J=13.3, 8.2 Hz, 1H), 3.16 (dd, J=13.2, 7.3 Hz, 1H), 2.98 (dd, J=13.9, 5.0 Hz, 1H), 2.83 (ddd, J=13.9, 7.8, 1.2 Hz, 1H), 2.04 (td, J=7.2, 3.0 Hz, 2H), 1.70 (s, 3H), 1.55 (dq, J=13.3, 6.7 Hz, 1H), 1.51-1.06 (m, 19H), 0.93-0.81 (m, 12H).

Example 17

Synthesis of disodium 1-{[(1R)-1-carboxylato-2-{[(2E)-3,7,11,15-tetramethylhexa-dec-2-en-1-yl]sulfanyl}ethyl]carbamoyl}piperidine-4-carboxylate

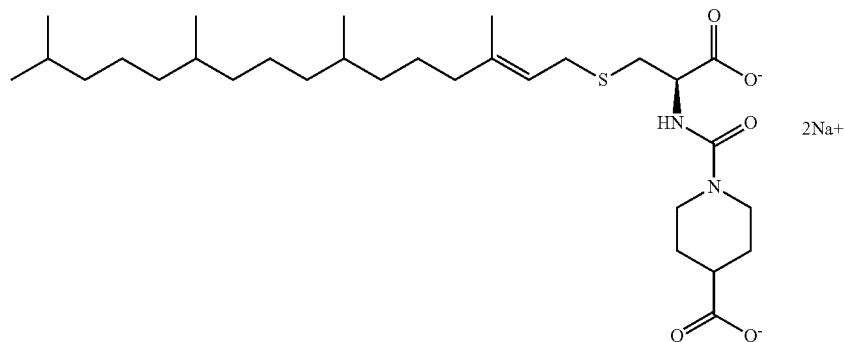 [SMILES: C/C(=C\CSC[C@H](NC(=O)N1CCC(C(=O)[O-])CC1)C(=O)[O-])CCCC(C)CCCC(C)CCCC(C)C]

The title compound was prepared according to the procedure for Example 13 to give 175 mg of the carboxylic acid. The isolated carboxylic acid was dissolved in 2 mL of ethanol, followed by addition of 0.062 mL of 10N sodium hydroxide solution at room temperature, and stirred for 1 hour. The resulting suspension was triturated with 2 mL of acetonitrile, filtered and washed with acetonitrile to give 120 mg of a white solid in 17% yield. $^1$H NMR (501 MHz, Deuterium Oxide) δ 5.18-5.04 (m, 1H), 4.14 (dd, J=7.8, 4.9 Hz, 1H), 3.98 (d, J=12.3 Hz, 1H), 3.75 (d, J=12.6 Hz, 1H), 3.19-3.03 (m, 2H), 2.89-2.60 (m, 4H), 2.30-2.16 (m, 1H), 1.97-1.82 (m, 2H), 1.82-1.69 (m, 2H), 1.57 (s, 3H), 1.53-0.91 (m, 20H), 0.78 (d, J=6.1 Hz, 12H).

Example 18

Synthesis of disodium (2S,4R)-1-{[(1R)-1-carboxylato-2-{[(2E)-3,7,11,15-tetramethyl hexadec-2-en-1-yl]sulfanyl}ethyl]carbamoyl}-4-hydroxypyrrolidine-2-carboxylate

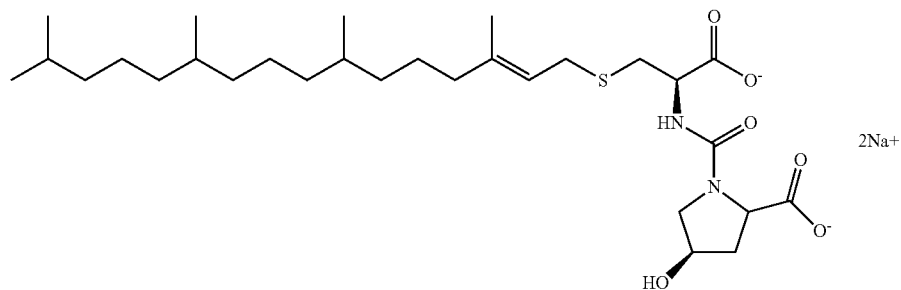 [SMILES: C/C(=C\CSC[C@H](NC(=O)N1C[C@H](O)CC1C(=O)[O-])C(=O)[O-])CCCC(C)CCCC(C)CCCC(C)C]

The title compound was prepared according to the procedure for Example 13 to give 200 mg of an off-white solid in 33% yield. ¹H NMR (500 MHz, Deuterium Oxide) δ 4.94-4.78 (m, 1H), 4.23-4.00 (m, 1H), 3.99-3.86 (m, 1H), 3.48-3.02 (m, 2H), 3.02-2.68 (m, 3H), 2.76-2.39 (m, 2H), 2.01-1.80 (m, 2H), 1.79-1.53 (m, 2H), 1.40-1.21 (m, 3H), 1.21-0.64 (m, 20H), 0.52 (d, J=6.5 Hz, 12H).

Example 19

Synthesis of (2R)-2-{[(E)-piperidine-1-carbonyl]amino}-3-{[(2E)-3,7,11,15-tetramethylhexadec-2-en-1-yl]sulfanyl}propanoic acid

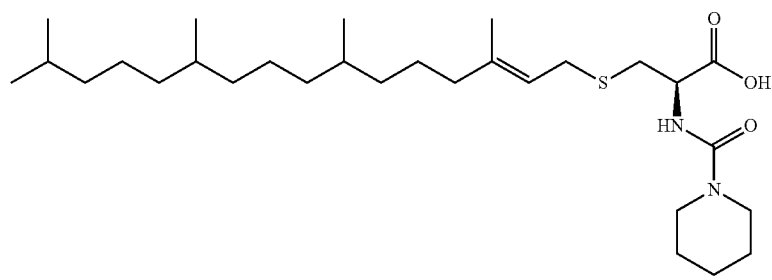 [SMILES: C/C(=C\CSC[C@H](NC(=O)N1CCCCC1)C(=O)O)CCCC(C)CCCC(C)CCCC(C)C]

The title compound was prepared according to the procedure for Example 13 to give 200 mg of a light brown oil in 18% yield. ¹H NMR (501 MHz, Methanol-d4) δ 6.73 (ddt, J=7.8, 6.5, 1.3 Hz, 1H), 5.90 (dd, J=6.8, 4.5 Hz, 1H), 4.90 (dtd, J=13.3, 8.0, 5.4 Hz, 4H), 4.71 (qd, J=13.0, 7.8 Hz, 2H), 4.50 (dd, J=13.6, 4.6 Hz, 1H), 4.38 (dd, J=13.6, 6.7 Hz, 1H), 3.55-3.48 (m, 2H), 3.17 (s, 3H), 3.15-2.99 (m, 5H), 2.98-2.52 (m, 21H), 2.44-2.31 (m, 12H).

Example 20

Synthesis of disodium 1-{[(1R)-1-carboxylato-2-{[(2E)-3,7,11,15-tetramethylhexadec-2-en-1-yl]sulfanyl}ethyl]carbamoyl}piperidine-3-carboxylate

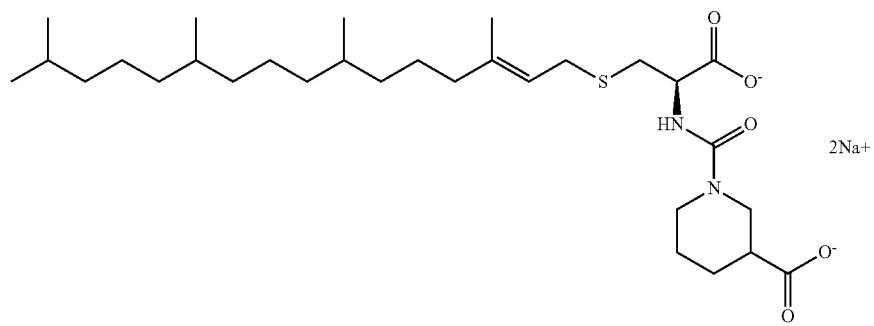 [SMILES: C/C(=C\CSC[C@H](NC(=O)N1CCCC(C(=O)[O-])C1)C(=O)[O-])CCCC(C)CCCC(C)CCCC(C)C]

The title compound was prepared according to the procedure for Example 13 to give 523 mg of an off-white solid in 39% yield. ¹H NMR (501 MHz, Deuterium Oxide) δ 5.19-5.06 (m, 1H), 4.17-4.03 (m, 1H), 3.93-3.76 (m, 2H), 3.65-3.30 (m, 2H), 3.21-2.65 (m, 4H), 2.29-2.10 (m, 2H), 1.99-1.83 (m, 4H), 1.57 (s, 3H), 1.47-1.39 (m, 1H), 1.39-0.92 (m, 19H), 0.90-0.65 (m, 12H).

Example 21

Synthesis of (2R)-2-[(pyrimidin-2-yl)amino]-3-{[(2E)-3,7,11,15-tetramethylhexadec-2-en-1-yl]sulfanyl}propanoic acid

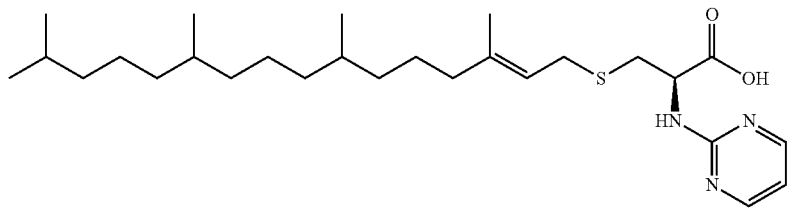 [SMILES: C/C(=C\CSC[C@H](Nc1ncccn1)C(=O)O)CCCC(C)CCCC(C)CCCC(C)C]

2-chloropyrimidine (127 mg, 1.11 mmol) was added at room temperature to a stirring solution of phytyl cysteine hydrochloride (500 mg, 1.11 mmol) in isopropanol (5 mL), followed by addition of 1 mL of a saturated sodium bicarbonate solution. The reaction was heated at 110° C. in a sealed tube for 3 days. Once the starting material was consumed by HPLC, the reaction mixture was cooled to room temperature, followed by addition of 3 mL of a 1N LiOH solution. The reaction mixture was stirred overnight, then diluted in ethyl acetate and washed once with a 10% citric acid solution, once with brine and then dried over magnesium sulfate. The ethyl acetate solution was filtered and concentrated on a rotary evaporator to give the crude product as a brown oil. The oil was purified by flash chromatography using ethyl acetate in hexanes as the eluent to give 173 mg of the product as a white solid in 32% yield. The titled compound was characterized as follows: $^1$H NMR (501 MHz, Methanol-d4) δ 8.29 (d, J=4.8 Hz, 2H), 6.66 (t, J=4.9 Hz, 1H), 5.20 (td, J=7.9, 1.7 Hz, 1H), 4.77-4.70 (m, 1H), 3.20 (tt, J=13.2, 6.4 Hz, 2H), 3.14-3.05 (m, 1H), 3.00 (dd, J=13.8, 6.4 Hz, 1H), 2.03-1.94 (m, 2H), 1.61 (s, 3H), 1.52 (dq, J=13.3, 6.6 Hz, 1H), 1.45-0.98 (m, 19H), 0.94-0.77 (m, 12H).

Example 22

Synthesis of 2-{[(1R)-1-carboxy-2-{[(2E)-3,7,11,15-tetramethylhexadec-2-en-1-yl]-sulfanyl}ethyl]amino}pyrimidine-4-carboxylic acid

Example 21

Synthesis of (2R)-2-[(pyrimidin-2-yl)amino]-3-{[(2E)-3,7,11,15-tetramethylhexadec-2-en-1-yl]sulfanyl}propanoic acid

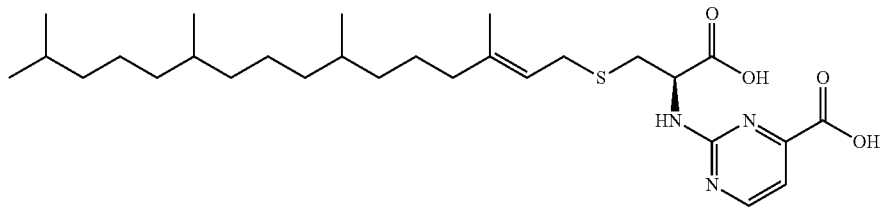 [SMILES: C/C(=C\CSC[C@H](Nc1nccc(C(=O)O)n1)C(=O)O)CCCC(C)CCCC(C)CCCC(C)C]

The title compound was prepared according to the procedure for Example 21 to give 486 mg of a white solid in 83% yield. $^1$H NMR (501 MHz, Methanol-d4) δ 8.49 (d, J=4.9 Hz, 1H), 7.27 (d, J=4.9 Hz, 1H), 5.18 (t, J=7.7 Hz, 1H), 4.86 (s, 1H), 3.25-3.13 (m, 2H), 3.12-3.04 (m, 1H), 3.02-2.93 (m, 1H), 2.04-1.85 (m, 2H), 1.58 (s, 3H), 1.49 (dt, J=13.3, 6.6 Hz, 1H), 1.42-0.95 (m, 19H), 0.87-0.77 (m, 12H).

Example 23

Synthesis of 2-{[(1R)-1-carboxy-2-{[(2E)-3,7,11,15-tetramethylhexadec-2-en-1-yl]sulfanyl}ethyl]amino}pyrimidine-5-carboxylic acid

Example 21

Synthesis of (2R)-2-[(pyrimidin-2-yl)amino]-3-{[(2E)-3,7,11,15-tetramethylhexadec-2-en-1-yl]sulfanyl}propanoic acid

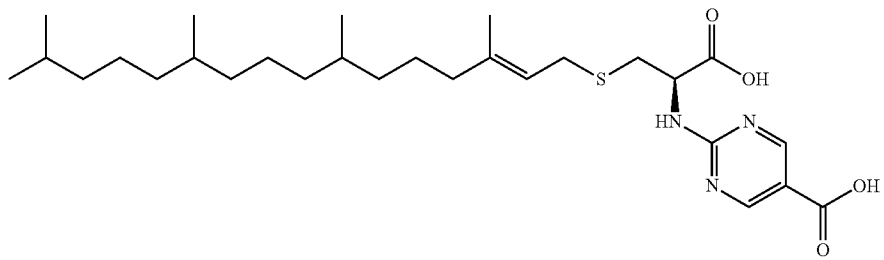 [SMILES: C/C(=C\CSC[C@H](Nc1ncc(C(=O)O)cn1)C(=O)O)CCCC(C)CCCC(C)CCCC(C)C]

The title compound was prepared according to the procedure for Example 21 to give 497 mg of a white solid in 85% yield. $^1$H NMR (501 MHz, Methanol-d4) δ 8.84 (d, J=7.5 Hz, 2H), 5.22 (t, J=7.5 Hz, 1H), 4.90-4.87 (m, 1H), 3.28 (dd, J=13.4, 8.0 Hz, 1H), 3.20 (dd, J=13.3, 7.4 Hz, 1H), 3.16-3.09 (m, 1H), 2.97 (dd, J=14.0, 7.8 Hz, 1H), 2.01 (t, J=7.4 Hz, 2H), 1.66 (d, J=1.3 Hz, 3H), 1.55 (dt, J=13.3, 6.7 Hz, 1H), 1.47-1.04 (m, 19H), 0.96-0.83 (m, 12H).

Example 24

Synthesis of (2R)-2-{[(carboxymethyl)(methyl)carbamoyl]amino}-3-{[(2Z)-3,7,11,15-tetramethylhexadec-2-en-1-yl]sulfanyl}propanoic acid

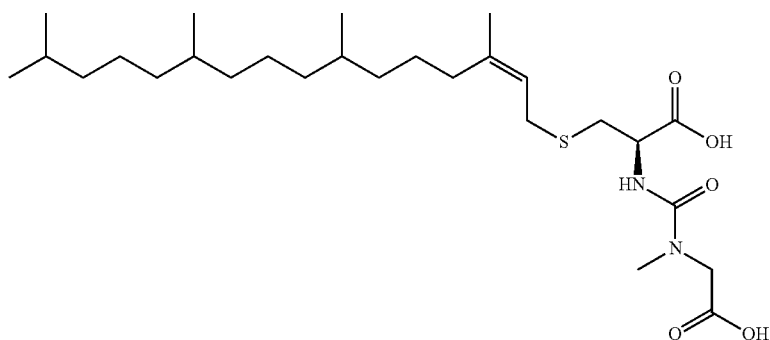 [SMILES: C/C(=C/CSC[C@H](NC(=O)N(C)CC(=O)O)C(=O)O)CCCC(C)CCCC(C)CCCC(C)C]

Disodium (2R)-2-{[(carboxylatomethyl) (methyl)carbamoyl]amino}-3-{[(2E)-3,7,11,15-tetramethylhexadec-2-en-1-yl]sulfanyl}propanoate (5.0 g, 8.94 mmol) was dissolved in 10 mL of water, followed by addition of sodium sulfite (7.07 g, 44.7 mmol) at room temperature. The solution was heated at 80° C. for 72 hours, then cooled to room temperature. The crude reaction was extracted 1× with ethyl acetate. The aqueous layer was acidified with a 10% citric acid solution to give a suspension which was extracted 3×'s with 25 mL portions of ethyl acetate. The combined organic layers were washed with brine, dried over magnesium sulfate, and the ethyl acetate solution was filtered and concentrated on a rotary evaporator to give the crude product as an orange solid. The crude product was cleaned up by flash chromatography using ethyl acetate in hexanes as the eluent to give a 5:1 mixture of trans:cis isomers. The isomers were separated on preparative HPLC to give 70 mg of the product as a white waxy solid in 2% yield. $^1$H NMR (500 MHz, Methanol-d4) δ 5.26 (td, J=7.9, 1.6 Hz, 1H), 4.48 (dd, J=7.8, 4.9 Hz, 1H), 4.08 (d, J=1.3 Hz, 2H), 3.29-3.18 (m, 2H), 3.04 (s, 3H), 3.02-2.99 (m, 1H), 2.89 (dd, J=13.8, 7.8 Hz, 1H), 2.14-2.06 (m, 2H), 1.75 (d, J=1.4 Hz, 3H), 1.55 (dq, J=13.4, 6.7 Hz, 1H), 1.50-1.06 (m, 19H), 0.98-0.83 (m, 12H). This compound corresponds to Compound BI.

Example 25

Synthesis of (2S)-1-{[(1R)-1-carboxy-2-{[(2E,6E)-3,7,11-trimethyldodeca-2,6,10-trien-1-yl]sulfanyl}ethyl]carbamoyl}pyrrolidine-2-carboxylic acid

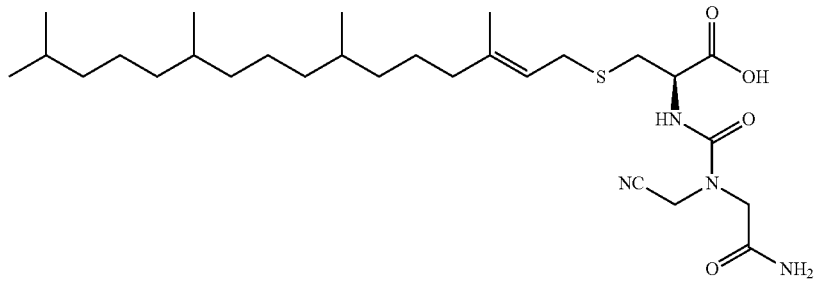

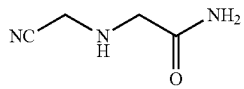

Step 1: Synthesis of N-(cyanomethyl)glycine amide: Bromoacetonitrile (0.779 mL, 14.8 mmol) was added to a slurry of glycinamide (1 g, 13.5 mmol) and sodium bicarbonate (2.03 g, 24.2 mmol) in 20 mL of acetonitrile at room temperature. The reaction was heated at 60° C. for 6 hours and monitored by TLC. After no starting material remained, the crude reaction was cooled to room temperature, filtered and concentrated to give the product as a yellow solid. The solid was carried onto the next step without further purification.

Step 2: Synthesis of (2S)-1-{[(1R)-1-carboxy-2-{[(2E,6E)-3,7,11-trimethyldodeca-2,6,10-trien-1-yl]sulfanyl}ethyl]carbamoyl}pyrrolidine-2-carboxylic acid: The title compound was prepared according to the procedure for Examples 1-5 to give 8 mg of tan solid in 1% yield. $^1$H NMR (500 MHz, Methanol-d4) δ 5.22 (t, J=7.8 Hz, 1H), 4.65 (dd, J=11.8, 4.5 Hz, 1H), 4.11 (ddd, J=17.0, 14.4, 8.1 Hz, 4H), 3.28-3.08 (m, 4H), 2.02-1.96 (m, 2H), 1.68 (d, J=4.0 Hz, 3H), 1.58-1.49 (m, 1H), 1.48-1.02 (m, 19H), 0.93-0.79 (m, 12H).

Example 26

Synthesis of 5-{[(1R)-1-carboxy-2-{[(2E)-3,7,11,15-tetramethylhexadec-2-en-1-yl]sulfanyl}ethyl]amino}pyrazine-2-carboxylic acid

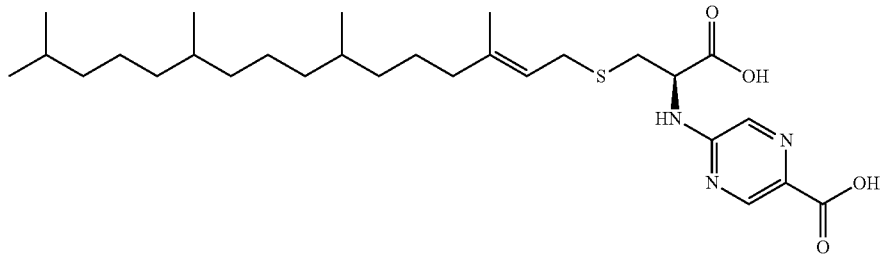 [SMILES: C/C(=C\CSC[C@H](Nc1cnc(C(=O)O)cn1)C(=O)O)CCCC(C)CCCC(C)CCCC(C)C]

Phytyl cysteine methyl ester (500 mg, 1.21 mmol), 2-Pyrazinecarboxylic acid-5-chloro-ethyl ester (208 mg, 1.21 mmol) and N,N-diisopropylethylamine (0.421 mL, 2.42 mmol) were dissolved in 5 mL of dioxane and heated at 120° C. in a sealed tube for 72 hours. The reaction mixture was cooled to room temperature, diluted with tetrahydrofuran and washed once with brine. 1N lithium hydroxide solution (3.6 mL) was added to the reaction mixture and stirred at room temperature overnight. The crude reaction was diluted with ethyl acetate and washed successively with a 10% citric acid solution and brine. The mixture was dried over magnesium sulfate, filtered, and concentrated on a rotary evaporator to give the crude product as an orange solid which was purified by flash chromatography using ethyl acetate in hexanes to give 91 mg of the product as a pale yellow solid in 14% yield. $^1$H NMR (500 MHz, Methanol-d4) δ 10.19 (d, J=1.4 Hz, 1H), 9.56 (d, J=1.3 Hz, 1H), 6.75-6.66 (m, 1H), 6.38-6.31 (m, 1H), 4.76 (dd, J=13.4, 8.0 Hz, 1H), 4.69 (dd, J=13.6, 7.6 Hz, 1H), 4.60 (dd, J=13.9, 4.7 Hz, 1H), 4.40 (dd, J=14.0, 8.1 Hz, 1H), 3.49 (t, J=7.4 Hz, 2H), 3.15 (s, 3H), 3.03 (hept, J=6.6 Hz, 1H), 2.96-2.51 (m, 12H), 2.42-2.30 (m, 12H).

Example 27

Synthesis of 2-{[(1R)-1-carboxy-2-{[(2E)-3,7,11,15-tetramethylhexadec-2-en-1-yl]sulfanyl}ethyl]amino}-4-methylpyrimidine-5-carboxylic acid

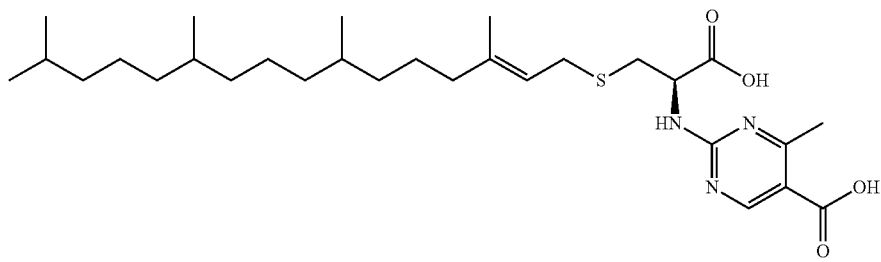 [SMILES: C/C(=C\CSC[C@H](Nc1ncc(C(=O)O)c(C)n1)C(=O)O)CCCC(C)CCCC(C)CCCC(C)C]

The title compound was prepared according to the procedure for Example 26 to give 250 mg of a white solid in 38% yield. $^1$H NMR (500 MHz, Methanol-d4) δ 8.81 (d, J=14.4 Hz, 1H), 5.26-5.16 (m, 1H), 4.92-4.85 (m, 1H), 3.28 (dd, J=13.4, 8.1 Hz, 1H), 3.20 (dd, J=13.4, 7.5 Hz, 1H), 3.12 (dd, J=14.0, 4.7 Hz, 1H), 3.02-2.90 (m, 1H), 2.67 (s, 3H), 2.03-1.97 (m, 2H), 1.66 (s, 3H), 1.54 (dq, J=13.3, 6.6 Hz, 1H), 1.49-1.03 (m, 19H), 0.94-0.80 (m, 12H).

Example 28

Synthesis of (2R)-2-({2-[(carboxymethyl)(methyl)amino]pyrimidin-4-yl}amino)-3-{[(2E)-3,7,11,15-tetramethylhexadec-2-en-1-yl]sulfanyl}propanoic acid

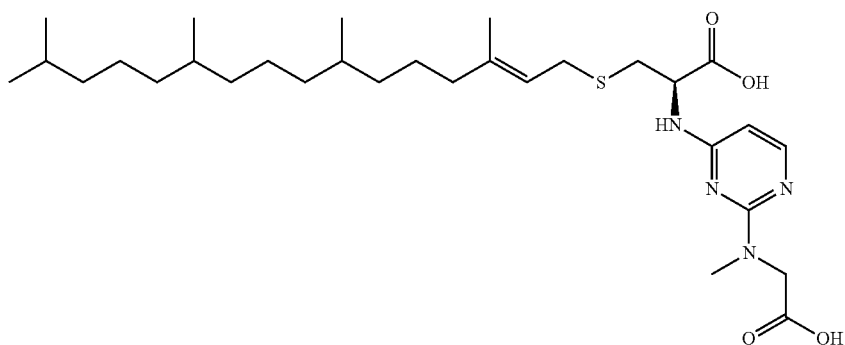

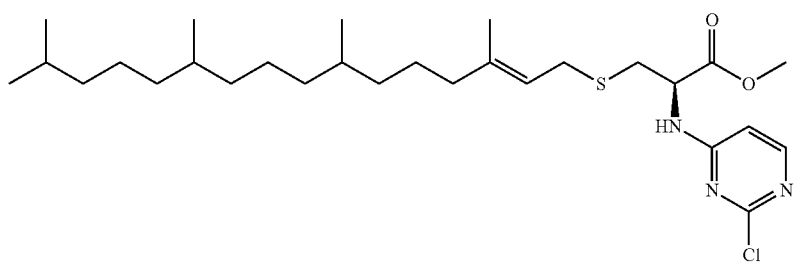

Step 1: Synthesis of methyl (2R)-2-[(2-chloropyrimidin-4-yl)amino]-3-{[(2E)-3,7,11,15-tetramethylhexadec-2-en-1-yl]sulfanyl}propanoate: 2,4-Dichloropyrimidine (270 mg, 1.81 mmol) was added to a solution of phytyl cysteine methyl ester (750 mg, 1.81 mmol) and N,N-diisopropylethylamine (630 mL, 3.62 mmol) in tetrahydrofuran (10 mL) that was cooled in an ice/water bath. The reaction was heated at 110° C. in a sealed tube overnight and monitored by HPLC. The HPLC indicated a 4:1 mixture of regioisomers. The reaction mixture was cooled to room temperature, concentrated on a rotary evaporator, and the crude yellow oil was purified by flash chromatography using ethyl acetate in hexanes as the eluent to give 557 mg of the product in 58% yield. $^1$H NMR (500 MHz, Methanol-d4) δ 7.94 (d, J=6.0 Hz, 1H), 6.58 (d, J=6.0 Hz, 1H), 5.29-5.10 (m, 1H), 4.95 (t, J=6.7 Hz, 1H), 3.77 (s, 3H), 3.29 (dd, J=13.4, 8.2 Hz, 1H), 3.19 (dd, J=13.5, 7.7 Hz, 1H), 3.04 (dd, J=14.0, 5.1 Hz, 1H), 2.93-2.59 (m, 1H), 2.08-2.03 (m, 2H), 1.69 (s, 3H), 1.59-1.51 (m, 1H), 1.51-1.04 (m, 19H), 0.97-0.84 (m, 12H).

Step 2: Synthesis of (2R)-2-({2-[(carboxymethyl)(methyl)amino]pyrimidin-4-yl}amino)-3-{[(2E)-3,7,11,15-tetramethylhexadec-2-en-1-yl]sulfanyl}propanoic acid: Methyl (2R)-2-[(2-chloropyrimidin-4-yl)amino]-3-{[(2E)-3,7,11,15-tetramethylhexadec-2-en-1-yl]sulfanyl}propanoate (500 mg, 0.950 mmol), sarcosine methyl ester hydrochloride (398 mg, 2.85 mmol) and N,N-diisopropylethylamine (0.827 mL, 4.75 mmol) were combined in a sealed tube and heated at 120° C. for 2 hours. The reaction mix was diluted in tetrahydrofuran and washed once with brine. The organic layer then had 1M lithium hydroxide solution (2.85 mL) added and the reaction mixture was stirred at room temperature overnight. The reaction mixture is diluted with ethyl acetate, washed with 10% w/v citric acid solution, then brine and dried over magnesium sulfate. The ethyl acetate is filtered and concentrated on a rotary evaporator to give the crude product as a yellow oil that is purified by flash chromatography using ethyl acetate in hexanes as the eluent to give 320 mg of the product as a white solid in 59% yield. $^1$H NMR (500 MHz, Deuterium Oxide) δ 7.51 (s, 2H), 6.05 (s, 1H), 5.07 (s, 1H), 3.79-3.41 (m, 2H), 3.26-2.75 (m, 7H), 1.79 (s, 2H), 1.54 (d, J=41.6 Hz, 3H), 1.44-0.80 (m, 19H), 0.71 (d, J=9.2 Hz, 12H).

Example 29

Synthesis of (2R)-2-({4-[(carboxymethyl)(methyl)amino]pyrimidin-2-yl}amino)-3-{[(2E)-3,7,11,15-tetramethylhexadec-2-en-1-yl]sulfanyl}propanoic acid

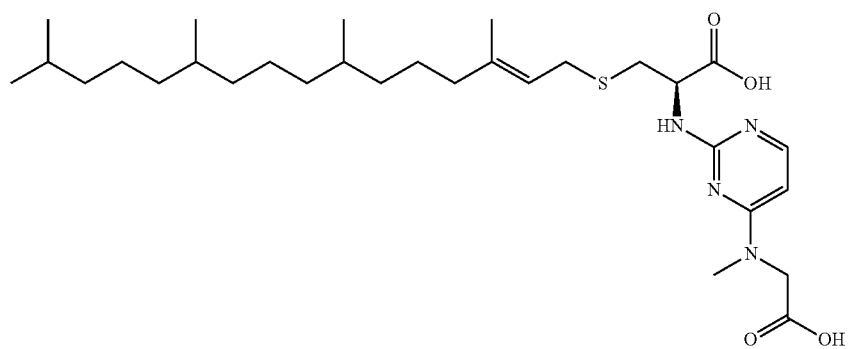

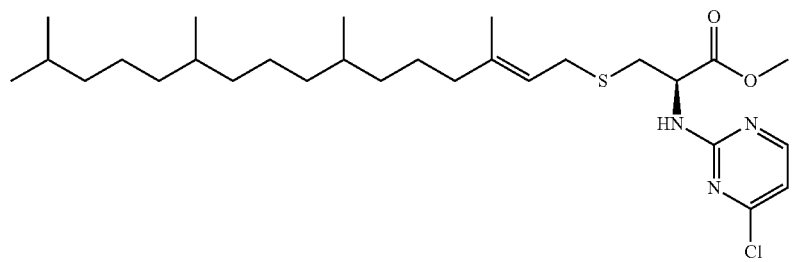

Step 1: Synthesis of methyl (2R)-2-[(4-chloropyrimidin-2-yl)amino]-3-{[(2E)-3,7,11,15-tetramethylhexadec-2-en-1-yl]sulfanyl}propanoate: The title compound was prepared according to the procedure for Example 28, Step 1 to give 169 mg of product in 17% yield. $^1$H NMR (500 MHz, Chloroform-d) δ 8.16 (d, J=5.1 Hz, 1H), 6.68-6.59 (m, 1H), 5.19 (t, J=7.8 Hz, 1H), 4.86 (d, J=5.8 Hz, 1H), 3.77 (d, J=5.5 Hz, 3H), 3.25-3.08 (m, 2H), 3.08-2.99 (m, 1H), 2.95 (dd, J=13.8, 6.5 Hz, 1H), 2.04-1.90 (m, 2H), 1.62 (d, J=5.3 Hz, 3H), 1.55-1.46 (m, 1H), 1.44-0.99 (m, 19H), 0.86 (dd, J=10.7, 6.5 Hz, 12H).

Step 2: Synthesis of (2R)-2-({4-[(carboxymethyl)(methyl)amino]pyrimidin-2-yl}amino)-3-{[(2E)-3,7,11,15-tetramethylhexadec-2-en-1-yl]sulfanyl}propanoic acid: The title compound was prepared according to the procedure for Example 28, Step 2 to give 13 mg of product in 9% yield. $^1$H NMR (500 MHz, Methylene Chloride-d2) δ 7.58 (s, 1H), 7.25 (s, 1H), 6.36-5.89 (m, 1H), 5.15-4.91 (m, 1H), 4.41-4.06 (m, 2H), 3.63-3.06 (m, 7H), 1.93 (d, J=42.5 Hz, 2H), 1.58 (d, J=48.8 Hz, 3H), 1.47-0.86 (m, 20H), 0.80-0.64 (m, 12H).

Example 30

Synthesis of (2R)-2-amino-3-methyl-3-{[(2E)-3,7,11,15-tetramethylhexadec-2-en-1-yl]sulfanyl}butanoic acid

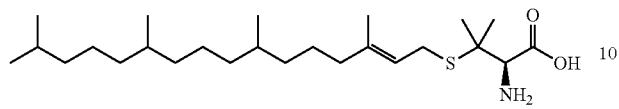

The title compound was prepared according to the phytyl cysteine procedure to give 2.4 g of a yellow solid in 83% yield. $^1$H NMR (500 MHz, Chloroform-d) δ 5.42 (tq, J=6.2, 1.0 Hz, 1H), 3.81 (s, 1H), 3.15 (ddq, J=12.5, 6.2, 1.0 Hz, 1H), 3.10-3.02 (m, 1H), 2.00 (td, J=7.1, 1.1 Hz, 2H), 1.72 (s, 3H), 1.65-1.54 (m, 1H), 1.54-1.12 (m, 25H), 0.93-0.70 (m, 12H).

Example 31

Synthesis of disodium (2R)-2-(3-carboxylatopropanamido)-3-methyl-3-{[(2E)-3,7,11,15-tetramethylhexadec-2-en-1-yl]sulfanyl}butanoate

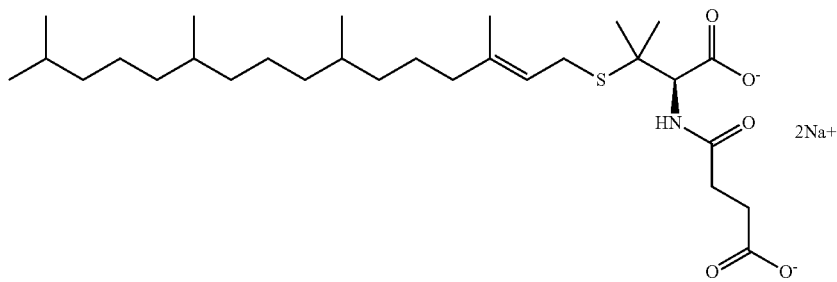 [SMILES: C/C(=C\CSC(C)(C)[C@H](NC(=O)CCC(=O)[O-])C(=O)[O-])CCCC(C)CCCC(C)CCCC(C)C]

Succinic anhydride (233 mg, 2.33 mmol) was added to a stirring suspension of (2R)-2-amino-3-methyl-3-{[(2E)-3,7,11,15-tetramethylhexadec-2-en-1-yl]sulfanyl}butanoic acid (1 g, 2.33 mmol) in 10 mL of a 9:1 ethanol:water mixture at room temperature and heated at 60° C. overnight. The reaction was cooled to room temperature, concentrated on a rotary evaporator, diluted in ethyl acetate and washed successively with 10% w/v citric acid solution and brine. The ethyl acetate was dried over magnesium sulfate, filtered and concentrated on a rotary evaporator to give the crude product as a yellow oil that was purified by flash chromatography using ethyl acetate in hexanes as the eluent to give the carboxylic acid. The purified carboxylic acid was dissolved in 10 mL of ethanol and 21% sodium ethoxide solution in ethanol was slowly added to the solution until the pH registered 9. The resulting ethanolic suspension was centrifuged at 2000 rpm for 2 minutes. The ethanol was decanted and the ethanol wash was repeated twice more. Acetonitrile was then substituted for ethanol and the wash was repeated three times. The resulting solid was dried on a rotary evaporator to give 121 mg of a white solid in 9% yield. $^1$H NMR (500 MHz, Deuterium Oxide) δ 5.11 (t, J=8.0 Hz, 1H), 4.13 (s, 1H), 3.15-3.03 (m, 2H), 2.61-2.27 (m, 4H), 1.99-1.79 (m, 2H), 1.57 (s, 3H), 1.50-1.39 (m, 1H), 1.39-0.95 (m, 25H), 0.79 (d, J=6.2 Hz, 12H).

Example 32

Synthesis of disodium 2-{[(1R)-1-carboxylato-2-methyl-2-{[(2E)-3,7,11,15-tetramethylhexadec-2-en-1-yl]sulfanyl}propyl]amino}pyrimidine-5-carboxylate

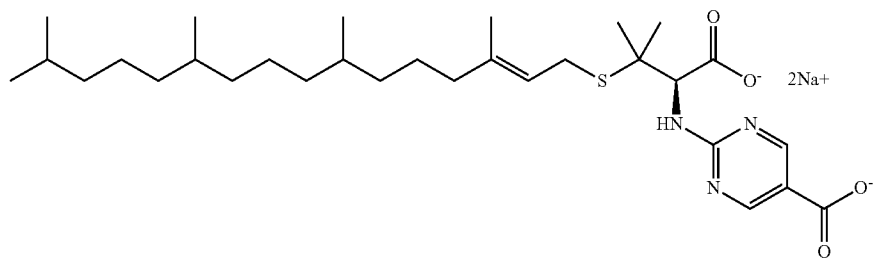 [SMILES: C/C(=C\CSC(C)(C)[C@H](Nc1ncc(C(=O)[O-])cn1)C(=O)[O-])CCCC(C)CCCC(C)CCCC(C)C]

2-Chloropyrimidine-5-carboxylic acid methyl ester (434 mg, 2.33 mmol) was added to a stirring suspension of (2R)-2-amino-3-methyl-3-{[(2E)-3,7,11,15-tetramethylhexadec-2-en-1-yl]sulfanyl}butanoic acid (1 g, 2.33 mmol) and N,N-diisopropylethylamine (1.21 mL, 6.99 mmol) in dioxane (10 mL) at room temperature and heated to 60° C. overnight. The reaction mixture is cooled to room temperature and washed once with brine. The reaction mixture is diluted with an additional 5 mL of dioxane, followed by addition of 1M lithium hydroxide (10 mL) at room temperature and stirred overnight. The reaction mixture is diluted with ethyl acetate, washed with 10% w/v citric acid solution, then brine and dried over magnesium sulfate. The ethyl acetate is filtered and concentrated on a rotary evaporator to give the crude product as a yellow oil that is purified by flash chromatography using ethyl acetate in hexanes as the eluent to give the purified carboxylic acid as an off-white solid. The carboxylic acid was dissolved in ethanol, then solid sodium ethoxide was added until the pH reached 9. The resulting ethanolic suspension was centrifuged at 2000 rpm for 2 minutes. The ethanol was decanted and the ethanol wash was repeated twice more. Acetonitrile was then substituted for ethanol and the wash was repeated three times. The resulting solid was dried on a rotary evaporator to give 165 mg of a white solid in 12% yield. $^1$H NMR (500 MHz, Deuterium Oxide) δ 8.61 (s, 2H), 5.07 (s, 1H), 4.21 (s, 1H), 3.17-3.02 (m, 2H), 1.92-1.74 (m, 2H), 1.49 (d, J=6.4 Hz, 3H), 1.44-0.82 (m, 26H), 0.79-0.64 (m, 12H).

Example 33

Synthesis of trisodium (2R)-2-{[bis(carboxylatomethyl)carbamoyl]amino}-3-{[(2E,6E)-3,7,11-trimethyldodeca-2,6,10-trien-1-yl]sulfanyl}propanoate

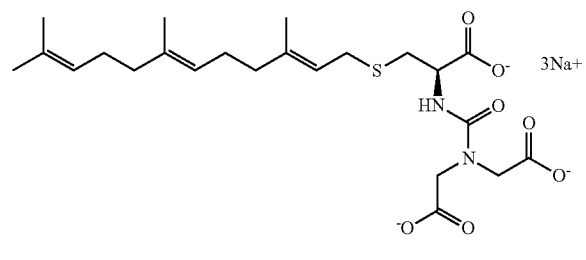

The title compound was prepared according to the procedure for Examples 1-5 to give the carboxylic acid. The isolated carboxylic acid was then dissolved in 10 mL of ethanol and enough solid sodium ethoxide was added to bring the pH of the mixture to 7. The resulting ethanolic suspension was centrifuged at 2000 rpm for 2 minutes. The ethanol was decanted and the ethanol wash was repeated twice more. Acetonitrile was then substituted for ethanol and the wash was repeated three times. The resulting solid was dried on a rotary evaporator to give 613 mg of a white solid in 75% yield. $^1$H NMR (500 MHz, Deuterium Oxide) δ 5.19 (td, J=8.0, 4.1 Hz, 1H), 5.15-5.05 (m, 2H), 4.13 (dd, J=7.4, 4.6 Hz, 1H), 3.84 (d, J=18.0 Hz, 2H), 3.70 (d, J=18.0 Hz, 2H), 3.13 (tt, J=13.1, 6.4 Hz, 2H), 2.87 (dd, J=13.6, 4.7 Hz, 1H), 2.75 (ddd, J=13.7, 7.4, 2.7 Hz, 1H), 2.11-1.88 (m, 8H), 1.67-1.48 (m, 12H).

Example 34

Synthesis of (2S)-1-{[(1R)-1-carboxy-2-{[(2E,6E)-3,7,11-trimethyldodeca-2,6,10-trien-1-yl]sulfanyl}ethyl]carbamoyl}pyrrolidine-2-carboxylic acid

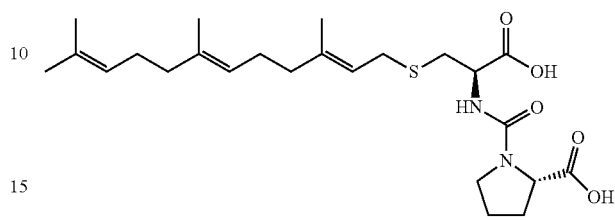

The title compound was prepared according to the above-described procedures to give 209 mg of tan solid in 30% yield. $^1$H NMR (500 MHz, Methanol-d4) δ 5.24 (q, J=7.8 Hz, 1H), 5.19-5.07 (m, 2H), 4.54-4.48 (m, 1H), 4.41 (ddd, J=11.2, 8.5, 2.5 Hz, 1H), 3.63-3.42 (m, 2H), 3.28 (ddd, J=13.8, 8.3, 6.0 Hz, 1H), 3.23-3.08 (m, 1H), 3.01 (dt, J=14.0, 4.9 Hz, 1H), 2.85 (ddd, J=21.0, 13.9, 7.9 Hz, 1H), 2.29-1.94 (m, 12H), 1.82-1.57 (m, 12H).

Example 35

Synthesis of (2R)-2-[2-(carboxymethoxy)acetamido]-3-{[(2E,6E)-3,7,11-trimethyldodeca-2,6,10-trien-1-yl]sulfanyl}propanoic acid

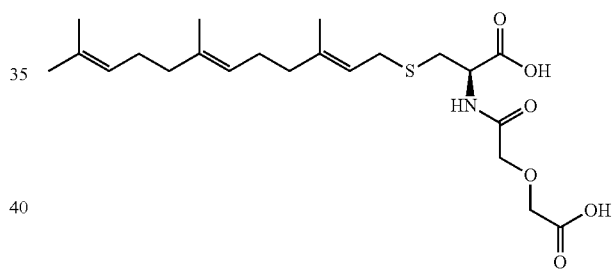

The title compound was prepared according to the above-described procedures to give 250 mg of light brown oil in 50% yield. $^1$H NMR (500 MHz, Methanol-d4) δ 5.25 (q, J=8.3 Hz, 1H), 5.20-5.06 (m, 2H), 4.68 (dd, J=8.4, 4.6 Hz, 1H), 4.27-4.15 (m, 4H), 3.31-3.14 (m, 2H), 3.06 (ddd, J=14.0, 4.6, 2.6 Hz, 1H), 2.92-2.80 (m, 1H), 2.22-1.95 (m, 8H), 1.79-1.59 (m, 12H).

BIOLOGICAL EXAMPLES

Described below are in vivo assays used to measure the biological activity of provided compounds, including the anti-inflammatory or proinflammatory properties of the compounds, as measured by edema inhibition, erythema inhibition and MPO inhibition.

Example A

Antimicrobial Assays

To determine minimal inhibitory concentration (MIC), reagents were dissolved in vehicle (5% v/v) and then added to bacteria suspension. *P. acnes* (ATCC® 6919TM) at $10^6$ CFU/mL was incubated with test materials at the concentrations of two-fold serial dilution (0.25-500 μg/mL) and incubated for 72 hours (*P. acnes*). To determine minimal bactericidal concentration (MBC) against P. acnes, bacteria (107 CFU/mL) was incubated with reagents at various concentrations (12.5-100 μg/mL in PBS) under anaerobic conditions. Cultures were diluted 1:10-1: $10^6$ with PBS, and MBC was determined by spotting the dilution (5 mL) on a Brucella broth agar plate to count colony-forming units (CFUs).

The following results were obtained:

| | P. acnes | |
|---|---|---|
| Compound Tested | MIC (μg/mL) | MBC (μg/mL) |
| A | 10 | |
| J | 32 | |
| K | >250 | |
| B | 24 | |
| L | >16 | |
| M | 16 | |
| N | >250 | |
| O | 32 | |
| P | 10 | |
| Q | 125 | |
| C | 6 | 22 |
| R | >25 | |
| D | >250 | |
| T | 22 | |
| F | 6 | |
| I | >16 | |
| E | 5 | 7 |
| G | 4 | 1 |
| U | 19 | |
| H | 6 | |
| V | >4 | >25 |
| W | 62 | |
| X | >25 | |
| Y | 50 | |
| AD | >125 | |
| AF | >125 | |
| AQ | >125 | |
| AW | >125 | |
| AX | >125 | |
| AY | >125 | |
| AZ | 63 | |
| BA | >125 | |
| BB | 31 | |
| BC | 12 | |
| BD | >125 | |
| BE | 23 | |
| BF | >125 | |
| BG | 42 | |
| BH | 4 | 16 |
| BI | 12 | |
| BJ | 23 | |
| BK | 31 | |
| BL | 7 | >62 |
| BM | 6 | >62 |
| BN | 8 | 31 |
| BO | 125 | |
| BP | >125 | |
| Doxycycline | <0.2 | |
| Clindamycin HCl | 0.06 | |
| Benzoyl Peroxide | 200 | >200 |
| Salicylic Acid | 1000 | 2000 |
| Azelaic Acid | 1000 | >2000 |

P. acnes (ATCC® 6919™) was cultured as described above. Bacteria biofilms were established by seeding P. acnes cultures in 96-well plates and incubating for 24 hours without agitation. Later, biofilms were incubated with test materials for 24 hours. Remaining biofilms were washed and stained with crystal violet. Staining solution was removed, wells rinsed with water and dye was extracted with 1% w/v SDS. The absorbance was measured at 595 nm in a microplate reader. MBEC was defined as the minimum concentration necessary to achieve ≥80% eradication of attached biofilm compared to vehicle-only control. Results from disk diffusion susceptibility testing (Kirby-Bauer Method) after 72 hours incubation were also obtained.

The following results were obtained:

| Compound Tested | MBEC - μg/mL (μM) |
|---|---|
| C | 9 |
| E | 12 (21) |
| G | 7 (11) |
| Benzoyl Peroxide | 367 (1515) |
| Salicylic Acid | >8000 (>57920) |
| Azelaic Acid | 8000 (42503) |
| Clindamycin | 0.6 (1) |

Example B

Gene Expression on Human Keratinocytes (Antimicrobial Peptides)

Normal human epidermal keratinocytes (NHEKs) from neonatal donors were obtained from Thermo-Fisher (Cat No. C-001-5C). Cells were cultured in 6-well plates for 24 hours before treatments with EpiLife media (Cat No. MEPT500CA) supplemented with keratinocytes growth supplement (Cat No. 50015). On Day 2, media was removed and incubated with test materials (10 μM) for 24 hours at 37° C. and 5% $CO_2$. On Day 3, total RNA was extracted from cells using the RNAqueous® kit (Ambion®; Cat No. 1912) and cDNA was obtained using the High Capacity RNA-to-cDNA kit (Applied Biosystems®; Cat No. 4387406). Quantitative PCR (qPCR) was performed using the TaqMan® Fast Advanced Master Mix (Applied Biosystems®; Cat No. 4444556) and specific TaqMan®-probes human gene primers DEFB4B (hBD2), DEFB103 (hBD3), HCAP18 and GAPDH to calculate the relative gene fold expression change per treatment. Gene expression analysis was performed using the the comparative Ct method (also known as the 2-[delta][delta]Ct) approach by comparing the Ct values of the treated samples with the untreated samples and normalized to GAPDH gene expression as endogenous housekeeping gene. Results were represented as fold-expression/untreated cells.

The following results were obtained:

| | NHEK-gene Expression | | |
|---|---|---|---|
| | hBD2 | hBD3 | hCAP18 |
| Compound Tested | Fold-expression/untreated cells | | |
| E | 1.1 | 2.9 | 0.7 |
| G | 2.5 | 4.7 | 0.6 |
| C | 0.7 | 9.5 | 0.5 |
| Benzoyl Peroxide | 1.6 | 1.2 | 2.8 |
| Salicylic Acid | 1.0 | 1.2 | 1.2 |
| Azelaic Acid | 1.8 | 0.9 | 1.1 |

Example C

P. acnes-Induced Pro-Inflammatory Cytokines on Human PBMCs

Cryopreserved human Peripheral Blood Mononuclear cells (PBMCs) from healthy adult donors were obtained from Zen Bio, Inc (Cat No. SER-PBMC-F). Cells were cultured in 12-well plates with lymphocyte media (Cat No. LYMPH-1) and incubated with test materials (30 μM) and live P. acnes (ATCC® 6919TM) at 1:1 PBMC: P. acnes bacteria ratio for 24 hours at 37° C. and 5% $CO_2$. After incubation, cell media supernatants were harvested and used to measure pro-inflammatory cytokine levels (IL-8, TNF-α, IL-1b, IL-17) using ELISA kits (BD Biosciences® #557966,

555212, #555244; R&D Systems® #DY317). Total RNA was extracted from cells using the RNAqueous® kit (Ambion®; Cat No. 1912) and cDNA was obtained using the High Capacity RNA-to-cDNA kit (Applied Biosystems®; Cat No. 4387406). Quantitative PCR (qPCR) was performed using the TaqMan® Fast Advanced Master Mix (Applied Biosystems®; Cat No. 4444556) and specific TaqMan®-probes human gene primers CXCL8 (IL-8), IL1B (IL-1b), TNF (TNF-α), IL17A (IL-17A) and GAPDH to calculate the relative gene fold expression change per treatment. Gene expression analysis was performed using the comparative Ct method (also known as the 2-[delta][delta]Ct) approach by comparing the Ct values of *P. acnes*-only treated cells with the untreated samples and normalized to GAPDH gene expression as endogenous housekeeping gene. Results were represented as percent of inhibition relative to untreated and *P. acnes*-only treated cells.

The following results were obtained:

| | *P. acnes*-PBMCs | | | | | | | |
|---|---|---|---|---|---|---|---|---|
| Compound Tested | IL-8 Protein | IL-1b Protein | IL-17 Protein | TNFa- Protein | IL-8 Gene | TNFa- Gene | IL-1b Gene | IL-17 Gene |
| | | | | % inhibition | | | | |
| A | | 38 | 32 | | | | | |
| Q | | | | | 14 | 0 | 59 | 72 |
| C | 8 | 36 | 0 | 0 | 0 | 0 | 0 | 0 |
| T | | | | | 0 | 0 | 27 | 0 |
| I | | | | | 52 | 0 | 86 | 7 |
| E | 67 | 82 | 23 | 0 | 8 | 0 | 20 | 0 |
| G | 74 | 91 | 29 | 0 | 0 | 0 | 10 | 0 |
| V | | | | | 46 | 0 | 83 | 0 |
| Clindamycin HCl | 36 | 32 | 89 | 10 | 0 | 10 | 3 | 41 |
| Benzoyl Peroxide | 78 | 33 | 15 | 0 | | | | |
| Salicylic Acid | 0 | 40 | 0 | 0 | | | | |
| Azelaic Acid | 43 | 66 | 0 | 0 | | | | |

Example D

Peptidoilycan (PGN)-Induced Pro-Inflammatory Cytokines on NHEKs

Normal human epidermal keratinocytes (NHEKs) from neonatal donors were obtained from Then-no-Fisher (Cat No. C-001-5C). Cells were cultured in 96-well plates for 24 hours with EpiLife media (Cat No. MEPI500CA) supplemented with keratinocytes growth supplement (Cat No. S0015). On Day 2, media was removed and replaced with supplement-depleted medium for 24 hours. On Day 3, media was removed and cells were pre-treated with test materials (≤1 µM) for 2 hours and later co-treated with test materials and PGN (Sigma Aldrich, Cat No. 77140) at 10 µg/mL and incubated for 24 hours at 37° C. and 5% $CO_2$. PGN is a TLR-2 agonist. After incubation, cell media supernatants were harvested and used to measure pro-inflammatory cytokine levels (IL-8) using ELISA kit (BD Biosciences® #555244). Results were represented as percent of inhibition relative to untreated and PGN-only treated cells. $IC_{50}$ values were determined by non-linear regression analysis using the four-parameter logistic equation.

The following results were obtained:

| Compound Tested | PGN-NHEK 1L-8 Protein IC50 (µM) |
|---|---|
| C | 0.25 |
| E | 0.25 |
| G | 0.05 |
| Benzoyl Peroxide | >1 |
| Salicylic Acid | >1 |

Example E

*S. aureus*-Induced TSLP on NHEKs

Normal human epidermal keratinocytes (NHEKs) from neonatal donors were obtained from Thermo-Fisher (Cat No. C-001-5C). Cells were cultured in 96-well plates for 24 hours with EpiLife media (Cat No. MEPI500CA) supplemented with keratinocytes growth supplement (Cat No. 50015). On Day 2, media was removed and replaced with supplement-depleted medium for 24 hours. On Day 3, media was removed and cells were pre-treated with test materials (≤30 µM) for 2 hours and later co-treated with test materials and live *S. aureus* (ATCC® 33591) at 1:1 NHEK: bacteria ratio for 24 hours at 37° C. and 5% $CO_2$. After incubation, cell media supernatants were harvested and used to measure TSLP levels using ELISA kit (R&D Systems® #DY1398). Results were represented as percent of inhibition relative to untreated and *S. aureus*—only treated cells. $IC_{50}$ values were determined by non-linear regression analysis using the four-parameter logistic equation.

The following results were obtained:

| Compound Tested | *S. aureus*-NHEK TSLP Protein IC50 (µM) |
|---|---|
| A | 9 |
| C | 3 |
| T | 10 |
| AN2728 (2%) | 5 |

Example F

T-Cell Receptor (TCR)-Induced. Lipopolysaccharide (LPS)-Induced and Phytohaemagglutinin (PHA)-Induced Cytokines on PBMCs Cryopreserved human Peripheral Blood Mononuclear cells (PBMCs) from healthy adult donors were obtained from Zen Bio, Inc (Cat No. SER-PBMC-F). Cells were cultured in 96-well plates with lymphocyte media (Cat No. LYMPH-1) and were pre-treated with test materials (≤100 µM) for 2 hours and later co-treated with test materials and anti-CD3/CD28 beads (Thermo-Fisher; Cat No. 11131D) at 1:0.4 PBMC: bead ratio for 24 hours at 37° C. and 5% $CO_2$. After incubation, cell media supernatants were harvested and used to measure cytokine levels (IL-4, IL-5, IL-10) using ELISA kits (BD Biosciences® #555194, #555157; R&D Systems® #DY317). Results were represented as percent of inhibition relative to untreated and anti-CD3/CD28 beads-only treated cells. $IC_{50}$ values were determined by non-linear regression analysis using the four-parameter logistic equation.

The following results were obtained:

| Compound Tested | TCR-PBMCs | | |
| --- | --- | --- | --- |
| | IL-4 Protein IC50 ($\mu$M) | IL-5 Protein IC50 ($\mu$M) | IL-10 Protein IC50 ($\mu$M) |
| A | >100 | 55 | 42 |
| B | 52 | 50 | 46 |
| C | 20 | 46 | 34 |
| D | >100 | >100 | 100 |
| T | 25 | 9 | 19 |
| E | 42 | 63 | 39 |
| AN2728 (2%) | 2 | 1 | 9 |

By a similar method, but instead of anti-CD3/CD28 beads (Thermo-Fisher; Cat No. 11131D), compounds A, C, T and E were treated with LPS (Sigma Aldrich, Cat. No. LF4321) to measure inhibition of LPS-induced cytokines, and compounds C and T were treated with PHA-L (Sigma Aldrich, Cat No. 11249738001) to measure inhibition of PHA-induced cytokines. These compounds did not show significant inhibition as compared to controls.

Example G

Nickel ($Ni^{2+}$)-Induced Cytokines on HDMECs

Human Dermal Microvascular Endothelial cells (HD-MECs) from human skin tissues were obtained from Sciencell, Inc. (Cat No. 2000). Cells were cultured in 96-well plates for 24 hours with ECM media (Cat No. 1001) supplemented with endothelial cell growth supplement (Cat No. 50015) and 5% v/v FBS. On Day 2, media was removed and replaced with supplement-depleted medium for 24 hours. On Day 3, media was removed and cells were pre-treated with test materials ($\leq$10 $\mu$M) for 2 hours and later co-treated with test materials and 1 mM $NiSO_4$ (Sigma-Aldrich, Cat No. 227676) for 6 hours at 37° C. and 5% $CO_2$. After incubation, cell media supernatants were harvested and used to measure IL-6 levels using ELISA kit (BD Biosciences® #555220). Results were represented as percent of inhibition relative to untreated and $NiSO_4$-only treated cells. $IC_{50}$ values were determined by non-linear regression analysis using the four-parameter logistic equation.

The following results were obtained:

| Compound Tested | Nickel-HDMECs IL-6 Protein IC50 ($\mu$M) |
| --- | --- |
| A | 0.03 |
| C | 0.02 |
| T | 0.01 |
| AN2728 (2%) | 100 |

Example H

TPA-Induced Pro-Inflammatory Cytokines on NHEKs

Normal human epidermal keratinocytes (NHEKs) from neonatal donors were obtained from Thermo-Fisher (Cat No. C-001-5C). Cells were cultured in 96-well plates for 24 hours with EpiLife media (Cat No. MEPI500CA) supplemented with keratinocytes growth supplement (Cat No. S0015). On Day 2, media was removed and replaced with supplement-depleted medium for 24 hours. On Day 3, media was removed and cells were pre-treated with test materials ($\leq$1 $\mu$M) for 2 hours and later co-treated with test materials and TPA (Sigma Aldrich, Cat No. P8139) at 5 ng/mL and incubated for 24 hours at 37° C. and 5% $CO_2$. After incubation, cell media supernatants were harvested and used to measure pro-inflammatory cytokine levels (IL-8) using ELISA kit (BD Biosciences® #555244). Results were represented as percent of inhibition relative to untreated and TPA-only treated cells. $IC_{50}$ values were determined by non-linear regression analysis using the four-parameter logistic equation.

The following results were obtained:

| Compound Tested | TPA-NHEK $IC_{50}$ ($\mu$M) IL-8 |
| --- | --- |
| C | 0.02 |
| T | 0.03 |
| AN2728 | 0.02 |
| FK506 | 0.01 |

Example I

TPA-Induced Skin Irritation In Vivo Model

Outbred male Swiss Webster (ICR) mice were purchased from Hilltop Lab Animals (Scottdale, Pa.) and were used between 10 and 12 weeks of age and we followed a similar protocol previously described (Gordon et al., 2008). Mice received 1.2 $\mu$g/20 $\mu$l TPA dissolved in acetone (10 $\mu$l applied both to the dorsal and ventral surfaces of the mouse ear using a solvent pipette) to each ear to induce acute irritation (6 per group). Test Materials were co-treated with TPA or applied 5 minutes after TPA dose, at various concentrations (0.6 to 800 $\mu$g/20 $\mu$l) in ethanol. After 24 hour treatment, edema was measured by ear thickness.

The following results were obtained:

| Compound Tested | TPA Ear model @ 1% w/v | |
| --- | --- | --- |
| | Edema % inhibition | MPO % inhibition |
| A | 50 | |
| C | 64 | 88 |
| T | 61 | 83 |
| FK506 | 0 | 81 |
| AN2728 (2%) | 43 | |

Example J

Oxazolone-Induced Delayed-Type Hypersensitivity (DTH) In Vivo Model

Inbred male Balb/C mice were purchased from Hilltop Lab Animals (Scottdale, Pa.) and were used between 8 and 10 weeks of age. Mice backs were shaved and 100 $\mu$l of 3% v/v Oxazolone (Sigma Aldrich, Cat No. E0753) in acetone/olive oil (4:1) was applied to dorsal skin for sensitization. On Day 7, ears were challenged with 0.5% v/v Ozaxolone and 30 minutes after challenge, test materials at 3% w/v were applied to ears (10 $\mu$l applied both to the dorsal and ventral surfaces of the mouse ear using a solvent pipette) and 24 hours later, skin thickness (edema) was measured. A 6-mm punch biopsy was obtained from each ear, snap frozen in liquid nitrogen. Ear skin biopsy punches were pulverized using FastPrep®-24 Biopulverizer (MP Biomedical, CatNo. 116004500) and Lysing Matrix A tubes (Cat No. 16910050). Protein extracts were obtained using 500 $\mu$L/tissue of cold T-PER buffer (ThermoFisher, CatNo. 78510) with Protease inhibitors (Sigma-Aldrich, CatNo. 58820-20TAB). Soluble protein fractions were used to measure cytokine levels (IL-4) using ELISA kit (BD Biosciences® #555232). Results were represented as percent of inhibition relative to unsensitized and sensitized-only treated animals. Vehicle for presently disclosed compounds was 60:40 $H_2O$:EtOH and 1:1 Acetone:EtOH for AN2718. (n=5-15 animals per treatment group).

The following results were obtained:

| | Oxazolone DTH @ 3% w/v | |
|---|---|---|
| Compound Tested | Edema % inhibition | IL-4% inhibition |
| A | 44 | |
| J | 10 | |
| B | 48 | |
| C | 53 | 41 |
| R | 24 | |
| D | 53 | |
| T | 31 | 53 |
| I | 36 | |
| E | 51 | |
| G | 41 | |
| U | 18 | |
| H | 14 | |
| V | 5 | |
| W | 22 | |
| X | 15 | |
| Y | 0 | |
| FK506 | 32 (@1%) | |
| AN2728 (2%) | 0 (@2%) | 76 (@2%) |

Compound C was further analyzed at various dosages against 0.4 mg/ear of AN278 by the above protocol, data representing the average±S.E. of cumulative data from three independent experiments (n=12-15 mice per group) is shown below:

| Compound Tested | Dose (Mg/ear) | Edema (% inhibition) | IL-4 (% inhibition) | MPO (% inhibition) |
|---|---|---|---|---|
| Compound C | 0.2 | 23 ± 4 | 33 ± 9 | 22 ± 9 |
| | 0.6 | 53 ± 5 | 41 ± 10 | 67 ± 23 |
| | 1 | 72 ± 4 | 62 ± 11 | 81 ± 5 |
| Compound T | 0.2 | 20 ± 4 | | 30 ± 14 |
| | 0.6 | 31 ± 6 | | 41 ± 18 |
| | 1 | 53 ± 8 | | 71 ± 3 |
| Compound E | 0.6 | 22 | | |
| | 1 | 51 ± 9 | | |
| Compound G | 0.6 | 41 | | |
| AN2728 | 0.4 | 17 ± 5 | 76 ± 9 | 36 ± 12 |

Example K

*P. acnes*-Induced Pro-Inflammatory Cytokines on Human NHEKs

Normal human epidermal keratinocytes (NHEKs) from neonatal donors were obtained from Then-no-Fisher (Cat No. C-001-5C). Cells were cultured in 96-well plates for 24 hours with EpiLife media (Cat No. MEPI500CA) supplemented with keratinocytes growth supplement (Cat No. S0015). On Day 2, media was removed and replaced with supplement-depleted medium for 24 hours. On Day 3, media was removed and cells were pre-treated with test materials (30 µM) for 2 hours and later co-treated with test materials and live *P. acnes* (ATCC® 6919TM) at 107 CFU for 24 hours at 37° C. and 5% $CO_2$. After incubation, cell media supernatants were harvested and used to measure pro-inflammatory cytokine levels (IL-8) using ELISA kits (BD Biosciences® #555244). Results were represented as percent of inhibition relative to untreated and *P. acnes*-only treated cells. $IC_{50}$ values were determined by non-linear regression analysis using the four-parameter logistic equation.

The following results were obtained:

| | *P. acnes*-NHEK IL-8 Protein |
|---|---|
| Compound Tested | $IC_{50}$ (µM) |
| A | 0.12 |
| C | 0.04 |
| F | 1.69 |
| E | 0.003 |
| G | 0.068 |
| H | 0.02 |
| V | 0.003 |
| Clobetasol | 0.033 |

Example L

Phytohemagglutinin (PHA)-induced cytokines on PBMCs

Cryopreserved human Peripheral Blood Mononuclear cells (PBMCs) from healthy adult donors were obtained from Zen Bio, Inc (Cat No. SER-PBMC-F). Cells were cultured in 96-well plates with lymphocyte media (Cat No. LYMPH-1) and were pre-treated with test materials (≤100 µM) for 2 hours and later co-treated with test materials and PHA-L (Sigma Aldrich, Cat No. 11249738001) at 20 µg/mL and incubated for 24 hours at 37° C. and 5% $CO_2$. After incubation, cell media supernatants were harvested and used to measure cytokine levels (IL-2, IFNγ) using ELISA kits (R&D Systems® #DY202, #DY285). Results were represented as percent of inhibition relative to untreated and PHA-only treated cells. $IC_{50}$ values were determined by non-linear regression analysis using the four-parameter logistic equation.

The following results were obtained:

| | PHA-PBMCs $IC_{50}$ (µM) | |
|---|---|---|
| Compound Tested | IL-2 | IFNγ |
| C | 0.9 | >10 |
| T | 0.1 | >10 |
| E | 4.1 | 1.4 |
| G | 3.3 | >10 |
| AN2728 | 0.04 | 0.3 |
| FK506 | $7 \times 10^{-9}$ | $5 \times 10^{-7}$ |

Example M

Concanavalin-A (ConA)-Induced Cytokines on PBMCs

Cryopreserved human Peripheral Blood Mononuclear cells (PBMCs) from healthy adult donors were obtained from Zen Bio, Inc (Cat No. SER-PBMC-F). Cells were cultured in 96-well plates with lymphocyte media (Cat No. LYMPH-1) and were pre-treated with test materials (≤100 µM) for 2 hours and later co-treated with test materials and ConA (Sigma Aldrich, Cat No. C5275) at 20 g/mL and incubated for 24 hours at 37° C. and 5% $CO_2$. After incubation, cell media supernatants were harvested and used to measure cytokine levels (IL-2, IFNγ) using ELISA kits (R&D Systems® #DY202, #DY285). Results were represented as percent of inhibition relative to untreated and ConA-only treated cells. $IC_{50}$ values were determined by non-linear regression analysis using the four-parameter logistic equation.

The following results were obtained:

|  | Concanavalin A-PBMCs $IC_{50}$ (μM) | |
| --- | --- | --- |
| Compound Tested | IL-13 | IL-17 |
| C | 8.2 | 0.5 |
| T | 0.1 | 69.7 |
| E | 1.5 | 11.4 |
| G | 0.02 | 94.2 |
| AN2728 | 3.8 | 3.1 |
| FK506 | 0.6 | $4 \times 10^7$ |

Example N

LPS/IFNγ-induced cytokines on CD14+ monocytes

Cryopreserved human peripheral blood monocytes cells (CD14+) from healthy adult donors were obtained from Zen Bio, Inc (Cat No. SER-CD14-F). Cells were cultured in 96-well plates with lymphocyte media (Cat No. LYMPH-1) and were pre-treated with test materials (≤100 μM) for 2 hours and later co-treated with test materials and 50 μg/mL LPS, 5 g/nL IFNγ (Sigma Aldrich, Cat No. L4321, SRP3058) and incubated for 24 hours at 37° C. and 5% $CO_2$. After incubation, cell media supernatants were harvested and used to measure cytokine levels (IL-23) using ELISA kits (R&D Systems® #DY1290). Results were represented as percent of inhibition relative to untreated and ConA-only treated cells. $IC_{50}$ values were determined by non-linear regression analysis using the four-parameter logistic equation.

The following results were obtained:

| Compound Tested | LPS/IFNγ-CD14+ monocytes $IC_{50}$ (μM) IL-23 |
| --- | --- |
| C | 0.19 |
| T | 0.05 |
| E | 11.15 |
| G | 3.08 |
| AN2728 | 0.65 |
| FK506 | $7 \times 10^{-8}$ |

Example O

Anti-CD3/CD28+IL-4-Induced Cytokines on PBMCs

Cryopreserved human Peripheral Blood Mononuclear cells (PBMCs) from healthy adult donors were obtained from Zen Bio, Inc (Cat No. SER-PBMC-F). Cells were cultured in 96-well plates with lymphocyte media (Cat No. LYMPH-1) and were pre-treated with test materials (≤100 μM) for 2 hours and later co-treated with test materials and anti-CD3/CD28 beads (Thermo-Fisher; Cat No. 11131D) and 50 ng/mL recombinant human IL-4 (R&D Systems® #204-IL) for 48 hours at 37° C. and 5% $CO_2$. After incubation, cell media supernatants were harvested and used to measure cytokine levels (IL-22, IL-31) using ELISA kits (R&D Systems® #DY782, #DY2824). Results were represented as percent of inhibition relative to untreated and anti-CD3/CD28+IL-4 only treated cells. $IC_{50}$ values were determined by non-linear regression analysis using the four-parameter logistic equation.

The following results were obtained:

|  | TCR/IL-4-PBMCs $IC_{50}$ (μM) | |
| --- | --- | --- |
| Compound Tested | IL-22 | IL-31 |
| C | >25 | $1 \times 10^{-8}$ |
| T | >25 | 0.001 |
| E | >25 | 0.001 |
| G | >25 | $<1 \times 10^{-8}$ |
| AN2728 | 2 | 8.E−06 |
| FK506 | 7.E−08 | 4.E−04 |

Example P

Calcipotriol-Induced TSLP In Vivo

CD1 mice were topically exposed to 4 nmol/ear Calcipotriol. Five minutes after challenge compounds were applied. Twenty-four hours later, protein samples were extracted from ear skin biopsies and analyzed for TSLP levels by ELISA method. Vehicle for compounds were 60:40 EtOH:$H_2O$ (Compound C) or 1:1 EtOH:Acetone (AN2728). Data represents average±S.E. of a representative set from 2 independent experiments (n=6 mice per group). *p value <0.05; **p value ≤0.01 by Student t test compared to Calcipotriol+vehicle-only treated animals. ns equals not significant.

The following results were obtained:

|  | Compound C | | | AN2728 | | |
| --- | --- | --- | --- | --- | --- | --- |
| Dose (μg/ear) | AVG - TSLP (pg/6 mm biopsy) | SEM | % inhb | AVG - TSLP (pg/6 mm biopsy) | SEM | % inhb |
| Untreated |  |  |  | 435.2 | 16.8 |  |
| Calc + Vehicle | 3159.4 | 595.7 |  | 4630.7 | 1236.1 |  |
| 4.0 | 2753.6 | 836.6 | 15 | 2495.1 | 802.7 | 51 |
| 40.0 | 1156.1 | 374.1 | 74 | 2235.3 | 824.3 | 57 |
| 400.0 | 759.9 | 148.2 | 88 | 352.1 | 73.5 | 102 |

Example Q

8-Week Clinical Study of Compound E (1%), Vehicle and Benzoyl Peroxide (3%)

A multi-site use single-blinded study was conducted in healthy male and female subjects, aged ≥18 yo with evaluator assessed mild to moderate acne, to evaluate the potential efficacy of test skincare product by utilizing subjective questionnaires, visual evaluations and digital photography (≥15 per group). Subjects used the assigned product at home for 8 weeks. Subjects returned post baseline at week 2, 4 and 8. At each visit subjects underwent expert clinical grading and test site photography. At Visit 4, subjects also completed a Self-Perception Questionnaire (SPQ). *Values are given as mean±S.E. *p value ≤0.05; **p value ≤0.01 by Student t test between group differences from IGA scale values from baseline.

The following results were obtained:

| Compound Tested | Investigator Global Assesment (IGA) Scale | | | |
| --- | --- | --- | --- | --- |
| (% w/w) | Baseline | 2 week | 4 week | 8 week |
| Vehicle (n = 15) | 2 | 3 | 3 | 3 |
| E (1%; n = 18) | 3 | 2 | 1 | 0 |
| BPO (3%; n = 15) | 3 | 2 | 1 | 1 |

Facial Cream (1% Compound E) was tested in a randomized single-blind vehicle-controlled study (Active, n=18; Vehicle, n=14) to demonstrate the safety and tolerability in subjects with mild to moderate facial acne. The severity of acne signs and symptoms on the faces of >18 yo subjects were clinically assessed by IGA scale during an 8-week Study period. In addition, UV light mode was utilized to observe porphyrins fluorescence (orange-red dots). Several subjects using Compound E facial cream demonstrated marked visual improvement in the signs & symptoms of acne as well as reduction in porphyrins during and after weeks 2-8 of application. Compound E facial cream was well tolerated clinically in human subjects with acne prone skin and significantly outperforms BPO on the acne IGA clinical scale at week 2 and week 8. Moreover, a reduction in porphyrins on the face, is observed suggesting a reduction in *P. acnes* counts in vivo, supporting in vitro findings.

EQUIVALENTS

Those skilled in the art will recognize, or be able to ascertain using no more than routine experimentation, that while the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity, those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any targeting moiety, any disease, disorder, and/or condition, any linking agent, any method of administration, any therapeutic application, etc.) can be excluded from any one or more claims, for any reason, whether or not related to the existence of prior art.

Publications discussed above and throughout the text are provided solely for their disclosure prior to the filing date of the present application. Nothing herein is to be construed as an admission that the inventors are not entitled to antedate such disclosure by virtue of prior disclosure.

The invention claimed is:
1. A compound represented by the formula:

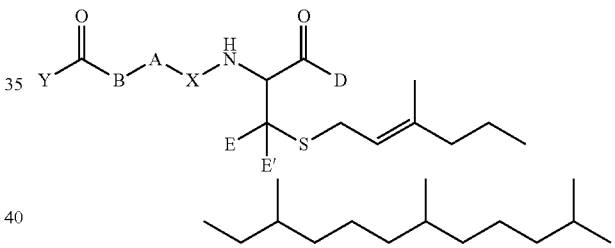

or a pharmaceutically acceptable salt, solvate, prodrug or ester thereof;
wherein:
X is —C(O)—, or a covalent bond;
Y is hydroxyl, —$NH_2$, —O—$C_1$-$C_5$ alkyl or $C_1$-$C_5$ alkyl;
A and B are independently selected from NR, N($C_1$-$C_5$ alkyl), N($C_1$-$C_5$ alkylene-R), N($C_1$-$C_5$ alkylene)-CN, N($C_1$-$C_5$ alkylene carboxyl), each of said alkyl or alkylene group optionally substituted with one or more R groups, —O—, a R-substituted or unsubstituted $C_1$-$C_5$ alkylene, a R-substituted or unsubstituted O—$C_1$-$C_5$ alkylene, a R-substituted or unsubstituted arylene or a R-substituted or unsubstituted heteroarylene having 1-4 heteroatoms independently selected from nitrogen, oxygen, or sulfur, or a R-substituted or unsubstituted $C_3$-$C_6$ cycloalkylene or R-substituted or unsubstituted $C_3$-$C_6$ heterocycloalkylene having 1-4 heteroatoms independently selected from nitrogen, oxygen, or sulfur;
or A and B together form a R-substituted or unsubstituted arylene or a R-substituted or unsubstituted heteroarylene having 1-4 heteroatoms independently selected from nitrogen, oxygen, or sulfur, or a R-substituted or unsubstituted $C_3$-$C_6$ cycloalkylene or R-substituted or unsubstituted $C_3$-$C_6$ heterocycloalkylene having 1-4 heteroatoms independently selected from nitrogen, oxygen, or sulfur;

D is —OH or —O($C_1$-$C_5$ alkyl),

E and E' are independently selected from H, and $C_1$-$C_5$ alkyl; and

R is, independently, H, $C_1$-$C_5$ alkyl, OH, S($C_1$-$C_5$ alkyl), NH($C_1$-$C_5$ alkyl), NH($C_1$-$C_5$ alkylene carboxyl), NH($C_1$-$C_5$ alkylene guanidine), N($C_1$-$C_5$ alkylene amidine), N($C_1$-$C_5$ alkylene amide), $CF_3$, —CN, —COOH, or O($C_1$-$C_5$ alkyl);

provided that when A and B are both —$CH_2$—, D is hydroxyl, X is —C(O)—, and E is hydrogen, Y cannot be hydroxyl, —$OCH_3$ or —$CH_3$.

2. The compound of claim 1, wherein Y is selected from OH and —$NH_2$.

3. The compound of claim 1 wherein A is selected from —$CH_2$—, —$CH_2NH$—, N-methyl, —O— and N($C_1$-$C_5$ alkylene carboxyl).

4. The compound of claim 1 wherein B is selected from —O— and unsubstituted O—$C_1$-$C_5$ alkylene.

5. The compound of claim 1 wherein B is —$CH_2$—.

6. The compound of claim 1 wherein A and B together form a R-substituted or unsubstituted arylene or a R-substituted or unsubstituted heteroarylene having 1-4 heteroatoms independently selected from nitrogen, oxygen, or sulfur, or a R-substituted or unsubstituted $C_3$-$C_6$ cycloalkylene or R-substituted or unsubstituted $C_3$-$C_6$ heterocycloalkylene having 1-4 heteroatoms independently selected from nitrogen, oxygen, or sulfur.

7. The compound of claim 1 wherein A and B together form an unsubstituted $C_3$-$C_6$ heterocycloalkylene having 1-4 nitrogen atoms or an unsubstituted heteroarylene having 1-4 nitrogen atoms.

8. The compound claim 1 wherein E and E' are each methyl.

9. The compound of claim 1 wherein D is —OH.

10. The compound of claim 1, wherein the compound is represented by the formula:

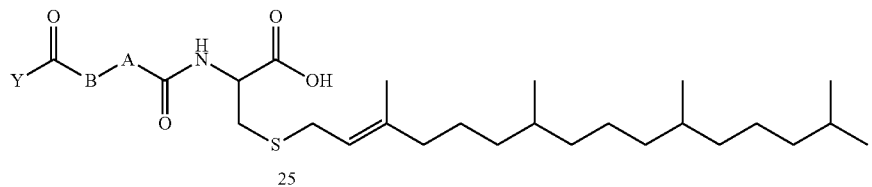

or a pharmaceutically acceptable salt, solvate, prodrug or ester thereof;

wherein:

Y is hydroxyl, —$NH_2$, —O—$C_1$-$C_5$ alkyl or $C_1$-$C_5$ alkyl;

A and B are independently selected from NR, N($C_1$-$C_5$ alkyl), N($C_1$-$C_5$ alkylene)-R, N($C_1$-$C_5$ alkylene)-CN, N($C_1$-$C_5$ alkylene carboxyl), each of said alkyl or alkylene group optionally substituted with one or more R groups, —O—, a R-substituted or unsubstituted $C_1$-$C_5$ alkylene, a R-substituted or unsubstituted O—$C_1$-$C_5$ alkylene, a R-substituted or unsubstituted arylene or a R-substituted or unsubstituted heteroarylene having 1-4 heteroatoms independently selected from nitrogen, oxygen, or sulfur, or a R-substituted or unsubstituted $C_3$-$C_6$ cycloalkylene or R-substituted or unsubstituted $C_3$-$C_6$ heterocycloalkylene having 1-4 heteroatoms independently selected from nitrogen, oxygen, or sulfur;

or A and B together form a R-substituted or unsubstituted arylene or a R-substituted or unsubstituted heteroarylene having 1-4 heteroatoms independently selected from nitrogen, oxygen, or sulfur, or a R-substituted or unsubstituted $C_3$-$C_6$ cycloalkylene or R-substituted or unsubstituted $C_3$-$C_6$ heterocycloalkylene having 1-4 heteroatoms independently selected from nitrogen, oxygen, or sulfur;

R is, independently, —H, $C_1$-$C_5$ alkyl, OH, S($C_1$-$C_5$ alkyl), NH($C_1$-$C_5$ alkyl), NH($C_1$-$C_5$ alkylene carboxyl), NH($C_1$-$C_5$ alkylene guanidine), N($C_1$-$C_5$ alkylene amidine), N($C_1$-$C_5$ alkylene amide) or O($C_1$-$C_5$ alkyl);

provided that when A and B are both —$CH_2$—, Y cannot be hydroxyl, —$OCH_3$ or —$CH_3$.

11. The compound of claim 1, wherein the compound is represented by the formula:

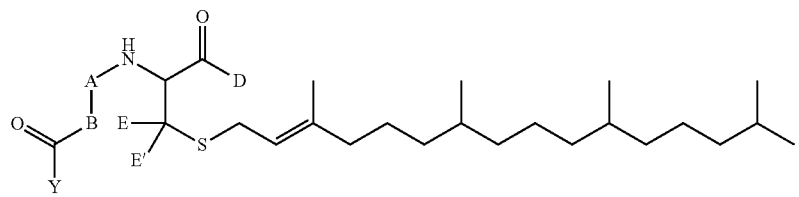

or a pharmaceutically acceptable salt, solvate, prodrug or ester thereof;
wherein:
Y is hydroxyl, —NH$_2$, —O—C$_1$-C$_5$ alkyl, or C$_1$-C$_5$ alkyl;
A and B together form a R-substituted or unsubstituted arylene or a R-substituted or unsubstituted heteroarylene having 1-4 heteroatoms independently selected from nitrogen, oxygen, or sulfur, or a R-substituted or unsubstituted C$_3$-C$_6$ cycloalkylene or R-substituted or unsubstituted C$_3$-C$_6$ heterocycloalkylene having 1-4 heteroatoms independently selected from nitrogen, oxygen, or sulfur;

D is —OH, —O(C$_1$-C$_5$ alkyl),
E and E' are independently selected from —H and C$_1$-C$_5$ alkyl; and
R is, independently, H, C$_1$-C$_5$ alkyl, OH, S(C$_1$-C$_5$ alkyl), NH(C$_1$-C$_5$ alkyl), NH(C$_1$-C$_5$ alkylene carboxyl), NH(C$_1$-C$_5$ alkylene guanidine), N(C$_1$-C$_5$ alkylene amidine), N(C$_1$-C$_5$ alkylene amide), CF$_3$, —CN, —COOH, or O(C$_1$-C$_5$ alkyl);
provided that when A and B are both —CH$_2$—, D is hydroxyl, and E is hydrogen, Y cannot be hydroxyl, —OCH$_3$ or —CH$_3$.

12. The compound of claim 1, wherein the compound is represented by the formula:

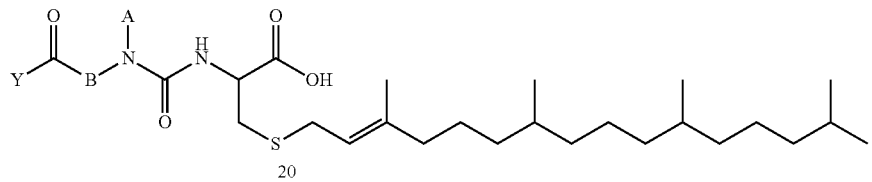

or a pharmaceutically acceptable salt, solvate, prodrug or ester thereof;
wherein:
Y is hydroxyl, —NH$_2$, —O—C$_1$-C$_5$ alkyl or C$_1$-C$_5$ alkyl;
A is selected from R, C$_1$-C$_5$ alkyl, (C$_1$-C$_5$ alkylene)-R, (C$_1$-C$_5$ alkylene)-CN, (C$_1$-C$_5$ alkylene)-carboxyl, each of said alkyl or alkylene group optionally substituted with one or more R groups;
B is an unsubstituted C$_1$-C$_2$ alkylene;
or A, B and the nitrogen atom bound to A and B form a R-substituted or unsubstituted C$_3$-C$_6$ heterocycloalkylene having 1-4 heteroatoms independently selected from nitrogen, oxygen, or sulfur; and
R is, independently, —H, C$_1$-C$_5$ alkyl, OH, S(C$_1$-C$_5$ alkyl), NH(C$_1$-C$_5$ alkyl), NH(C$_1$-C$_5$ alkylene carboxyl), NH(C$_1$-C$_5$ alkylene guanidine), N(C$_1$-C$_5$ alkylene amidine), N(C$_1$-C$_5$ alkylene amide), CF$_3$, —CN, —COOH, or O(C$_1$-C$_5$ alkyl).

13. The compound of claim 1, wherein the compound is represented by the formula:

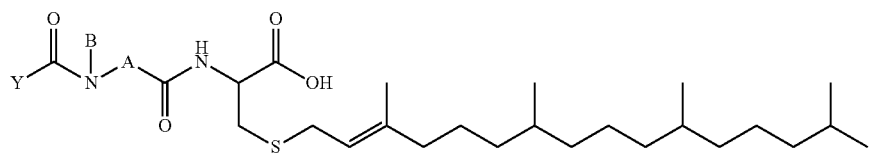

or a pharmaceutically acceptable salt, solvate, prodrug or ester thereof;
wherein:
Y is hydroxyl, —NH$_2$, —O—C$_1$-C$_5$ alkyl or C$_1$-C$_5$ alkyl;
A is an unsubstituted C$_1$-C$_2$ alkylene;
B is selected from R, C$_1$-C$_5$ alkyl, (C$_1$-C$_5$ alkylene)-R, (C$_1$-C$_5$ alkylene)-CN, (C$_1$-C$_5$ alkylene)-carboxyl, each of said alkyl or alkylene group optionally substituted with one or more R groups;
or A, B and the nitrogen atom bound to A and B form a R-substituted or unsubstituted C$_3$-C$_6$ heterocycloalkylene having 1-4 heteroatoms independently selected from nitrogen, oxygen, or sulfur; and
R is, independently, —H, C$_1$-C$_5$ alkyl, OH, S(C$_1$-C$_5$ alkyl), NH(C$_1$-C$_5$ alkyl), NH(C$_1$-C$_5$ alkylene carboxyl), NH(C$_1$-C$_5$ alkylene guanidine), N(C$_1$-C$_5$ alkylene amidine), N(C$_1$-C$_5$ alkylene amide), CF$_3$, —CN, —COOH, or O(C$_1$-C$_5$ alkyl).

14. A compound of claim 1, wherein the compound is represented by the formula:

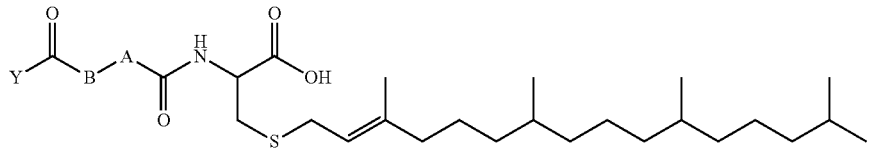

or a pharmaceutically acceptable salt, solvate, prodrug or ester thereof;
wherein:
Y is hydroxyl, —NH$_2$, —O—C$_1$-C$_5$ alkyl or C$_1$-C$_5$ alkyl;
A is NH, N(C$_1$-C$_5$ alkyl), N(C$_1$-C$_5$ alkylene carboxyl), or a R-substituted or unsubstituted C$_1$-C$_5$ alkylene;
B is NH, N(C$_1$-C$_5$ alkyl), N(C$_1$-C$_5$ alkylene carboxyl), or a R-substituted or unsubstituted C$_1$-C$_5$ alkylene;
or A and B together form a R-substituted or unsubstituted arylene or a R-substituted or unsubstituted heteroarylene having 1-4 heteroatoms independently selected from nitrogen, oxygen, or sulfur, or a R-substituted or unsubstituted C$_3$-C$_6$ cycloalkylene or R-substituted or unsubstituted C$_3$-C$_6$ heterocycloalkylene having 1-4 heteroatoms independently selected from nitrogen, oxygen, or sulfur;
R is, independently, C$_1$-C$_5$ alkyl, OH, S(C$_1$-C$_5$ alkyl), NH(C$_1$-C$_5$ alkyl), NH(C$_1$-C$_5$ alkylene carboxyl), NH(C$_1$-C$_5$ alkylene guanidine), N(C$_1$-C$_5$ alkylene amidine), N(C$_1$-C$_5$ alkylene amide) or O(C$_1$-C$_5$ alkyl);
provided that when A and B are both —CH$_2$—, Y cannot be hydroxyl, —OCH$_3$ or —CH$_3$.

15. The compound of claim 14, wherein (2S)-1-{[(1R)-1-carboxy-2-{[(2E)-3,7,11,15-tetramethylhexadec-2-en-1-yl]sulfanyl}ethyl]carbamoyl}pyrrolidine-2-carboxylic acid and (2R)-2-{[bis(carboxymethyl)carbamoyl]amino}-3-{[(2E)-3,7,11,15-tetramethylhexadec-2-en-1-yl]sulfanyl}propanoic acid are excluded.

16. A compound of claim 1, wherein the compound is represented by the formula:

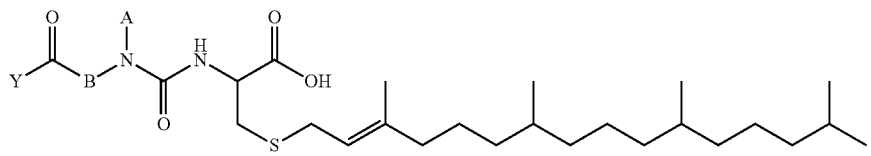

or a pharmaceutically acceptable salt, solvate, prodrug or ester thereof;
wherein:
Y is hydroxyl, —NH$_2$, —O—C$_1$-C$_5$ alkyl or C$_1$-C$_5$ alkyl;
A is hydrogen, an unsubstituted C$_1$-C$_2$ alkyl or CH$_2$COOH;
B is an unsubstituted C$_1$-C$_2$ alkylene;
or A, B and the nitrogen atom bound to A and B form a R-substituted or unsubstituted C$_3$-C$_6$ heterocycloalkylene having 1-4 heteroatoms independently selected from nitrogen, oxygen, or sulfur; and
R is C$_1$-C$_5$ alkyl, OH, S(C$_1$-C$_5$ alkyl), NH(C$_1$-C$_5$ alkyl), NH(C$_1$-C$_5$ alkylene carboxyl), NH(C$_1$-C$_5$ alkylene guanidine), N(C$_1$-C$_5$ alkylene amidine), N(C$_1$-C$_5$ alkylene amide), or O(C$_1$-C$_5$ alkyl).

17. The compound of claim 16, wherein (2S)-1-{[(1R)-1-carboxy-2-{[(2E)-3,7,11,15-tetramethylhexadec-2-en-1-yl]sulfanyl}ethyl]carbamoyl}pyrrolidine-2-carboxylic acid and (2R)-2-{[bis(carboxymethyl)carbamoyl]amino}-3-{[(2E)-3,7,11,15-tetramethylhexadec-2-en-1-yl]sulfanyl}propanoic acid are excluded.

18. A compound of claim 1, wherein the compound is represented by the formula:

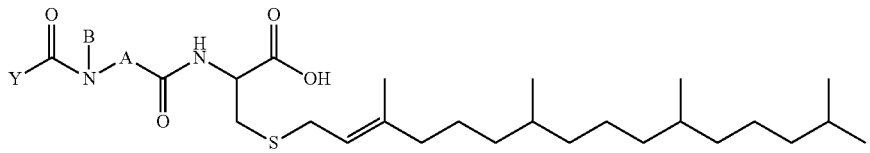

or a pharmaceutically acceptable salt, solvate, prodrug or ester thereof;
wherein:
Y is hydroxyl, —NH$_2$, —O—C$_1$-C$_5$ alkyl or C$_1$-C$_5$ alkyl;
A is an unsubstituted C$_1$-C$_2$ alkylene;
B is hydrogen, an unsubstituted C$_1$-C$_2$ alkyl or CH$_2$COOH;
or A, B and the nitrogen atom bound to A and B form a R-substituted or unsubstituted C$_3$-C$_6$ heterocycloalkylene having 1-4 heteroatoms independently selected from nitrogen, oxygen, or sulfur; and
R is C$_1$-C$_5$ alkyl, OH, S(C$_1$-C$_5$ alkyl), NH(C$_1$-C$_5$ alkyl), NH(C$_1$-C$_5$ alkylene carboxyl), NH(C$_1$-C$_5$ alkylene guanidine), N(C$_1$-C$_5$ alkylene amidine), N(C$_1$-C$_5$ alkylene amide), or O(C$_1$-C$_5$ alkyl).

19. The compound of claim 18, wherein (2S)-1-{[(1R)-1-carboxy-2-{[(2E)-3,7,11,15-tetramethylhexadec-2-en-1- yl]sulfanyl}ethyl]carbamoyl}pyrrolidine-2-carboxylic acid and (2R)-2-{[bis(carboxymethyl)carbamoyl]amino}-3-{[(2E)-3,7,11,15-tetramethylhexadec-2-en-1-yl]sulfanyl} propanoic acid are excluded.

20. A composition suitable for administration to a human comprising an effective amount of a compound according to claim 1 and one or more of a pharmaceutically acceptable adjuvant, a pharmaceutically acceptable carrier and a pharmaceutically acceptable vehicle.

* * * * *